US00H002260H

(19) United States
(12) Statutory Invention Registration
Toleikis

(10) Reg. No.: US H2260 H
(43) Published: Jul. 5, 2011

(54) STENTS COMBINED WITH PACLITAXEL DERIVATIVES

(75) Inventor: Philip M. Toleikis, Vancouver (CA)

(73) Assignee: Angiotech International AG, Zug (CH)

(21) Appl. No.: 11/357,368

(22) Filed: Feb. 17, 2006

Related U.S. Application Data

(60) Provisional application No. 60/653,844, filed on Feb. 17, 2005.

(51) Int. Cl.
*A61F 2/00* (2006.01)

(52) U.S. Cl. ..... 424/423

(58) Field of Classification Search ..... 424/423
See application file for complete search history.

(56) References Cited

U.S. PATENT DOCUMENTS

| | | | | |
|---|---|---|---|---|
| 4,876,399 | A | 10/1989 | Holton et al. | 568/817 |
| 4,942,184 | A | 7/1990 | Haugwitz et al. | 514/449 |
| 5,352,806 | A | 10/1994 | Gunawardana et al. | 549/510 |
| 5,440,056 | A | 8/1995 | Klein et al. | 549/510 |
| 5,468,769 | A | 11/1995 | Klein et al. | 514/449 |
| 5,616,608 | A | 4/1997 | Kinsella et al. | 514/449 |
| 5,716,981 | A | 2/1998 | Hunter et al. | 514/449 |
| 5,733,925 | A | 3/1998 | Kunz et al. | 514/449 |
| 6,074,659 | A | 6/2000 | Kunz et al. | 424/423 |
| 6,171,609 | B1 | 1/2001 | Kunz | 424/422 |
| 6,268,390 | B1 | 7/2001 | Kunz | 514/411 |
| 6,306,421 | B1 | 10/2001 | Kunz et al. | 424/423 |
| 6,403,635 | B1 | 6/2002 | Kinsella et al. | 514/449 |
| 6,491,938 | B2 | 12/2002 | Kunz et al. | 424/423 |
| 6,515,009 | B1 | 2/2003 | Kunz et al. | 514/411 |
| 6,515,016 | B2 | 2/2003 | Hunter | 514/449 |
| 6,599,928 | B2 | 7/2003 | Kunz et al. | 514/411 |
| 2005/0181977 | A1 | 8/2005 | Hunter et al. | 514/2 |

FOREIGN PATENT DOCUMENTS

| | | |
|---|---|---|
| WO | WO 91/12779 | 9/1991 |

OTHER PUBLICATIONS

Fleischer, David E., et al., "A New Coated Self–Expanding Metal Stent for Malignant Esophageal Strictures, " *Gastrointestinal Endoscopy* 38(4):494–496, 1992.

Stierle, Andrea, et al., "Taxol and Taxane Production by *Taxomyces andreanae*, an Endophytic Fungus of Pacific Yew, " *Science* 260:214–216, Apr. 9, 1993.

Wani, M.C., et al., "Plant Antitumor Agents. VI. The Isolation and Structure of Taxol, a Novel Antileukemic and Antitumor Agent from *Taxus brevifolia*, " *Journal of the American Chemical Society*, 93(9):2325–2327, May 5, 1971.

*Primary Examiner*—Michelle Clement

(57) ABSTRACT

Stents are used in combination with a paclitaxel derivative in order to inhibit scarring that may otherwise occur when the implant is placed within an animal. Suitable implants include vascular stents, esophageal stents, tracheal or bronchial stents, gastrointestinal stents, genital-urinary stents, nasal and sinus stents, and ENT stents.

26 Claims, 19 Drawing Sheets

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

Uninjured carotid artery - Rat balloon injury model

Control injured carotid artery - Rat balloon injury model

Paclitaxel/mesh treated carotid artery - Rat balloon injury model (345 ug paclitaxel in a 50:50 PLG coating on a 10:90 PLG mesh)

Ly 290181

| | | | | | | |
|---|---|---|---|---|---|---|
| IL-1 (ng/mL) | 0 | 20 | 20 | 20 | 20 | 20 |
| Drug (M) | 0 | 0 | $10^{-7}$ | $10^{-6}$ | $10^{-5}$ | $10^{-4}$ |

2-Methyl-2,4-Pentanediol (Hexylene Glycol)

| | | | | | | |
|---|---|---|---|---|---|---|
| IL-1 (ng/mL) | 0 | 20 | 20 | 20 | 20 | 20 |
| Drug (M) | 0 | 0 | $10^{-7}$ | $10^{-6}$ | $10^{-5}$ | $10^{-4}$ |

Ethylene Glycol Bis-
(succinimidylsuccinate)

| | | | | | | |
|---|---|---|---|---|---|---|
| IL-1 (ng/mL) | 0 | 20 | 20 | 20 | 20 | 20 |
| Drug (M) | 0 | 0 | $10^{-7}$ | $10^{-6}$ | $10^{-5}$ | $10^{-4}$ |

Tubercidin

Aluminum Fluoride

| | | | | | | |
|---|---|---|---|---|---|---|
| IL-1 (ng/mL) | 0 | 20 | 20 | 20 | 20 | 20 |
| Drug (M) | 0 | 0 | $10^{-7}$ | $10^{-6}$ | $10^{-5}$ | $10^{-4}$ |

Paclitaxel $IC_{50}$=7 nM for proliferation of human smooth muscle cells.

Paclitaxel $IC_{50}$=23 nM for proliferation of human fibroblasts.

Paclitaxel $IC_{50}$=134 nM for proliferation of the murine RAW 264.7 macrophage cell line.

STENTS COMBINED WITH PACLITAXEL DERIVATIVES

CROSS-REFERENCE TO RELATED APPLICATION

This application claims the benefit under 35 U.S.C. § 119 (e) of U.S. Provisional Patent Application No. 60/653,844, filed Feb. 17, 2005, which application is incorporated herein by reference in its entirety.

BACKGROUND OF THE INVENTION

1. Field of the Invention

The present invention relates generally to pharmaceutical compositions that include paclitaxel derivatives and methods for preparing and using stent devices to make them resistant to overgrowth by inflammatory and fibrous scar tissue.

2. Description of the Related Art

The clinical function of numerous medical implants and devices is dependent upon the device being able to effectively maintain an anatomical, or surgically created, space or passageway. Unfortunately, many devices implanted in the body are subject to a "foreign body" response from the surrounding host tissues. In particular, injury to tubular anatomical structures (such as blood vessels, the gastrointestinal tract, the male and female reproductive tract, the urinary tract, sinuses, spinal nerve root canals, lacrimal ducts, Eustachian tubes, the auditory canal, and the respiratory tract) from surgery and/or injury created by the implantation of medical devices can lead to a well known clinical problem called "stenosis" (or narrowing). Stenosis occurs in response to trauma to the epithelial lining or the entire body tube during the procedure, including virtually any manipulation which attempts to relieve obstruction of the passageway, and is a major factor limiting the effectiveness of invasive treatments for a variety of diseases to be described later.

Stenosis (or "restenosis" if the problem recurs after an initially successful attempt to open a blocked passageway) is a form of response to injury leading to wall thickening, narrowing of the lumen, and loss of function in the tissue supplied by the particular passageway. Physical injury during an interventional procedure results in damage to epithelial lining of the tube and the smooth muscle cells (SMCs) that make up the wall. The damaged cells, particularly SMCs, release cytokines, which recruit inflammatory cells such as macrophages, lymphocytes and neutrophils (i.e., which are some of the known white blood cells) into the area. The white blood cells in turn release a variety of additional cytokines, growth factors, and tissue degrading enzymes that influence the behavior of the constituent cells of the wall (primarily epithelial cells and SMCs). Stimulation of the SMCs induces them to migrate into the inner aspect of the body passageway (often called the "intima"), proliferate and secrete an extracellar matrix—effectively filling all or parts of the lumen with reactive, fibrous scar tissue. Collectively, this creates a thickening of the intimal layer (known in some tissues as "neointimal hyperplasia" that narrows the lumen of the passageway and can be significant enough to obstruct its lumen.

BRIEF SUMMARY OF THE INVENTION

Briefly stated, in one aspect, the present invention provides medical devices (e.g., stents) that are coated or otherwise contain paclitaxel derivatives or compositions comprising paclitaxel derivatives, methods for making such devices, methods for inhibiting fibrosis comprising placing medical devices that are coated with, or otherwise contain, paclitaxel derivatives or compositions comprising paclitaxel derivatives, and methods for inhibiting fibrosis comprising separately placing a medical device and applying at least one of (i) a paclitaxel derivative and (ii) a composition that comprises a paclitaxel derivative into an animal. Paclitaxel derivatives or compositions comprising paclitaxel derivatives are delivered in therapeutic levels over a period sufficient to allow normal healing to occur at or near the site where a medical device is implanted. For example, within one aspect of the invention, paclitaxel derivate-coated or paclitaxel derivate-impregnated medical devices are provided that reduce fibrosis in the tissue surrounding the devices or inhibit scar development on the device surface.

The repair of tissues following a mechanical or surgical intervention involves two distinct processes: (1) regeneration (the replacement of injured cells by cells of the same type) and (2) fibrosis (the replacement of injured cells by connective tissue). There are four general components to the process of fibrosis (or scarring) including: formation of new blood vessels (angiogenesis), migration and proliferation of connective tissue cells (such as fibroblasts or smooth muscle cells), deposition of extracellular matrix (ECM), and remodeling (maturation and organization of the fibrous tissue). Within one embodiment of the invention, a device is adapted to release a paclitaxel derivative that inhibits fibrosis or regeneration through one or more of the mechanisms sited herein.

In one aspect, the present invention provide a device, comprising a stent and a paclitaxel derivative or a composition comprising a paclitaxel derivative, wherein the paclitaxel derivative inhibits scarring between the device and a host into which the device is implanted.

In certain embodiments, the paclitaxel derivative may be 9-deoxotaxol, 7-deoxy-9-deoxotaxol, 10-desacetoxy-7-deoxy-9-deoxotaxol, 9-dihydrotaxol compound, 2'-O-ethoxyethyl-7-O-trietylsilyl-9-dihydrotaxol, 2'-O-ethoxyethyl-9-dihydrotaxol, 10-deacetyl-9-dihydrotaxol, 9-dihydrotaxol-7,9-isopropylidene ketal, 9-dihydrotaxol-7,9-propylidene acetal, 9-dihydrotaxol-7,9-benzylidene acetal, 9-dihydrotaxol-7,9-(3,4-dihydroxy)butylidene acetal, 9-dihydrotaxol-7,9-thionocarbonate, 9-dihydrotaxol-7-O-allyl ether, 9-dihydrotaxol-7-O-(2,3-dihydroxypropyl) ether, 9-dihydrotaxol 7-O-(2-dimethylaminoethyl) ether, 9-dihydrotaxol 7-O-(2-hydroxyethyl) ether, 9-dihydrotaxol 7-O-(2-acetoxyethyl) ether, N-debenzoyl-N-t-butoxycarbonyl-9-dihydrotaxol, 10-deacetyl-N-debenzoyl-N-t-butoxycarbonyl-9-dihydrotaxol, N-debenzoyl-N-t-butylacetyl-9-dihydrotaxol, N-debenzoyl-N-isobutoxycarbonyl-9-dihydrotaxol, N-debenzoyl-N-adamantoxycarbonyl-9-dihydrotaxol, N-debenzoyl-N-isopropoxycarbonyl-9-dihydrotaxol, N-debenzoyl-N-benzyloxycarbonyl-9-dihydrotaxol, N-debenzoyl-9-dihydrotaxol, N-debenzoyl-N-pivaloyl-9-dihydrotaxol, N-debenzoyl-N-acetyl-9-dihydrotaxol, N-debenzoyl-N-t-butylcarbamyl-9-dihydrotaxol, 9-dihydro-13-acetylbaccatin III, 2'-O-(1-ethyoxyethyl)-9-dihydrotaxol, 4,9,12-tris (acetyloxy)-2-benzoyloxy-8-formyl-1,2,3,4,5,6,7,8,10,13,14-undecahydro-1-hydroxy-7,14,14,17-tetramethyl-1,10-methano-20H-cyclonona[2,3]benz[1,2-b]oxete, β-tert-butyloxycarbonylamino-α-hydroxybenzenepropanoic acid 4,9-bis(acetyloxy)-2-benzoyloxy-8-formyl-1,2,3,4,5,6,7,8,10,13,14-undecahydro-1-hydroxy-7,14,14,17-tetramethyl-1,10-methano-20H-cyclonona[2,3]benz[1,2-b]oxet-12-yl ester, β-benzoylamino-α-hydroxybenzenepropanoic acid 4,9-bis(acetyloxy)-2-benzoyloxy-8-formyl-1,2,3,4,5,6,7,8, 10,13,14-undecahydro-1-hydroxy-7,14,14,17-tetramethyl-1,10-methano-20H-cyclonona[2,3]benz[1,2-b]oxet-12-yl ester, 4,9,12(tris(acetyloxy)-2-benzoyloxy-8-formyl-1,2,3,4,5,6,7,8,10,13,14-undecahydro-1-hydroxy-7,14,14,17-tetramethyl-1,10-methano-20H-cyclonona[2,3]benz[1,2-b]oxete, 4,9,12-tris(acetyloxy)-2-benzoyloxy-1,2,3,4,5,6,7,8,10,13,14-undecahydro-1-hydroxy-8-hydroxymethyl-7,14,14,17-tetramethyl-1,10-methano-20H-cyclonona[2,3]benz[1,2-b]oxete, 4,9,12-tris(acetyloxy)-2-benzoyloxy-1,2,3,4,5,6,7,8,10,13,14-undecahydro-1-hydroxy-8-methoxymethyl-7,14,14,17-tetramethyl-1,10-methano-20H-cyclonona[2,3]benz[1,2-b]oxete, 4,9,12-tris(acetyloxy)-2-benzoyloxy-1,2,3,4,5,6,7,8,10,13,14-undecahydro-1-hydroxy-8-ethoxymethyl-7,14,14,17-tetramethyl-1,10-methano-20H-cyclonona[2,3]benz[1,2-b]oxete, 4,9,12-tris(acetyloxy)-8-acetyloxymethyl-2-benzoyloxy-1,2,3,4,5,6,7,8,10,13,14-undecahydro-1-hydroxy-7,14,14,17-tetramethyl-1,10-methano-20H-cyclonona[2,3]benz[1,2-b]oxete, 4,9,12-tris(acetyloxy)-2-benzoyloxy-8-dimethylaminomethyl-1,2,3,4,5,6,7,8,10,13,14-undecahydro-1-hydroxy-7,14,14,17-tetramethyl-1,10-methano-20H-cyclonona[2,3]benz[1,2-b]oxete, 4,9,12-tris(acetyloxy)-2-benzoyloxy-8-diethylaminomethyl-1,2,3,4,5,6,7,8,10,13,14-undecahydro-1-hydroxy-7,14,14,17-tetramethyl-1,10-methano-20H-cyclonona[2,3]benz[1,2-b]oxete, 4,9,12-tris(acetyloxy)-2-benzoyloxy-1,2,3,4,5,6,7,8,10,13,14-undecahydro-1-hydroxy-7,14,14,17-tetramethyl-8-methylamino-1,10-methano-20H-cyclonona[2,3]benz[1,2-b]oxete, 4,9,12-tris(acetyloxy)-2-benzoyloxy-1,2,3,4,5,6,7,8,10,13,14-undecahydro-1-hydroxy-7,14,14,17-tetramethyl-8-ethylamino-1,10-methano-20H-cyclonona[2,3]benz[1,2-b]oxete, 4,9,12-tris(acetyloxy)-2-benzoyloxy-1,2,3,4,5,6,7,8,10,13,14-undecahydro-1-hydroxy-7,14,14,17-tetramethyl-8-methylimino-1,10-methano-20H-cyclonona[2,3]benz[1,2-b]oxete, 4,9,12-tris(acetyloxy)-2-benzoyloxy-1,2,3,4,5,6,7,8,10,13,14-undecahydro-1-hydroxy-7,14,14,17-tetramethyl-8-methoxyimino-1,10-methano-20H-cyclonona[2,3]benz[1,2-b]oxete, 4,9,12-tis(acetyloxy)-2-benzoyloxy-1,2,3,4,5,6,7,8,10,13,14-undecahydro-1-hydroxy-7,14,14,17-tetramethyl-8-methylhydrazinomethyl-1,10-methano-20H-cyclonona[2,3]benz[1,2-b]oxete, 4,9,12-tris(acetyloxy)-2-benzoyloxy-8-cyano-1,2,3,4,5,6,7,8,10,13,14-1-undecahydro-1-hydroxy-7,14,14,17-tetramethyl-1,10-methano-20H-cyclonona[2,3]benz[1,2-b]oxete, 4,9,12-tris(acetyloxy)-2-benzoyloxy-1,2,3,4,5,6,7,8,10,13,14-undecahydro-1-hydroxy-7,14,14,17-tetramethyl-1,10-methano-20H-cyclonona[2,3]benz[1,2-b]oxete-8-methylsulfate, 4,9,12-tris(acetyloxy)-2-benzoyloxy-1,2,3,4,5,6,7,8,10,13,14-undecahydro-1-hydroxy-7,14,14,17-tetramethyl-1,10-methano-20H-cyclonona[2,3]benz[1,2-b]oxete-8-methylphosphate, 4,9,12-tris(acetyloxy)-2-benzoyloxy-8-(1,3-dioxolan-2-yl)-1,2,3,4,5,6,7,8,10,13,14-undecahydro-1-hydroxy-7,14,14,17-tetramethyl-1,10-methano-20H-cyclonona[2,3]benz[1,2-b]oxete, 4,9,12-tris(acetyloxy)-2-benzoyloxy-8-(tetrahydro-oxazole-2-yl)-1,2,3,4,5,6,7,8,10,13,14-undecahydro-1-hydroxy-7,14,14,17-tetramethyl-1,10-methano-20H-cyclonona[2,3]benz[1,2-b]oxete, 4,9,12-tris(acetyloxy)-2-benzoyloxy-8-(1,3-dithiolane-2-yl)-1,2,3,4,5,6,7,8,10,13,14-undecahydro-1-hydroxy-7,14,14,17-tetramethyl-1,10-methano-20H-cyclonona[2,3]benz[1,2-b]oxete, 4,9-bis(acetyloxy)-2-benzoyloxy-8-formyl-1,12-dihydroxy-1,2,3,4,5,6,7,8,10,13,14-undecahydro-7,14,14,17-tetramethyl-1,10-methano-20H-cyclonona[2,3]benz[1,2-b]oxete, 4,9-bis(acetyloxy)-2-benzoyloxy-1,12-dihydroxy-1,2,3,4,5,6,7,8,10,13,14-undecahydro-8-hydroxymethyl-7,14,14,17-tetramethyl-1,10-methano-20H-cyclonona[2,3]benz[1,2-b]oxete, 4,9-bis(acetyloxy)-2-benzoyloxy-1,12-dihydroxy-1,2,3,4,5,6,7,8,10,13,14-undecahydro-8-methoxymethyl-7,14,14,17-tetramethyl-1,10-methano-20H-cyclonona[2,3]benz[1,2-b]oxete, 4,9-bis(acetyloxy)-2-benzoyloxy-1,12-dihydroxy-1,2,3,4,5,6,7,8,10,13,14-undecahydro-8-ethoxymethyl-7,14,14,17-tetramethyl-1,10-methano-20H-cyclonona[2,3]benz[1,2-b]oxete, 4,9-bis(acetyloxy)-8-acetyloxymethyl-2-benzoyloxy-1,12-dihydroxy-1,2,3,4,5,6,7,8,10,13,14-undecahydro-7,14,14,17-tetramethyl-1,10-methano-20H-cyclonona[2,3]benz[1,2-b]oxete, 4,9-bis(acetyloxy)-2-benzoyloxy-8-dimethylaminomethyl-1,12-dihydroxy-1,2,3,4,5,6,7,8,10,13,14-undecahydro-7,14,14,17-tetramethyl-1,10-methano-20H-cyclonona[2,3]benz[1,2-b]oxete, 4,9-bis(acetyloxy)-2-benzoyloxy-8-diethylaminomethyl-1,12-dihydroxy-1,2,3,4,5,6,7,8,10,13,14-undecahydro-7,14,14,17-tetramethyl-1,10-methano-20H-cyclonona[2,3]benz[1,2-b]oxete, 4,9-bis(acetyloxy)-2-benzoyloxy-1,12-dihydroxy-1,2,3,4,5,6,7,8,10,13,14-1-undecahydro-7,14,14,17-tetramethyl-8-methylamino-1,10-methano-20H-cyclonona[2,3]benz[1,2-b]oxete, 4,9-bis(acetyloxy)-2-benzoyloxy-1,12-dihydroxy-1,2,3,4,5,6,7,8,10,13,14-undecahydro-7,14,14,17-tetramethyl-8-ethylamino-1,10-methano-20H-cyclonona[2,3]benz[1,2-b]oxete, 4,9-bis(acetyloxy)-2-benzoyloxy-1,12-dihydroxy-1,2,3,4,5,6,7,8,10,13,14-undecahydro-7,14,14,17-tetramethyl-8-methylimino-1,10-methano-20H-cyclonona[2, 3]benz[1,2-b]oxete, 4,9-bis(acetyloxy)-2-benzoyloxy-1,12-dihydroxy-1,2,3.4,5,6,7,8,10,13,14-undecahydro-7,14,14,17-tetramethyl-8-methoxyimino-1,10-methano-20H-cyclonona[2,3]benz[1,2-b]oxete, 4,9-bis(acetyloxy)-2-benzoyloxy-1,12-dihydroxy-1,2,3,4,5,6,7,8,10,13,14-undecahydro-7,14,14,17-tetramethyl-8-methylhydrazinomethyl-1,10-methano-20H-cyclonona[2,3]benz[1,2-b]oxete, 4,9-bis(acetyloxy)-2-benzoyloxy-8-cyano-1,12-dihydroxy-1,2,3,4,5,6,7,8,10,13,14-undecahydro-7,14,14,17-tetramethyl-1,10-methano-20H-cyclonona[2,3]benz[1,2-b]oxete, 4,9-bis(acetyloxy)-2-benzoyloxy-1,12-dihydroxy-1,2,3,4,5,6,7,8,10,13,14-undecahydro-7,14,14,17-tetramethyl-1,10-methano-20H-cyclonona[2,3]benz[1,2-b]oxete-8-methylsulfate, 4,9-bis(acetyloxy)-2-benzoyloxy-1,12-dihydroxy-1,2,3,4,5,6,7,8,10,13,14-undecahydro-7,14,14,17-tetramethyl-1,10-methano-20H-cyclonona[2,3]benz[1,2-b]oxete-8-methylphosphate, 4,9-bis(acetyloxy)-2-benzoyloxy-8-(1,3-dioxolan-2-yl)-1,12-dihydroxy-1,2,3,4,5,6,7,8,10,13,14-undecahydro-7,14,14,17-tetramethyl-1,10-methano-20H-cyclonona[2,3]benz[1,2-b]oxete, 4,9-bis(acetyloxy)-2-benzoyloxy-8-(tetrahydro-oxazole-2-yl)-1,12-dihydroxy-1,2,3,4,5,6,7,8,10,13,14-undecahydro-7,14,14,17-tetramethyl-1,10-methano-20 H-cyclonona[2,3]benz[1,2-b]oxete, 4,9-bis(acetyloxy)-2-benzoyloxy-8-(1,3-dithiolane-2-yl)-1,12-dihydroxy-1,2,3,4,5,6,7,8,10,13,14-undecahydro-7,14,14,17-tetramethyl-1,10-methano-20H-cyclonona[2,3]benz[1,2-b]oxete, b-benzoylamino-α-hydroxybenzenepropanoic acid 4,9-bis(acetyloxy)-2-benzoyloxy-1,2,3,4,5,6,7,8,10,13,14-undecahydro-1-hydroxy-8-hydroxymethyl-7,14,14,17-tetramethyl-1,10-methano-20H-cyclonona[2,3]benz[1,2-b]oxet-12-yl ester, β-benzoylamino-α-hydroxybenzenepropanoic acid 4,9-bis(acetyloxy)-2-benzoyloxy-1,2,3,4,5,6,7,8,10,13,14-undecahydro-1-hydroxy-8-methoxymethyl-7,14,14,17-tetramethyl-1,10-methano-20H-cycionona[2,3]benz[1,2-b]oxet-12-yl ester, β-benzoylamino-α-hydroxybenzenepropanoic acid 4,9-bis(acetyloxy)-2-benzoyloxy-1,2,3,4,5,6,7,8,10,13,14-undecahydro-1-hydroxy-8-ethoxymethyl-7,14,14,17-tetramethyl-1,10-methano-20H-cyclonona[2,3]benz[1,2-b]oxet-12-yl ester, β-benzoylamino-α-hydroxybenzenepropanoic acid 4,9-bis (acetyloxy)-8-acetyloxymethyl-2-benzoyloxy-1,2,3,4,5,6,7,8,10,13,14-undecahydro-1-hydroxy-7,14,14,17-tetramethyl-1,10-methano-20H-cyclonona[2,3]benz[1,2-b]oxet-12-yl ester, β-benzoylamino-α-hydroxybenzenepropanoic acid 4,9-bis(acetyloxy)-2-benzoyloxy-8-dimethylaminomethyl-1,2,3,4,5,6,7,8,10,13,14-undecahydro-1-hydroxy-7,14,14,17-tetramethyl-1,10-methano-20H-cyclonona[2,3]benz[1,2-b]oxet-12-yl ester, β-benzoylamino-α-hydroxybenzenepropanoic acid 4,9-bis(acetyloxy)-2-benzoyloxy-8-diethylaminomethyl-1,2,3,4,5,6,7,8,10,13,14-undecahydro-1-hydroxy-7,14,14,17-tetramethyl-1,10-methano-20H-cyclonona[2,3]benz[1,2-b]oxet-12-yl ester, 1,3-benzoylamino-α-hydroxybenzenepropanoic acid 4,9-bis(acetyloxy)-2-benzoyloxy-1,2,3,4,5,6,7,8,10,13,14-undecahydro-1-hydroxy-7,14,14,17-tetramethyl-8-methylaminomethyl-1,10-methano-20H-cyclonona[2,3]benz[1,2b]oxet-12-yl ester, β-benzoylamino-α-hydroxybenzenepropanoic acid 4,9-bis(acetyloxy)-2-benzoyloxy-1,2,3,4,5,6,7,8,10,13,14-undecahydro-1-hydroxy-7,14,14,17-tetramethyl-8-methylimino-1,10-methano-20H-cyclonona[2,3]benz[1,2-b]oxet-12-yl ester, β-benzoylamino-α-hydroxybenzenepropanoic acid 4,9-bis(acetyloxy)-2-benzoyloxy-1,2,3,4,5,6,7,8,10,13,14-undecahydro-1-hydroxy-7,14,14,17-tetramethyl-8-methoxyimino-1,10-methano-20H-cyclonona[2,3]benz[1,2-b]oxet-12-yl ester, β-benzoylamino-α-hydroxybenzenepropanoic acid 4,9-bis(acetyloxy)-2-benzoyloxy-1,2,3,4,5,6,7,8,10,13,14-undecahydro-1-hydroxy-7,14,14,17-tetramethyl-8-methyihydrazinomethyl-1,10-methano-20H-cyclonona[2,3]benz[1,2-b]oxet-12-yl ester, β-benzoylamino-α-hydroxybenzenepropanoic acid 4,9-bis(acetyloxy)-2-benzoyloxy-8-cyano-1,2,3,4,5,6,7,8,10,13,14-undecahydro-1-hydroxy-7,14,14,17-tetramethyl-1,10-methano-20H-cyclonona[2,3]benz[1,2-b]oxet-12-yl ester, β-benzoylamino-α-hydroxybenzenepropanoic acid 4,9-bis(acetyloxy)-2-benzoyloxy-8-(1,3-dioxolane-2-yl)-1,2,3,4,5,6,7,8,10,13,14-undecahydro-1-hydroxy-7,14,14,17-tetramethyl-1,10-methano-20H-cyclonona[2,3]benz[1,2-b]oxet12-yl ester, β-benzoylamino-α-(tetrahydro-oxazole-2-yl)-1,2,3,4,5,6,7,8,10,13,14-undecahydro-1-hydroxy-7,14,14,17-tetramethyl-1,10-methano-20H-cyclonona[2,3]benz[1,2-b]oxet-12-yl ester, β-benzoylamino-α-hydroxybenzenepropanoic acid 4,9-bis(acetyloxy)-2-benzoyloxy-8-(1,3-dithiolane-2-yi)-1,2,3,4,5,6,7,8,10,13,14-undecahydro-1-hydroxy-7,14,14,17-tetramethyl-1,10-methano-20H-cyclonona[2,3]benz[1,2-b]oxet12-yl ester, β-tert-butyloxycarbonylamino-α-hydroxybenzenepropanoic acid 4,9-bis(acetyloxy)-2-benzoyloxy-8-formyl-1,2,3,4,5,6,7,8,10,13,14-undecahydro-1-hydroxy-7,14,14,17-tetramethyl-1,10-methano-20H-cyclonona[2,3]benz[1,2-b]oxet-12-yl ester, β-tert-butyloxycarbonylamino-α-hydroxybenzenepropanoic acid 4,9-bis(acetyloxy)-2-benzoyloxy-1,2,3,4,5,6,7,8,10,13,14-undecahydro-1-hydroxy-8-hydroxymethyl-7,14,14,17-tetramethyl-1,10-methano-20H-cyclonona[2,3]benz[1,2b]oxet-12-yl ester, β-tert-butyloxycarbonylamino-α-hydroxybenzenepropanoic acid 4,9-bis(acetyloxy)-2-benzoyloxy-1,2,3,4,5,6,7,8,10,13,14-undecahydro-1-hydroxy-8-methoxymethyl-7,14,14,17-tetramethyl-1,10-methano-20H-cyclonona[2,3benz[1,2-b]oxet-12-yl ester, β-tert-butyloxycarbonylamino-α-hydroxybenzenepropanoic acid 4,9-bis(acetyloxy)-2-benzoyloxy-1,2,3,4,5,6,7,8,10,13,14-undecahydro-1-hydroxy-8-ethoxymethyl-7,14,14,17-tetramethyl-1,10-methano-20H-cyclonona[2,3]benz[1,2-b]oxet-12-yl ester, β-tert-butyloxycarbonylamino-α-hydroxybenzenepropanoic acid 4,9-bis(acetyloxy)-8-acetyloxymethyl-2-benzoyloxy-1,2,3,4,5,6,7,8,10,13,14-undecahydro-1-hydroxy-7,14,14,17-tetramethyl-1,10-methano-20H-cyclonona[2,3]benz[1,2-b]oxet-12-yl ester, β-tert-butyloxycarbonylamino-α-hydroxybenzenepropanoic acid 4,9-bis(acetyloxy)-2-benzoyloxy-8-dimethylaminomethyl-1,2,3,4,5,6,7,8,10,13,14-undecahydro-1-hydroxy-7,14,14,17-tetramethyl-1,10-methano-20H-cyclonona[2,3]benz[1,2-b]oxet-12-yl ester, β-tert-butyloxycarbonylamino-α-hydroxybenzenepropanoic acid 4,9-bis(acetyloxy)-2-benzoyloxy-8-diethylaminomethyl-1,2,3,4,5,6,7,8,10,13,14-undecahydro-1-hydroxy-7,14,14,17-tetramethyl-1,10-methano-20H-cyclonona[2,3]benz[1,2-b]oxet-12-yl ester, β-tert-butyloxycarbonylamino-α-hydroxybenzenepropanoic acid 4,9-bis(acetyloxy)-2-benzoyloxy-1,2,3,4,5,6,7,8,10,13,14-undecahydro-1-hydroxy-7,14,14,17-tetramethyl-8-methylaminomethyl-1,10-methano-20H-cyclonona[2,3]benz[1,2-b]oxet-12-yl ester, β-tert-butyloxycarbonylamino-α-hydroxybenzenepropanoic acid 4,9-bis(acetyloxy)-2-benzoyloxy-1,2,3,4,5,6,7,8,10,13,14-undecahydro-1-hydroxy-7,14,14,17-tetramethyl-8-methylimino-1,10-methano-20H-cyclonona[2,3]benz[1,2b]oxet-12-yl ester, β-tert-butyloxycarbonylamino-α-hydroxybenzenepropanoic acid 4,9-bis(acetyloxy)-2-benzoyloxy-1,2,3,4,5,6,7,8,10,13,14-undecahydro-1-hydroxy-7,14,14,17-tetramethyl-8-methoxyimino-1,10-methano-20H-cyclonona[2,3]benz[1,2-b]oxet-12-yl ester, β-tert-butyloxycarbonylamino-α-hydroxybenzenepropanoic acid 4,9-bis(acetyloxy)-2-benzoyloxy-1,2,3,4,5,6,7,8,10,13,14-undecahydro-1-hydroxy-7,14,14,17-tetramethyl-8-methylhydrazinomethyl-1,10-methano-20H-cyclonona[2,3]benz[1,2-b]oxet-12-yl ester, β-terttert-butyloxycarbonylamino-α-hydroxybenzenepropanoic acid 4,9-bis(acetyloxy)-2-benzoyloxy-8-cyano-1,2,3,4,5,6,7,8,10,13,14-undecahydro-1-hydroxy-7,14,14,17-tetramethyl-1,10-methano-20H-cyclonona[2,3]benz[1,2-b]oxet-12-yl ester, β-tert-butyloxycarbonylamino-α-hydroxybenzenepropanoic acid 4,9-bis(acetyloxy)-2-benzoyloxy-8-(1,3-dioxolane-2-yl)-1,2,3,4,5,6,7,8,10,13,14-undecahydro-1-hydroxy-7,14,14,17-tetramethyl-1,10-methano-20H-cyclonona[2,3]benz[1,2-b]oxet-12-yl ester, β-tert-butyloxycarbonylamino-α-hydroxybenzenepropanoic acid 4,9-bis(acetyloxy)-2-benzoyloxy-8-(tetrahydro-oxazole-2-yl)-1,2,3,4,5,6,7,8,10,13,14-undecahydro-1-hydroxy-7,14,14,17-tetramethyl-1,10-methano-20H-cyclonona[2,3]benz[1,2-b]oxet-12-yl ester, β-tert-butyloxycarbonylamino-α-hydroxybenzenepropanoic acid 4,9-bis(acetyloxy)-2-benzoyloxy-8-(1,3-dithiolane-2-yl)-1,2,3,4,5,6,7,8,10,13,14-undecahydro-1-hydroxy-7,14,14,17otetramethyl-1,10-methano-20H-cyclonona[2,3]benz[1,2-b]oxet-12-yl ester, β-benzoylamino-α-hydroxy-γ-(1-naphthyl)propanoic acid 4,9-bis(acetyloxy)-2-benzoyloxy-1,2,3,4,5,6,7,8,10,13,14-undecahydro-1-hydroxy-8-hydroxymethyl-7,14,14,17-tetramethyl-1,10-methano-20H-cyclonona[2,3]benz[1,2-b]oxet-12-yl ester, β-benzoylamino-α-hydroxy-γ-(2-naphthyl)propanoic acid 4,9-bis(acetyloxy)-2-benzoyloxy-1,2,3,4,5,6,7,8,10,13,14-undecahydro-1-hydroxy-8-hydroxymethyl-7,14,14,17-tetramethyl-1,10-methano-20H-cyclonona[2,3]benz[1,2-b]oxet-12-yl ester, β-benzoylamino-α-hydroxy-γ-(pyridyl)propanoic acid 4,9-bis(acetyloxy)-2-benzoyloxy-1,2,3,4,5,6,7,8,10,13,14-undecahydro-1-hydroxy-8-hydroxymethyl-7,14,14,17-tetramethyl-1, 10-methano-20H-cyclonona[2,3]benz[1,2-b]oxet-12-yl ester, β-tert-benzoylamino-α-hydroxy-γ-(thienyl)propanoic acid 4,9-bis(acetyloxy)-2-benzoyloxy-1,2,3,4,5,6,7,8,10,13,14-undecahydro-1-hydroxy-8-hydroxymethyl-7,14,14,17-tetramethyl-1,10-methano-20H-cyclonona[2,3]benz[1,2-b]oxet-12-yl ester, β-benzoylamino-α-hydroxy-γ-(furyl)

propanoic acid 4,9-bis(acetyloxy)-2-benzoyloxyo 1,2,3,4,5,6,7,8,10,13,14-undecahydro-1-hydroxy-8-hydroxymethyl-7,14,14,17-tetramethyl-1,10-methano-20H-cyclonona[2,3]benz[1,2-b]oxet-12-yl ester, β-benzoylamino-α-hydroxy-γ-(oxazolyl)propanoic acid 4,9-bis(acetyloxy)-2-benzoyloxy-1,2,3,4,5,6,7,8,10,13,14-undecahydro-1-hydroxy-8-hydroxymethyl-7,14,14,17-tetramethyl-1,10-methano-20H-cyclonona[2,3]benz[1,2-b]oxet-12-yl ester, β-benzoylamino-α-hydroxy-γ-(imidazolyl)propanoic acid 4,9-bis(acetyloxy)-2-benzoyloxy-1,2,3,4,5,6,7,8,10,13,14-undecahydro-1-hydroxy-8-hydroxymethyl-7,14,14,17-tetramethyl-1,10-methano-20H-cyclonona[2,3]benz[1,2-b]oxet-12-yl ester, β-benzoylamino-α-hydroxy-γ-(pyrazinyl)propanoic acid 4,9-bis(acetyloxy)-2-benzoyloxy-1,2,3,4,5,6,7,8,10,13,14-undecahydro-1-hydroxy-8-hydroxymethyl-7,14,14,17-tetramethyl-1,10-methano-20H-cyclonona[2,3]benz[1,2-b]oxet-12-yl ester, β-benzoylamino-α-hydroxy-γ-(pyridazinyl)propanoic acid 4,9-bis(acetyloxy)-2-benzoyloxy-1,2,3,4,5,6,7,8,10,13,14-undecahydro-1-hydroxy-8-hydroxymethyl-7,14,14,17-tetramethyl-1,10-methano-20H-cyclonona[2,3]benz[1,2-b]oxet-12-yl ester.

In certain embodiments, the paclitaxel derivative inhibits adhesion between the device and a host into which the device is implanted. In certain embodiments, the device delivers the paclitaxel derivative locally to tissue proximate to the device.

In certain embodiments, the device further comprises a coating, wherein the coating comprises the paclitaxel derivative. In certain embodiments, the coating is disposed on a surface of the device. In certain embodiments, the coating directly contacts the device. In certain other devices, the coating indirectly contacts the device. In certain embodiments, the coating partially covers the device. In certain other embodiments, the coating completely covers the device. In certain embodiments, the coating is a uniform coating. In certain other embodiments, the coating is a non-uniform coating. In certain embodiments, the coating is a discontinuous coating. In certain other embodiments, the coating is a patterned coating. In certain embodiments, the coating has a thickness of 100 μm or less. In certain other embodiments, the coating has a thickness of 10 μm or less. In certain embodiments, the coating adheres to the surface of the device upon deployment of the device. In certain embodiments, the coating is stable at room temperature for a period of 1 year. In certain embodiments, the paclitaxel derivative is present in the coating in an amount ranging between about 0.0001% to about 1% by weight. In certain other embodiments, the paclitaxel derivative is present in the coating in an amount ranging between about 1% to about 10% by weight. In yet other embodiments, the paclitaxel derivative is present in the coating in an amount ranging between about 10% to about 25% by weight. In certain other embodiments, the paclitaxel derivative is present in the coating in an amount ranging between about 25% to about 70% by weight. In certain embodiments, the coating further comprises a polymer.

In certain embodiments, the device further comprises a first coating having a first composition and the second coating having a second composition. In certain embodiments, the device further comprises a first coating having a first composition and the second coating having a second composition, wherein the first composition and the second composition are different.

In certain embodiments, the device further comprises a lubricious coating.

In certain embodiments, the device comprises a polymer or polymeric carrier. In certain embodiments, the polymeric carrier comprises a copolymer (e.g., a block copolymer or a random copolymer). In certain embodiments, the polymeric carrier comprises a biodegradable polymer. In certain other embodiments, the polymeric carrier comprises a non-biodegradable polymer. In certain embodiments, the polymeric carrier comprises a hydrophilic polymer. In certain other embodiments, the polymeric carrier comprises a hydrophobic polymer. In certain embodiments, the polymeric carrier comprises a polymer having hydrophilic domains. In certain embodiments, the polymeric carrier comprises a polymer having hydrophobic domains. In certain embodiments, the polymeric carrier comprises a non-conductive polymer. In certain embodiments, the polymeric carrier comprises an elastomer. In certain embodiments, the polymeric carrier comprises a hydrogel. In certain embodiments, the polymeric carrier may comprise a silicone polymer, a hydrocarbon polymer, a styrene-derived polymer, a butadiene polymer, a macromer, a poly(ethylene glycol) polymer, or an amorphous polymer.

In certain embodiments, the paclitaxel derivative is located within pores or holes of the device. In certain other embodiments, the paclitaxel derivative is located within a channel, lumen, or divet of the device.

In certain embodiments, the device further comprises a second pharmaceutically active agent, including an anti-inflammatory agent, an agent that inhibits infection (e.g., an anthracycline, doxorubicin, mitoxantrone, a fluoropyrimidine, 5-fluorouracil (5-FU), a folic acid antagonist, methotrexate, a podophylotoxin, etoposide, a camptothecin, a hydroxyurea, a platinum complex, and cisplatin, an anti-thrombotic agent, a visualization agent (e.g., a radiopaque material comprising a metal, a halogenated compound, or a barium containing compound, a radiopaque material comprising barium, tantalum, or technetium, a MRI responsive material, a visualization agent comprising a gadolinium chelate, a visualization agent comprising iron, magnesium, manganese, copper, or chromium, a visualization agent comprising an iron oxide compound, a visualization agent comprising a dye, pigment, or colorant), or an echogenic material (e.g., in the form of a coating).

In certain embodiments, the device is sterile.

In certain embodiments, the paclitaxel derivative is released into tissue in the vicinity of the device after deployment of the device. In certain embodiments, the tissue may be connective tissue, muscle tissue, nerve tissue, or epithelium tissue.

In certain embodiments, the paclitaxel derivative is released in effective concentrations from the device over a period ranging from the time of deployment of the device to about 1 year, over a period ranging from about 1 month to 6 months, or over a period ranging from about 1-90 days.

In certain embodiments, the paclitaxel derivative is released in effective concentrations from the device at a constant rate. In certain other embodiments, the paclitaxel derivative is released in effective concentrations from the device at an increasing rate. In yet other embodiments, the paclitaxel derivative is released in effective concentrations from the device at a decreasing rate.

Within various embodiments of the invention, the device is further coated with a composition or compound, which delays the onset of activity of the paclitaxel derivative for a period of time after implantation. Representative examples of such agents include heparin, PLGA/MePEG, PLA, and polyethylene glycol. Within further embodiments, the fibrosis-inhibiting implant or device is activated before, during, or after deployment (e.g., an inactive agent on the device is first activated to one that reduces or inhibits an in vivo fibrotic reaction).

In certain embodiments, the paclitaxel derivative is released in effective concentrations from the composition comprising the paclitaxel derivative by diffusion over a period ranging from the time of deployment of the device to about 90 days. In certain other embodiments, the paclitaxel derivative is released in effective concentrations from the composition comprising the paclitaxel derivative by erosion of the composition over a period ranging from the time of deployment of the device to about 90 days.

In certain embodiments, the device may comprise about 0.01 μg to about 10 μg, about 10 μg to about 10 mg, about 10 mg to about 250 mg, about 250 mg to about 1000 mg, or about 1000 mg to about 2500 mg of the paclitaxel derivative.

In certain embodiments, a surface of the device comprises less than 0.01 μg, about 0.01 μg to about 1 μg, about 1 μg to about 10 μg, about 10 μg to about 250 μg, about 250 μg to about 1000 μg, or about 1000 μg to about 2500 μg of the paclitaxel derivative per $mm^2$ of device surface to which the paclitaxel derivative is applied.

In certain embodiments, the stent may be a vascular stent, a coronary stent, a peripheral stent, a covered stent, a gastrointestinal stent, an esophageal stent, a biliary stent, a colonic stent, a tracheal or bronchial stent, a genital-urinary stent, a nasal or sinus stent, or an ENT stent.

The present invention provides combinations of each of medical devices (e.g., various types of stents) disclosed herein with each of paclitaxel derivatives disclosed herein. In addition, for each combination, the paclitaxel derivative may be present in a composition along with one of polymers disclosed herein.

Within yet other aspects of the present invention, methods are provided for manufacturing a medical device, comprising the step of coating (e.g., spraying, dipping, wrapping, or administering drug through) a stent. Additionally, the implant or medical device can be constructed so that the stent itself is comprised of materials that comprise a paclitaxol derivative. A wide variety of stent devices may be utilized within the context of the present invention, depending on the site and nature of treatment desired.

Also provided by the present invention are methods for treating patients undergoing surgical, endoscopic or minimally invasive therapies where a medical device or implant is placed as part of the procedure. As utilized herein, it should be understood that "inhibits fibrosis or stenosis" refers to a statistically significant decrease in the amount of scar tissue in or around the device or an improvement in the luminal area of the device/implant, which may or may not result in a permanent prohibition of any complications or failures of the device/implant.

In one aspect, the present invention provides methods for inhibiting fibrosis comprising placing a medical device that is coated or otherwise contains a paclitaxel derivative or a composition comprising a paclitaxel derivative. Paclitaxel derivatives and compositions comprising paclitaxel derivatives contained in medical devices reduce the foreign body response to implantation of the medical devices and limit the growth of reactive tissue on the surface of, or around in the tissue surrounding the devices, such that performance is enhanced. In many instances, the devices are used to maintain body lumens or passageways such as blood vessels, the gastrointestinal tract, the male and female reproductive tract, the urinary tract, bony foramena (e.g., sinuses, spinal nerve root canals, lacrimal ducts, Eustachian tubes, the auditory canal), and the respiratory tract, where obstruction of the device by scar tissue in the post-procedural period leads to the adverse clinical sequela or failure of the intervention. Medical devices coated with, or otherwise containing, paclitaxel derivatives designed to prevent scar tissue overgrowth and preserve patency can offer significant clinical advantages over uncoated devices.

In another aspect, the present invention is directed to methods for inhibiting fibrosis wherein a medical device and at least one of (i) a paclitaxel derivative and (ii) a composition that comprises a paclitaxel derivative are separately placed or applied into an animal, and the paclitaxel derivative inhibits fibrosis that can otherwise occur at or near the tissue where the medical device is placed. The medical device may be placed .into an animal prior to, simultaneously, or subsequent to, the application of a paclitaxel derivative (or a composition comprising a paclitaxel derivative) to the site where the medical device has been, is being, or is to be, inserted.

These and other aspects of the present invention will become evident upon reference to the following detailed description and attached drawings. In addition, various references are set forth herein which describe in more detail certain procedures and/or compositions (e.g., polymers), and are therefore incorporated by reference in the entirety.

DETAILED DESCRIPTION OF THE INVENTION

Definitions

Figure 1:
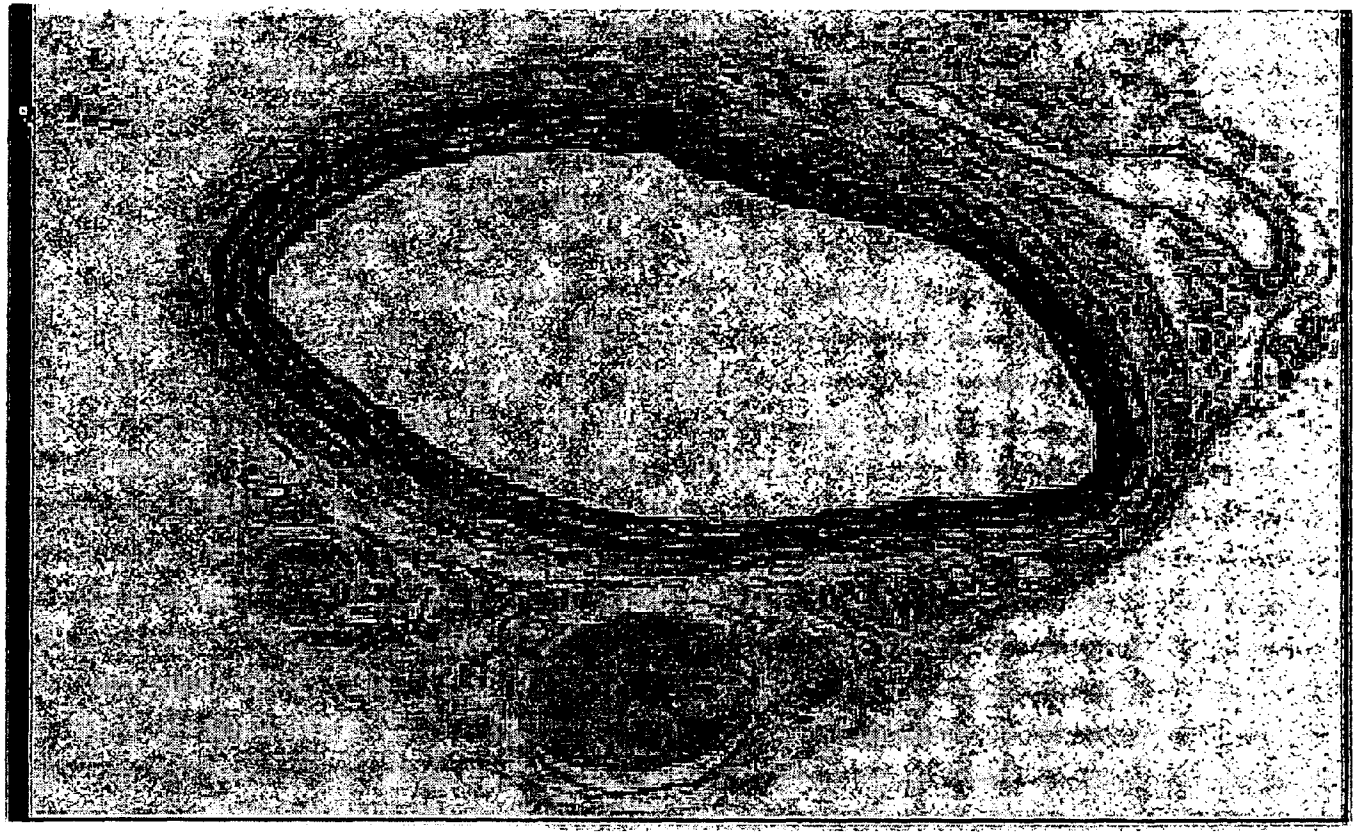
FIG. 1 is a picture that shows an uninjured carotid artery from a rat balloon injury model.

Prior to setting forth the invention, it may be helpful to an understanding thereof to first set forth definitions of certain terms that are used herein.

"Fibrosis," "Scarring," or "Fibrotic Response" refers to the formation of fibrous tissue in response to injury or medical intervention. Therapeutic agents which inhibit fibrosis or scarring (e.g., paclitaxel derivatives) are those agents inhibit fibrosis through one or more mechanisms including: inhibiting angiogenesis, inhibiting migration or proliferation of connective tissue cells (such as fibroblasts, smooth muscle cells, vascular smooth muscle cells), reducing ECM production, and/or inhibiting tissue remodeling.

"Host," "Person," "Subject," "Patient" and the like are used synonymously to refer to the living being into which a device of the present invention is implanted.

"Implanted" refers to having completely or partially placed a device within a host. A device is partially implanted when some of the device reaches, or extends to the outside of, a host.

"Inhibit fibrosis," "reduce fibrosis" and the like are used synonymously to refer to the action of agents or compositions which result in a statistically significant decrease in the formation of fibrous tissue that can be expected to occur in the absence of the agent or composition.

"Medical device," "implant," "medical device or implant," "Implant/device," and the like are used synonymously to refer to any object that is designed to be placed partially or wholly within a patient's body for one or more therapeutic or prophylactic purposes such as for restoring physiological function, alleviating symptoms associated with disease, delivering therapeutic agents, and/or repairing or replacing or augmenting etc. damaged or diseased organs and tissues. While normally composed of biologically compatible synthetic materials (e.g., medical-grade stainless steel, titanium and other metals; polymers such as polyurethane, silicon, PLA, PLGA and other materials) that are exogenous, some medical devices and implants include materials derived from animals (e.g., "xenografts" such as whole animal organs; animal tissues such as heart valves; naturally occurring or chemically-modified molecules such as collagen, hyaluronic acid, proteins, carbohydrates and others), human donors (e.g., "allografts" such as whole organs; tissues such as bone grafts, skin grafts and others), or from the patients themselves (e.g., "autografts" such as saphenous vein grafts, skin grafts, tendon/ligament/muscle transplants). Medical devices of particular utility in the present invention include, but are not restricted to, vascular stents, gastrointestinal stents, tracheal/bronchial stents, genital-urinary stents, and ENT stents.

"Release of an agent" refers to a statistically significant presence of the agent, or a subcomponent thereof, which has disassociated from the implant/device.

"Biodegradable" refers to materials for which the degradation process is at least partially mediated by, and/or performed in, a biological system. "Degradation" refers to a chain scission process by which a polymer chain is cleaved into oligomers and monomers. Chain scission may occur through various mechanisms, including, for example, by chemical reaction (e.g., hydrolysis) or by a thermal or photolytic process. Polymer degradation may be characterized, for example, using gel permeation chromatography (GPC), which monitors the polymer molecular mass changes during erosion and drug release. "Biodegradable" also refers to materials may be degraded by an erosion process mediated by, and/or performed in, a biological system. "Erosion" refers to a process in which material is lost from the bulk. In the case of a polymeric system, the material may be a monomer, an oligomer, a part of a polymer backbone, or a part of the polymer bulk. Erosion includes (i) surface erosion, in which erosion affects only the surface and not the inner parts of a matrix; and (ii) bulk erosion, in which the entire system is rapidly hydrated and polymer chains are cleaved throughout the matrix. Depending on the type of polymer, erosion generally occurs by one of three basic mechanisms (see, e.g., Heller, J., *CRC Critical Review in Therapeutic Drug Carrier Systems* (1984), 1(1), 39-90); Siepmann, J. et al., *Adv. Drug Del. Rev.* (2001), 48, 229-247): (1) water-soluble polymers that have been insolubilized by covalent cross-links and that solubilize as the cross-links or the backbone undergo a hydrolytic cleavage; (2) polymers that are initially water insoluble are solubilized by hydrolysis, ionization, or pronation of a pendant group; and (3) hydrophobic polymers are converted to small water-soluble molecules by backbone cleavage. Techniques for characterizing erosion include thermal analysis (e.g., DSC), X-ray diffraction, scanning electron microscopy (SEM), electron paramagnetic resonance spectroscopy (EPR), NMR imaging, and recording mass loss during an erosion experiment. For microspheres, photon correlation spectroscopy (PCS) and other particles size measurement techniques may be applied to monitor the size evolution of erodible devices versus time.

"Body passageway" as used herein refers to any of number of passageways, tubes, pipes, tracts, canals, sinuses or conduits which have an inner lumen and allow the flow of materials within the body. Representative examples of body passageways include arteries and veins, lacrimal ducts, the trachea, bronchi, bronchiole, nasal passages (including the sinuses) and other airways, eustachian tubes, the external auditory canal, the esophagus, the stomach, the duodenum, the small intestine, the large intestine, biliary tracts, the ureter, the bladder, the urethra, the fallopian tubes, uterus, vagina and other passageways of the female reproductive tract, the vas deferens and other passageways of the male reproductive tract.

Any concentration ranges, percentage range, or ratio range recited herein are to be understood to include concentrations, percentages or ratios of any integer within that range and fractions thereof, such as one tenth and one hundredth of an integer, unless otherwise indicated. Also, any number range recited herein relating to any physical feature, such as polymer subunits, size or thickness, are to be understood to include any integer within the recited range, unless otherwise indicated. It should be understood that the terms "a" and "an" as used above and elsewhere herein refer to "one or more" of the enumerated components. For example, "a" polymer refers to both one polymer and a mixture comprising two or more polymers. As used herein, the term "about" means ±15%.

As discussed above, the present invention provides compositions, methods and devices, which greatly increase the ability to inhibit the formation of reactive scar tissue on, or around, the surface of the device. Described in more detail below are methods for constructing medical implants, compositions and methods for generating medical implants which inhibit fibrosis, and methods for utilizing such medical implants.

A. Stents

In one aspect, the present invention provides medical implants that comprise a stent device and a paclitaxel derivative or a composition comprising a paclitaxel derivative, wherein the paclitaxel derivative inhibits scarring between the stent device and the host into which the device is implanted. In certain aspects, medical implants are provided that include stents which are coated with a paclitaxel derivative or a composition comprising a paclitaxel derivative which inhibits the formation of scar tissue. In another aspect, the stent may be adapted to release a paclitaxel derivative which inhibits the formation of scar tissue.

"Stent" refers to a device comprising a tube (composed of a metal, textile, non-degradable or degradable polymer, and/or other suitable material (such as biological tissue) which maintains flow of a fluid (e.g., blood) from one portion of a body passageway to another. In one aspect, stents are or comprise scaffoldings that are used to treat endoluminal body passageways that have become blocked due to disease or damage, including malignancy or benign disease. In another aspect, the tube has a generally cylindrical shape, such as to create and/or maintain luminal patency of the body passageway. Representative examples of stents, which are described in more detail below, include vascular stents, gastrointestinal stents, tracheal/bronchial stents, genital-urinary stents, and ENT stents.

Intravascular Stents

In one aspect, the present invention provides for the combination of a paclitaxel derivative or a composition comprising a paclitaxel derivative and an intravascular stent.

"Intravascular stent" or "vascular stent" as used herein refers to a stent device that is implanted at least partially within the vasculature (e.g., blood vessels). In one aspect, an intravascular stent is an endovascular scaffolding which maintains the lumen of a body passageway (e.g., an artery) and allows bloodflow. In certain aspects, the intravascular stent may be a "coronary stent" (i.e., a stent that is used in the heart).

In one aspect, intravascular stents may comprise a generally cylindrical tube composed of a metal, textile, non-degradable or degradable polymer, and/or other suitable material (such as biological tissue) which maintains the flow of blood from one portion of a blood vessel to another. Representative examples of intravascular stents that can benefit from being coated with or having incorporated therein a paclitaxel derivative include coronary stents, peripheral stents, and covered stents.

Vascular stents that can be used in the present invention include metallic stents, polymeric stents, biodegradable stents and covered stents. Stents may be self-expandable or balloon-expandable, composed of a variety of metal compounds and/or polymeric materials, fabricated in innumerable designs, used in coronary or peripheral vessels, composed of degradable and/or non-degradable components, fully or partially covered with vascular graft materials (so called "covered stents") or "sleeves", and can be bare metal or drug-eluting.

Stents may comprise a metal or metal alloy such as stainless steel, spring tempered stainless steel, stainless steel alloys, gold, platinum, super elastic alloys, cobalt-chromium alloys and other cobalt-containing alloys (including ELGILOY (Combined Metals of Chicago, Grove Village, IL), PHYNOX (Alloy Wire International, United Kingdom) and CONICHROME (Carpenter Technology Corporation, Wyomissing, PA)), titanium-containing alloys, platinum-tungsten alloys, nickel-containing alloys, nickel-titanium alloys (including nitinol), malleable metals (including tantalum); a composite material or a clad composite material and/or other functionally equivalent materials; and/or a polymeric (non-biodegradable or biodegradable) material. Representative examples of polymers that may be included in the stent construction include polyethylene, polypropylene, polyurethanes, polyesters, such as polyethylene terephthalate (e.g., DACRON or MYLAR (E. I. DuPont De Nemours and Company, Wilmington, DE)), polyamides, polyaramids (e.g., KEVLAR from E. I. DuPont De Nemours and Company), polyfluorocarbons such as poly (tetrafluoroethylene with and without copolymerized hexafluoropropylene) (available, e.g., under the trade name TEFLON (E. I. DuPont De Nemours and Company)), silk, as well as the mixtures, blends and copolymers of these polymers. Stents also may be made with engineering plastics, such as thermotropic liquid crystal polymers (LCP), such as those formed from p,p'-dihydroxy-polynuclear-aromatics or dicarboxy-polynuclear-aromatics.

Further types of stents that can be used with the described therapeutic agents are described, e.g., in PCT Publication No. WO 01/01957 and U.S. Pat. Nos. 6,165,210; 6,099,561; 6,071,305; 6,063,101; 5,997,468; 5,980,551; 5,980,566; 5,972,027; 5,968,092; 5,951,586; 5,893,840; 5,891,108; 5,851,231; 5,843,172; 5,837,008; 5,766,237; 5,769,883; 5,735,811; 5,700,286; 5,683,448; 5,679,400; 5,665,115; 5,649,977; 5,637,113; 5,591,227; 5,551,954; 5,545,208; 5,500,013; 5,464,450; 5,419,760; 5,411,550; 5,342,348; 5,286,254; and 5,163,952. Removable drug-eluting stents are described, e.g., in Lambert, T. (1993) J. Am. Coli. Cardiol.: 21: 483A. Moreover, the stent may be adapted to release the desired agent at only the distal ends, or along the entire body of the stent.

Balloon over stent devices, such as are described in Wilensky, R.L. (1993) J. Am. Coll. Cardiol.: 21: 185A, also are suitable for local delivery of a fibrosing agent to a treatment site.

In addition to using the more traditional stents, stents that are specifically designed for drug delivery can be used. Examples of these specialized drug delivery stents as well as traditional stents include those from Conor Medsystems (Palo Alto, CA) (e.g., U.S. Pat. Nos. 6,527,799; 6,293,967; 6,290,673; 6,241,762; U.S. patent application Publication Nos. 2003/0199970 and 2003/0167085; and PCT Publication No. WO 03/015664).

Examples of intravascular stents, which may be combined with one or more therapeutic agents according to the present invention, include commercially available products. The stent may be self-expanding or balloon expandable (e.g., STRECKER stent by Medi-Tech/Boston Scientific Corporation), or implanted by a change in temperature (e.g., nitinol stent). Self-expanding stents that can be used include the coronary WALLSTENT and the SCIMED RADIUS stent from Boston Scientific Corporation (Natick, Mass.) and the GIANTURCO stents from Cook Group, Inc. (Bloomington, Ind.). Examples of balloon expandable stents that can be used include the CROSSFLEX stent, BX-VELOCITY stent and the PALMAZ-SCHATZ crown and spiral stents from Cordis Corporation (Miami Lakes, Fla.), the V-FLEX PLUS stent by Cook Group, Inc., the NIR, EXPRESS and LIBRERTE stents from Boston Scientific Corporation, the ACS MULTI LINK, MULTI LINK PENTA, SPIRIT, and CHAMPION stents from Guidant Corporation, and the Coronary Stent S670 and S7 by Medtronic, Inc. (Minneapolis, Minn.).

Other examples of stents that can be combined with a fibrosing agent in accordance with the invention include those from Boston Scientific Corporation, (e.g., the drug-eluting TAXUS EXPRESS$^2$ Paclitaxei-Eiuting Coronary Stent System; over the wire stents such as the Express$^2$ Coronary Stent System and NIR Elite OTW Stent System; rapid exchange stents such as the EXPRESS$^2$ Coronary Stent System and the NIR ELITE MONORAIL Stent System; and self-expanding stents such as the MAGIC WALLSTENT Stent System and RADIUS Self Expanding Stent); Medtronic, Inc. (Minneapolis, Minn.) (e.g., DRIVER ABT578-eluting stent, DRIVER ZIPPER MX MultiExchange Coronary Stent System and the DRIVER Over-the- Wire Coronary Stent System; the S7 ZIPPER MX Multi-Exchange Coronary Stent System; S7, S670, S660, and BESTENT2 with Discrete Technology Over-the-Wire Coronary Stent System); Guidant Corporation (e.g., cobalt chromium stents such as the MULTI-LINK VISION Coronary Stent System; MULTI-LINK ZETA Coronary Stent System; MULTI-LINK PIXEL Coronary Stent System; MULTI-LINK ULTRA Coronary Stent System; and the MULTI-LINK FRONTIER); Johnson & Johnson/Cordis Corporation (e.g., CYPHER sirolimus-eluting Stent; PALMAZ-SCHATZ Balloon Expandable Stent; and S.M.A.R.T. Stents); Abbott Vascular (Redwood City, Calif.) (e.g., MATRIX LO Stent; TRIMAXX Stent; and DEXAMET stent); Goner Medsystems (Menlo Park, Calif.) (e.g., MED-STENT and COSTAR stent); AMG GmbH (Germany) (e.g., PICO Elite stent); Biosensors International (Singapore) (e.g., MATRIX stent, CHAMPION Stent (formerly the S-STENT), and CHALLENGE Stent); Biotronik (Switzerland) (e.g., MAGIC AMS stent); Clearstream Technologies (Ireland) (e.g., CLEARFLEX stent); Cook Inc. (Bloomington, Ind.) (e.g., V-FLEX PLUS stent, ZILVER PTX self-expanding vascular stent coating, LOGIX PTX stent (in development); Devax (e.g., AXXESS stent) (Irvine, CA); DISA Vascular (Pty) Ltd (South Africa) (e.g., CHROMOFLEX Stent, S-FLEX Stent, S-FLEX Micro Stent, and TAXOCHROME DES); Intek Technology (Baar, Switzerland) (e.g., APOLLO stent); Orbus Medical Technologies (Hoevelaken, The Netherlands) (e.g., GENOUS); Sorin Biomedica (Saluggia, Italy) (e.g., JANUS and CARBOSTENT); and stents from Bard/Angiomed GmbH Medizintechnik KG (Murray Hill, N.J.), and Blue Medical Supply & Equipment (Mariettta, Ga.), Aachen Resonance GmbH (Germany); Eucatech AG (Germany), Eurocor GmbH (Bonn, Germany), Prot, Goodman, Terumo (Japan), Translumina GmbH (Germany), MIV Therapeutics (Canada), Occam International B.V. (Eindhoven, The Netherlands), Sahajanand Medical Technologies PVT LTD. (India); AVI Biopharma/Medtronic/ Interventional Technologies (Portland, Ore.) (e.g., RESTEN NG-coated stent); and Jomed (e.g., FLEXMASTER drug-eluting stent) (Sweden).

Gastrointestinal Stents

In another aspect, the present invention provides for the combination of a paclitaxel derivative and a gastrointestinal (GI) stent. Gastrointestinal stent devices may be positioned in various parts of the gastrointestinal tract including the biliary duct, pancreatic duct, colon, and the esophagus. GI stents are or comprise scaffoldings that are used to treat endoluminal body passageways (e.g., esophagus, colon, bile duct, pancreatic duct, and the like) that have become blocked due to disease or damage, including malignancy or benign disease.

In one aspect, the GI stent may be an esophageal stent used to keep the esophagus open whereby food is able to travel from the mouth to the stomach. For example, the esophageal stent may be composed of a cylindrical supporting mesh inner layer, retaining mesh outer layer and a semi-permeable membrane sandwiched between. See, e.g., U.S. Pat. No. 6,146,416. The esophageal stent may be a radially, self-expanding stent of open weave construction with an elastomeric film formed along the stent to prevent tissue ingrowth and distal cuffs that resist stent migration. See, e.g., U.S. Pat. No. 5,876,448. The esophageal stent may be composed of a flexible wire configuration to form a cylindrical tube with a deformed end portion increased to a larger diameter for anchoring pressure. See, e.g., U.S. Pat. No. 5,876,445. The esophageal stent may be a flexible, self-expandable tubular wall incorporating at least one truncated conical segment along the longitudinal axis. See, e.g., U.S. Pat. No. 6,533,810.

In another aspect, the Gl stent may be a biliary stent used to keep the biliary duct open whereby bile is able to drain into the small intestines. For example, the biliary stent may be composed of shape memory alloy. See, e.g., U.S. Pat. No. 5,466,242. The biliary stent may be a plurality of radially extending wings with grooves which project from a helical core. See, e.g., U.S. Pat. Nos. 5,776,160 and 5,486,191.

In another aspect, the GI stent may be a colonic stent. For example, the colonic stent may be a hollow tubular body that may expand radially and be secured to the inner wall of the organ in a release fitting. See, e.g., European Patent Application No. EP1092400A2.

In another aspect, the GI stent may be a pancreatic stent used to keep the pancreatic duct open to facilitate secretion into the small intestines. For example, the pancreatic stent may be composed of a soft biocompatible material which is resiliently compliant which conforms to the duct's curvature and contains perforations that facilitates drainage. See, e.g., U.S. Pat. No. 6,132,471.

GI stents, which may be combined with one or more drugs according to the present invention, include commercially available products, such as the NIR Biliary Stent System and the WALLSTENT Endoprostheses from Boston Scientific Corporation.

Tracheal and Bronchial Stents

In another aspect, the present invention provides for the combination of a paclitaxel derivative and a tracheal or bronchial stent device.

Representative examples of tracheal or bronchial stents that can benefit from being coated with or having incorporated therein a paclitaxel derivative include metallic and polymeric tracheal or bronchial stents and tracheal or bronchial stents that have an external covering (e.g., polyurethane, poly(ethylene terephthalate), PTFE, or silicone rubber).

Tracheal and bronchial stents may be, for example, composed of an elastic plastic shaft with metal clasps that expands to form a lumen along the axis for opening the diseased portion of the trachea and having three sections to emulate the natural shape of the trachea. See, e.g., U.S. Pat. No. 5,480,431. The tracheal/bronchial stent may be a T-shaped tube having a tracheotomy tubular portion that projects outwardly through a tracheotomy orifice which is configured to close and form a fluid seal. See, e.g., U.S. Pat. Nos. 5,184,610 and 3,721,233. The tracheal/bronchial stent may be composed of a flexible, synthetic polymeric resin with a tracheotomy tube mounted on the wall with a bifurcated bronchial end that is configured in a T-Y shape with specific curves at the intersections to minimize tissue damage. See, e.g., U.S. Pat. No. 4,795,465. The tracheal/bronchial stent may be a scaffolding configured to be substantially cylindrical with a shape-memory frame having geometrical patterns and having a coating of sufficient thickness to prevent epithelialization. See, e.g., U.S. patent application Publication No. 2003/0024534A1.

Tracheal and bronchial stents, which may be combined with one or more agents according to the present invention, include commercially available products, such as the WALLSTENT Tracheobronchial Endoprostheses and ULTRAFLEX Tracheobronchial Stent Systems from Boston Scientific Corporation and the DUMON Tracheobronchial Silicone Stents from Bryan Corporation (Woburn, Mass.).

Genital-Urinary Stents

In another aspect, the present invention provides for the combination of a paclitaxel derivative and genital-urinary (GU) stent device.

Representative examples genital-urinary (GU) stents that can benefit from being coated with or having incorporated therein, a paclitaxel derivative include ureteric and urethral stents, fallopian tube stents, prostate stents, including metallic and polymeric GU stents and GU stents that have an external covering (e.g., polyurethane, poly(ethylene terephthalate), PTFE or silicone rubber).

In one aspect, genital-urinary stents include ureteric and urethral stents. Ureteral stents are hollow tubes with holes along the sides and coils at either end to prevent migration. Ureteral stents are used to relieve obstructions (caused by stones or malignancy), to facilitate the passage of stones, or to allow healing of ureteral anastomoses or leaks following surgery or trauma. They are placed endoscopically via the bladder or percutaneously via the kidney.

Urethral stents are used for the treatment of recurrent urethral strictures, detruso-external sphincter dyssynergia and bladder outlet obstruction due to benign prostatic hypertrophy. In addition, procedures that are conducted for the prostate, such as external radiation or brachytherapy, may lead to fibrosis due to tissue insult resulting from these procedures. The incidence of urethral stricture in prostate cancer patients treated with external beam radiation is about 2%. Development of urethral stricture may also occur in other conditions such as following urinary catheterization or surgery, which results in damage to the epithelium of the urethra. The clinical manifestation of urinary tract obstruction includes decreased force and caliber of the urinary stream, intermittency, postvoid dribbling, hesitance and nocturia. Complete closure of the urethra can result in numerous problems including eventual kidney failure. To maintain patency in the urethra, urethral stents may be used. The stents are typically self-expanding and composed of metal superalloy, titanium, stainless steel or polyurethane.

For example, the ureteric/urethral stent may be composed of a main catheter body of flexible polymeric material having an enlarged entry end with a hydrophilic tip that dissolves when contacted with body fluids. See, e.g., U.S. Pat. No. 5,401,257. The ureteric/urethral stent may be composed of a multi-sections including a closed section at that the bladder end which does not contain any fluid passageways such that it acts as an anti-reflux device to prevent reflux of urine back into the kidney. See, e.g., U.S. Pat. No. 5,647,843. The ureteric/urethral stent may be composed of a central catheter tube made of shape memory material that forms a stent with a retention coil for anchoring to the ureter. See, e.g., U.S. Pat. No. 5,681,274. The ureteric/urethral stent may be a composed of an elongated flexible tubular stent with preformed set curls at both ends and an elongated tubular rigid extension attached to the distal end which allows the combination function as an externalized ureteral catheter. See, e.g., U.S. Pat. Nos. 5,221,253 and 5,116,309. The ureteric/urethral stent may be composed of an elongated member, a proximal retention structure, and a resilient portion connecting them together, whereby they are all in fluid communication with each other with a slideable portion providing a retracted and expanded position. See, e.g., U.S. Pat. No. 6,685,744. The ureteric/urethral stent may be a hollow cylindrical tube that has a flexible connecting means and locating means that expands and selectively contracts. See, e.g., U.S. Pat. No. 5,322,501. The ureteric/urethral stent may be composed of a stiff polymeric body that affords superior columnar and axial strength for advancement into the ureter, and a softer bladder coil portion for reducing the risk of irritation. See, e.g., U.S. Pat. No. 5,141,502. The ureteric/urethral stent may be composed of an elongated tubular segment that has a pliable wall at the proximal region and a plurality of members that prevent blockage of fluid drainage upon compression. See, e.g., U.S. Pat. No. 6,676,623. The ureteric/urethral stent may be a catheter composed of a conduit which is part of an assembly that allows for non-contaminated insertion into a urinary canal by providing a sealing member that surrounds the catheter during dismantling. See, e.g., U.S. Patent Application Publication No. 2003/0060807A1.

In another aspect, genital-urinary stents include prostatic stents. For example, the prostatic stent may be composed of two polymeric rings constructed of tubing with a plurality of connecting arm members connecting the rings in a parallel manner. See, e.g., U.S. Pat. No. 5,269,802. The prostatic stent may be composed of thermoplastic material and a circumferential reinforcing helical spring, which provides rigid mechanical support while being flexible to accommodate the natural anatomical bend of the prostatic urethra. See, e.g., U.S. Pat. No. 5,069,169.

In another aspect, genital-urinary stents include fallopian stents and other female genital-urinary devices. For example, the genital-urinary device may be a female urinary incontinence device composed of a vaginal-insertable supporting portion that is resilient and flexible, which is capable of self-support by expansion against the vaginal wall and extending about the urethral orifice. See, e.g., U.S. Pat. No. 3,661,155. The genital-urinary device may be a urinary evacuation device composed of an ovular bulbous concave wall having an opening to a body engaging perimetal edge integral with the wall and an attached tubular member with a pleated body. See, e.g., U.S. Pat. No. 6,041,448.

Genital-urinary stents, which may be combined with one or more agents according to the present invention, include commercially available products, such as the UROLUME Endoprosthesis Stents from American Medical Systems, Inc. (Minnetonka, Minn.), the RELIEVE Prostatic/Urethral Endoscopic Device from InjecTx, Inc. (San Jose, Calif.), the PERCUFLEX Ureteral Stents from Boston Scientific Corporation, and the TARKINGTON Urethral Stents and FIRLIT-KLUGE Urethral Stents from Cook Group Inc (Bloomington, Ind.).

Ear and Nose Stents

The present invention provides for the combination of a paclitaxel derivative and an ear-nose-throat (ENT) stent device (e.g., a lacrimal duct stent, Eustachian tube stent, nasal stent, or sinus stent).

The sinuses are four pairs of hollow regions contained in the bones of the skull named after the bones in which they are located (ethmoid, maxillary, frontal and sphenoid). All are lined by respiratory mucosa which is directly attached to the bone. Following an inflammatory insult such as an upper respiratory tract infection or allergic rhinitis, a purulent form of sinusitis can develop. Occasionally secretions can be retained in the sinus due to altered ciliary function or obstruction of the opening (ostea) that drains the sinus. Incomplete drainage makes the sinus prone to infection typically with *Haemophilus influenza, Streptococcus pneumoniae, Moraxella catarrhalis, Veillonella, Peptococcus, Corynebacterium* acnes and certain species of fungi.

When initial treatment such as antibiotics, intranasal steroid sprays and decongestants are ineffective, it may become necessary to perform surgical drainage of the infected sinus. Surgical therapy often involves debridement of the ostea to remove anatomic obstructions and removal of parts of the mucosa. Occasionally a stent (a cylindrical tube which physically holds the lumen of the ostea open) is left in the osta to ensure drainage is maintained even in the presence of postoperative swelling. ENT stents, typically made of stainless steel or plastic, remain in place for several days or several weeks before being removed.

Representative examples of ENT stents that can benefit from being coated with or having incorporated therein a paclitaxel derivative include lacrimal duct stents, Eustachian tube stents, nasal stents, and sinus stents.

In one aspect, the present invention provides for the combination of a lacrimal duct stent and a paclitaxel derivative or a composition comprising a paclitaxel derivative.

In another aspect, the present invention provides for the combination of a Eustachian tube stent and a paclitaxel derivative or a composition comprising a paclitaxel derivative.

In yet another aspect, the present invention provides for the combination of a sinus stent and a paclitaxel derivative or a composition comprising a paclitaxel derivative. Representative examples of sinus stents include the FREEMAN Frontal Sinus Stent (Head and Neck Surgery Associates, Indianapolis, IN) and the PARRELL Frontal Sinus T-Stent 15-15000.

In yet another aspect, the present invention provides for the combination of a nasal stent and a paclitaxel derivative or a composition comprising a paclitaxel derivative.

The ENT stent may be a choanal atresia stent composed of two long hollow tubes that are bridged by a flexible transverse tube. See, e.g., U.S. Pat. No. 6,606,995. The ENT stent may be an expandable nasal stent for postoperative nasal packing composed of a highly porous, pliable and absorbent foam material capable of expanding outwardly, which has a nonadherent surface. See, e.g., U.S. Pat. No. 5,336,163. The ENT stent may be a nasal stent composed of a deformable cylinder with a breathing passageway that has a smooth outer non-absorbent surface used for packing the nasal cavity following surgery. See, e.g., U.S. Pat. No. 5,601,594. The ENT stent may be a ventilation tube composed of a flexible, plastic, tubular vent with a rectangular flexible flange which is used for the nasal sinuses following endoscopic antrostomy. See, e.g., U.S. Pat. No. 5,246,455. The ENT stent may be a ventilating ear tube composed of a shaft and an extended tab which is used for equalizing the pressure between the middle ear and outer ear. See, e.g., U.S. Pat. No. 6,042,574. The ENT stent may be a middle ear vent tube composed of a non-compressible, tubular base and an eccentric flange. See, e.g., U.S. Pat. No. 5,047,053.

ENT stents, which may be combined with one or more agents according to the present invention, include commercially available products such as the SEPRAGEL stent and SEPRAPACK bioresorbable nasal packing and sinus stent from Genzyme Corporation (Ridgefield, N.J.), MEROGEL Sinus Stents from Medtronic Xomed Surgical Products, Inc. (Jacksonville, Fla.), SINUS-FLEX stents from Optimed (Germany), the OXYCELL nasal sinus stent from GMP Companies Inc., the SURGICELL nasal/sinus stent from Ethicon, Inc., and the RAINS Frontal Sinus Stent (see, U.S. Pat. No. 5,693,065) sold by the Smith & Nephew.

B. Therapeutic Agents

Suitable fibrosis or stenosis-inhibiting paclitaxel derivatives may be readily determined based upon the in vitro and in vivo (animal) models such as those provided in Examples 26-36.

Numerous paclitaxel derivatives may be used to inhibit fibrosis in the vicinity of a stent in accordance with the invention. "Paclitaxel derivatives" as used herein includes compounds that structurally similar to paclitaxel but differ slightly in composition (e.g., one atom or functional group is different, added or removed), compounds that are structurally similar to paclitaxel and either actually or theoretically derivable from paclitaxel, conjugates of paclitaxel (e.g., paclitaxel-PEG, paclitaxel-dextran, and paclitaxel-xylos), inactive forms of paclitaxel that may be converted into an active form of paclitaxel under physiological conditions, solvates (e.g., hydrates or adducts) of paclitaxel, active metabolites of paclitaxel, and salts of paclitaxel.

Paclitaxel is a compound which disrupts mitosis (M-phase) by binding to tubulin to form abnormal mitotic spindles or an analogue or derivative thereof. Briefly, paclitaxel is a highly derivatized diterpenoid (Wani et al, *J. Am. Chem. Soc.* 93:2325, 1971) which has been obtained from the harvested and dried bark of *Taxus brevifolia* (Pacific Yew) and *Taxomyces Andreanae* and *Endophytic Fungus* of the Pacific Yew (Stierle et al., *Science* 60:214-216, 1993).

Paclitaxel and its derivatives are considered to function as cell cycle inhibitors by acting as anti-microtubule agents, and more specifically as a microtubule stabilizer. These compounds have been shown useful in the treatment of proliferative disorders, including: non-small cell (NSC) lung; small cell lung; breast; prostate; cervical; endometrial; head and neck cancers.

Representative examples of paclitaxel derivatives that may be used in combination with stents in accordance with the invention include docetaxol (TAXOTERE from Aventis Pharmaceuticals, France), 10-desacetyl analogues of paclitaxel and 3'N-desbenzoyl-3'-N-t-butoxy carbonyl analogues of paclitaxel, 7-deoxy-docetaxol, 7,8-cyclopropataxanes, N-substituted 2-azetidones, 6,7-epoxy paclitaxels, 6,7-modified paclitaxels, 10-desacetoxytaxol, 10-deacetyltaxol (from 10-deacetylbaccatin III), phosphonooxy and carbonate derivatives of taxol, taxol 2',7-di(sodium) 1,2-benzenedicarboxylate, 10-desacetoxy-11,12-dihydrotaxol-10,12(18)-diene derivatives, 10-desacetoxytaxol, protaxol (2'-and/or 7-O-ester derivatives), (2'-and/or 7-O-carbonate derivatives), asymmetric synthesis of taxol side chain, fluoro taxols, 9-deoxotaxane, N-debenzoyl-N-tert-(butoxycaronyl)-10-deacetyltaxol, 13-acetyl-9-deoxobaccatine III, derivatives containing hydrogen or acetyl group and a hydroxy and tert-butoxycarbonylamino, sulfonated 2'-acryloyltaxol and sulfonated 2'-O-acyl acid taxol derivatives, succinyltaxol, 2'-γ-aminobutyryltaxol formate, 2'-acetyl taxol, 7-acetyl taxol, 7-glycine carbamate taxol, 2'-OH-7-PEG(5000) carbamate taxol, 2'-benzoyl and 2',7-dibenzoyl taxol derivatives, other prodrugs (2'-acetyltaxol; 2',7-diacetyltaxol; 2'-succinyltaxol; 2'-(beta-alanyl)-taxol); 2'-gamma-aminobutyryltaxol formate; ethylene glycol derivatives of 2'-succinyltaxol; 2'-glutaryltaxol; 2'-(N,N-dimethylglycyl) taxol; 2'-(2-(N,N-dimethylamino) propionyl)taxol; 2'-orthocarboxybenzoyl taxol; 2'-aliphatic carboxylic acid derivatives of taxol, 2'-(N,N-diethylaminopropionyl)taxol, 2'-(N,N-dimethylglycyl)taxol, 7-(N,N-dimethylglycyl)taxol, 2', 7-di-(N,N-dimethylglycyl) taxol, 7-(N,N-diethylaminopropionyl)taxol, 2', 7-di(N,N-diethylaminopropionyl)taxol, 2'-(L-glycyl)taxol, 7-(L-glycyl)taxol, 2', 7-di(L-glycyl)taxol, 2'-(L-alanyl)taxol, 7-(L-alanyl)taxol, 2',7-di(L-alanyl)taxol, 2'-(L-leucyl)taxol, 7-(L-leucyl)taxol, 2',7-di(L-leucyl)taxol, 2'-(L-isoleucyl) taxol, 7-(L-isoleucyl)taxol, 2', 7-di(L-isoleucyl)taxol, 2'-(L-valyl)taxol, 7-(L-valyl)taxol, 2'7-di(L-valyl)taxol, 2'-(L-phenylalanyl)taxol, 7-(L-phenylalanyl)taxol, 2',7-di(L-phenylalanyl)taxol, 2'-(L-prolyl)taxol, 7-(L-prolyl)taxol, 2',7-di(L-prolyl)taxol, 2'-(L-lysyl)taxol, 7-(L-lysyl)taxol, 2', 7-di(L-lysyl)taxol, 2'-(L-glutamyl)taxol, 7-(L-glutamyl) taxol, 2',7-di(L-glutamyl)taxol, 2'-(L-arginyl)taxol, 7-(L-arginyl)taxol, 2',7-di(L-arginyl)taxol, taxol analogues with modified phenylisoserine side chains, debenzoyl-2-acyl paclitaxel derivatives, benzoate paclitaxel derivatives, phosphonooxy and carbonate paclitaxel derivatives, sulfonated 2'-acryloyltaxol; sulfonated 2'-O-acyl acid paclitaxel derivatives, 18-site-substituted paclitaxel derivatives, chlorinated paclitaxel analogues, C4 methoxy ether paclitaxel derivatives, brominated paclitaxel analogues, nitrophenyl paclitaxel, 10-deacetylated substituted paclitaxel derivatives, 2-debenzoyl and-2-acyl paclitaxel derivatives, n-acyl paclitaxel derivatives, 10-deacetylbaccatin III and 7-protected-10-deacetylbaccatin III derivatives from 10-deacetyl taxol A, 10-deacetyl taxol B, and 10-deacetyl taxol, benzoate derivatives of taxol, 2-aroyl-4-acyl paclitaxel analogues, orthro-ester paclitaxel derivatives, 2-aroyl-4-acyl paclitaxel and 1-deoxy paclitaxel and 1-deoxy paclitaxel derivatives, and 3'-desphenyl-3'-(4-ntirophenyl)-N-debenzoyl-N-(t-butoxycarbonyl)-10-deacetyltaxol.

Paclitaxel derivatives for use in combination with a stent include those prepared from 9-deoxygenated taxane compounds having the structure (C1):

(C1)

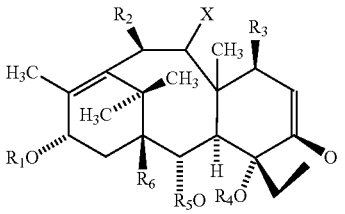

wherein X is be hydrogen (9-deoxy derivatives), thioacyl, or dihydroxyl precursors; $R_1$ is alkanoyl or a radical of the formula (C2)

(C2)

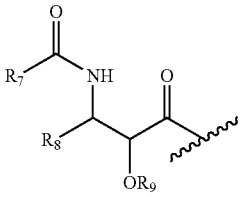

wherein $R_7$ is selected from hydrogen, alkyl, phenyl (substituted or unsubstituted), alkoxy (substituted or unsubstituted), amino (substituted or unsubstituted), phenoxy (substituted or unsubstituted); $R_8$ is selected from hydrogen, alkyl, hydroxyalkyl, alkoxyalkyl, aminoalkyl, phenyl (substituted or unsubstituted), alpha or beta-naphthyl; and $R_9$ is selected from hydrogen, alkanoyl, substituted alkanoyl, and aminoalkanoyl; where substitutions refer to hydroxyl, sulfhydryl, allalkoxyl, carboxyl, halogen, thioalkoxyl, N,N-dimethylamino, alkylamino, dialkylamino, nitro, and —OS)$_3$H, and/or may refer to groups containing such substitutions; $R_2$ is selected from hydrogen or oxygen-containing groups, such as hydroxyl, alkoyl, alkanoyloxy, aminoalkanoyloxy, and peptidyalkanoyloxy; $R_3$ is selected from hydrogen or oxygen-containing groups, such as hydroxyl, alkoyl, alkanoyloxy, aminoalkanoyloxy, and peptidyalkanoyloxy, and may further be a silyl containing group or a sulphur containing group; $R_4$ is selected from acyl, alkyl, alkanoyl, aminoalkanoyl, peptidylalkanoyl and aroyl; $R_5$ is selected from acyl, alkyl, alkanoyl, aminoalkanoyl, peptidylalkanoyl and aroyl; $R_6$ is selected from hydrogen or oxygen-containing groups, such as hydroxyl alkoyl, alkanoyloxy, aminoalkanoyloxy, and peptidyalkanoyloxy (see, e.g., U.S. Pat. No. 5,440,056).

Examples of paclitaxel derivatives prepared from the 9-deoxygenated taxane compounds having the structure (C2) include 9-deoxotaxol, 7-deoxy-9-deoxotaxol, and 10-desacetoxy-7-deoxy-9-deoxotaxol.

In one aspect, the paclitaxel derivative may be a 9-dihydrotaxol derivative having the structure (C3) prepared from 9-dihydro-13-acetylbaccatin III, (C3)

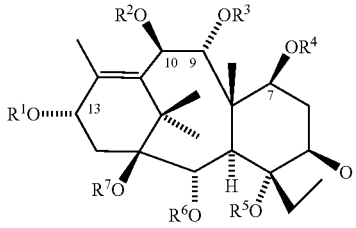

wherein $R^1$ is a group having the formula:

(C4)

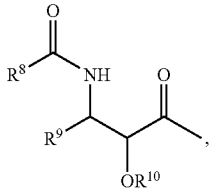

wherein $R^8$ is hydrogen, alkyl, phenyl(substituted or unsubstituted), alkoxy (substituted or unsubstituted), amino (substituted or unsubstituted), or phenoxy (substituted or unsubstituted).

$R^2$, $R^4$, $R^5$ and $R^7$ in structure (C3) are independently hydrogen, alkyl, alkanoyl, or aminoalkanoyl.

$R^3$ in structure (C3) is hydrogen, alkyl, or aminoalkanoyl.

$R^6$ in structure (C3) is hydrogen, alkyl, alkanoyl, aminoalkanoyl, or phenylcarbonyl (—C(O)-phenyl).

Alternatively, $R^3$ in structure (C3), taken together with either $R^2$ or $R^4$, may form a ring having the formula (C5)

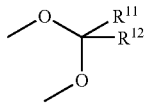

wherein $R^{11}$ and $R^{12}$ are independently hydrogen, alkyl, phenyl or substituted phenyl; or, taken together, $R^{11}$ and $R^{12}$ are a single atom selected from the group consisting of oxygen and sulfur; or one of $R^{11}$ and $R^{12}$ is hydrogen, alkyl, phenyl (substituted or unsubstituted), and the other is —$OR^{13}$ or —$NR^{13}R^{14}$ where $R^{13}$ and $R^{14}$ are independently alkyl, alkanoyl, substituted alkanoyl, phenyl or substituted phenyl.

Examples of paclitaxel derivatives prepared from the compounds having the structure (C3) include 9-dihydrotaxol compounds ($R^3$ of structure C3 is hydrogen).

In one aspect, the paclitaxel derivative is 9-dihydrotaxol ($R^2$ and $R^5$ are acetyl; $R^3$, $R^4$, and $R^7$ are hydrogen, and $R^6$ is phenylcarbonyl).

In another aspect, the 9-dihydrotaxol compound is 2'-O-ethoxyethyl-7-O-trietylsilyl-9-dihydrotaxol.

In another aspect, the 9-dihydrotaxol compound is 2'-O-ethoxyethyl-9-dihydrotaxol.

In another aspect, the 9-dihydrotaxol compound is 10-deacetyl-9-dihydrotaxol.

In another aspect, the 9-dihydrotaxol compound is 9-dihydrotaxol-7,9-isopropylidene ketal.

In another aspect, the 9-dihydrotaxol compound is 9-dihydrotaxol-7,9-propylidene acetal.

In another aspect, the 9-dihydrotaxol compound is 9-dihydrotaxol-7,9-benzylidene acetal.

In another aspect, the 9-dihydrotaxol compound is 9-dihydrotaxol-7,9-(3,4-dihydroxy)butylidene acetal.

In another aspect, the 9-dihydrotaxol compound is 9-dihydrotaxol-7,9-thionocarbonate.

In another aspect, the 9-dihydrotaxol compound is 9-dihydrotaxol-7-O-allyl ether.

In another aspect, the 9-dihydrotaxol compound is 9-dihydrotaxol-7-O-(2,3-dihydroxypropyl) ether.

In another aspect, the 9-dihydrotaxol compound is 9-dihydrotaxol-7-O-(2-dimethylaminoethyl) ether.

In another aspect, the 9-dihydrotaxol compound is 9-dihydrotaxol-7-O-(2-hydroxyethyl) ether.

In another aspect, the 9-dihydrotaxol compound is 9-dihydrotaxol-7-O-(2-acetoxyethyl) ether.

In another aspect, the 9-dihydrotaxol compound is N-debenzoyl-N-t-butoxycarbonyl-9-dihydrotaxol.

In another aspect, the 9-dihydrotaxol compound is 10-deacetyi-N-debenzoyl-N-t-butoxycarbonyl-9-dihydrotaxol.

In another aspect, the 9-dihydrotaxol compound is N-debenzoyl-N-t-butylacetyl-9-dihydrotaxol.

In another aspect, the 9-dihydrotaxol compound is N-debenzoyl-N-isobutoxycarbonyl-9-dihydrotaxol.

In another aspect, the 9-dihydrotaxol compound is N-debenzoyl-N-adamantoxycarbonyl-9-dihydrotaxol.

In another aspect, the 9-dihydrotaxol compound is N-debenzoyl-N-isopropoxycarbonyl-9-dihydrotaxol.

In another aspect, the 9-dihydrotaxol compound is N-debenzoyl-N-benzyloxycarbonyl-9-dihydrotaxol.

In another aspect, the 9-dihydrotaxol compound is N-debenzoyl-9-dihydrotaxol.

In another aspect, the 9-dihydrotaxol compound is N-debenzoyl-N-pivaloyl-9-dihydrotaxol.

In another aspect, the 9-dihydrotaxol compound is N-debenzoyl-N-acetyl-9-dihydrotaxol.

In another aspect, the 9-dihydrotaxol compound is N-debenzoyl-N-t-butylcarbamyl-9-dihydrotaxol.

In another aspect, the paclitaxel derivative may be prepared from a 9-dihydropaclitaxel derivative, such as 9-dihydro-13-acetylbaccatin III (see, e.g., U.S. Pat. No. 5,468,769).

In one aspect, the paclitaxel derivative is 2'-O-(1-ethyoxyethyl)-9-dihydrotaxol.

In one aspect, the paclitaxel derivative is 4,9,12-tris (acetyloxy)-2-benzoyloxy-8-formyl-1,2,3,4,5,6,7,8,10,13, 14-undecahydro-1-hydroxy-7,14,14,17-tetramethyl-1,10-methano-20H-cyclonona[2,3]benz[1,2-b]oxete.

In another aspect, the paclitaxel derivative is β-tert-butyloxycarbonylamino-α-hydroxybenzenepropanoic acid 4,9-bis(acetyloxy)-2-benzoyloxy-8-formyl-1,2,3,4,5,6,7,8, 10,13,14-undecahydro-1-hydroxy-7,14,14,17-tetramethyl-1,10-methano-20H-cyclonona[2,3]benz[1, 2-b]oxet-12-yl ester.

In another aspect, the paclitaxel derivative is β-benzoylamino-α-hydroxybenzenepropanoic acid 4,9-bis (acetyloxy)-2-benzoyloxy-8-formyl-1,2,3,4,5,6,7,8,10,13, 14-undecahydro-1-hydroxy-7,14,14,17-tetramethyl-1,10-methano-20H-cyclonona[2,3]benz[1,2-b]oxet-12-yl ester.

Additional examples of paclitaxel derivatives that may be used in the practice of the invention include the following:

4,9,12(tris(acetyloxy)-2-benzoyloxy-8-formyl-1,2,3,4,5, 6,7,8,10,13,14-undecahydro-1-hydroxy-7,14,14,17-tetramethyl-1,10-methano-20H-cyclonona[2,3]benz[1,2-b] oxete;

4,9,12-tris(acetyloxy)-2-benzoyloxy-1,2,3,4,5,6,7,8,10, 13,14-undecahydro-1-hydroxy-8-hydroxymethyl-7,14,14, 17-tetramethyl-1,10-methano-20H-cyclonona[2,3]benz[1,2-b]oxete;

4,9,12-tris(acetyloxy)-2-benzoyloxy-1,2,3,4,5,6,7,8,10, 13,14-undecahydro-1-hydroxy-8-methoxymethyl-7,14,14, 17-tetramethyl1,10-methano-20H-cyclonona[2,3]benz[1,2-b]oxete;

4,9,12-tris(acetyloxy)-2-benzoyloxy-1,2,3,4,5,6,7,8,10, 13,14-undecahydro-1-hydroxy-8-ethoxymethyl-7,14,14,17-tetramethyl-1,10-methano-20H-cyclonona[2,3]benz[1,2-b] oxete;

4,9,12-tris(acetyloxy)-8-acetyloxymethyl-2-benzoyloxy-1,2,3,4,5,6,7,8,10,13,14-undecahydro-1-hydroxy-7,14,14, 17-tetramethyl-1,10-methano-20H-cyclonona[2,3]benz[1,2-b]oxete;

4,9,12-tris(acetyloxy)-2-benzoyloxy-8-dimethylaminomethyl-1,2,3,4,5,6,7,8,10,13,14-undecahydro-1-hydroxy-7,14,14,17-tetramethyl-1,10-methano-20H-cyclonona[2,3]benz[1,2-b]oxete;

4,9,12-tris(acetyloxy)-2-benzoyloxy-8-diethylaminomethyl-1,2,3,4,5,6,7,8,10,13,14-undecahydro-1-hydroxy-7,14,14,17-tetramethyl-1,10-methano-20H-cyclonona[2,3]benz[1,2-b]oxete;

4,9,12-tris(acetyloxy)-2-benzoyloxy-1,2,3,4,5,6,7,8,10, 13,14-undecahydro-1-hydroxy-7,14,14,17-tetramethyl-8-methylamino-1,10-methano-20H-cyclonona[2,3]benz[1,2-b]oxete;

4,9,12-tris(acetyloxy)-2-benzoyloxy-1,2,3,4,5,6,7,8,10, 13,14-undecahydro-1-hydroxy-7,14,14,17-tetramethyl-8-ethylamino-1,10-methano-20H-cyclonona[2,3]benz[1,2-b] oxete;

4,9,12-tris(acetyloxy)-2-benzoyloxy-1,2,3,4,5,6,7,8,10, 13,14-undecahydro-1-hydroxy-7,14,14,17-tetramethyl-8-methylimino-1,10-methano-20H-cyclonona[2,3]benz[1,2-b] oxete;

4,9,12-tris(acetyloxy)-2-benzoyloxy-1,2,3,4,5,6,7,8,10, 13,14-undecahydro-1-hydroxy-7,14,14,17-tetramethyl-8-methoxyimino-1,10-methano-20H-cyclonona [2,3]benz[1, 2-b]oxete;

4,9,12-tris(acetyloxy)-2-benzoyloxy-1,2,3,4,5,6,7,8,10, 13,14-undecahydro-1-hydroxy-7,14,14,17-tetramethyl-8-methylhydrazinomethyl-1,10-methano-20H-cyclonona[2,3] benz[1,2-b]oxete;

4,9,12-tris(acetyloxy)-2-benzoyloxy-8-cyano-1,2,3,4,5,6, 7,8,10,13,14-undecahydro-1-hydroxy-7,14,14,17-tetramethyl-1,10-methano-20H-cyclonona[2,3]benz[1,2-b] oxete;

4,9,12-tris(acetyloxy)-2-benzoyloxy-1,2,3,4,5,6,7,8,10, 13,14-undecahydro-1-hydroxy-7,14,14,17-tetramethyl-1, 10-methano-20H-cyclonona[2,3]benz[1,2-b]oxete-8-methylsulfate;

4,9,12-tris(acetyloxy)-2-benzoyloxy-1,2,3,4,5,6,7,8,10, 13,14-undecahydro-1-hydroxy-7,14,14,17-tetramethyl-1, 10-methano-20H-cyclonona[2,3]benz[-1,2-b]oxete-8methylphosphate;

4,9,12-tris(acetyloxy)-2-benzoyloxy-8-(1,3-dioxolan-2-yl)-1,2,3,4,5,6,7,8,10,13,14-undecahydro-1-hydroxy-7,14, 14,17-tetramethyl-1,10-methano-20H-cyclonona[2,3]benz [1,2-b]oxete;

4,9,12-tris(acetyloxy)-2-benzoyloxy-8-(tetrahydro-oxazo le-2-yl)-1,2,3,4,5,6,7,8,10,13,14-undecahydro-1-hydroxy-7, 14,14,17-tetramethyl-1,10-methano-20H-cyclonona[2,3] benz[1,2-b]oxete;

4,9,12-tris(acetyloxy)-2-benzoyloxy-8-(1,3-dithiolane-2-yl)-1,2,3,4,5,6,7,8,10,13,14-undecahydro-1-hydroxy-7,14, 14,17-tetramethyl-1,10-methano-20H-cyclonona[2,3]benz [1,2-b]oxete;

4,9-bis(acetyloxy)-2-benzoyloxy-8-formyl-1,12-dihydroxy-1,2,3,4,5,6,7,8,10,13,14-undecahydro-7,14,14,17-tetramethyl-1,10-methano-20H-cyclonona[2,3]benz[1,2-b]oxete;

4,9-bis(acetyloxy)-2-benzoyloxy-1,12-dihydroxy-1,2,3,4,5,6,7,8,10,13,14-undecahydro-8-hydroxymethyl-7,14,14,17-tetramethyl-1,10-methano-20H-cyclonona[2,3]benz[1,2-b]oxete;

4,9-bis(acetyloxy)-2-benzoyloxy-1,12-dihydroxy-1,2,3,4,5,6,7,8,10,13,14-undecahydro-8-methoxymethyl-7,14,14,17-tetramethyl-1,10-methano-20H-cyclonona [2,3]benz[1,2-b]oxete;

4,9-bis(acetyloxy)-2-benzoyloxy-1,12-dihydroxy-1,2,3,4,5,6,7,8,10,13,14-undecahydro-8-ethoxymethyl-7,14,14,17-tetramethyl-1,10-methano-20H-cyclonona[2,3]benz[1,2-b]oxete;

4,9-bis(acetyloxy)-8-acetyloxymethyl-2-benzoyloxy-1,12-dihydroxy-1,2,3,4,5,6,7,8,10,13,14-undecahydro-7,14,14,17-tetramethyl-1,10-methano-20H-cyclonona[2,3]benz[1,2-b]oxete;

4,9-bis(acetyloxy)-2-benzoyloxy-8-dimethylaminomethyl-1,12-dihydroxy-1,2,3,4,5,6,7,8,10,13,14-undecahydro-7,14,14,17-tetramethyl-1,10-methano-20H-cyclonona[2,3]benz[1,2-b]oxete;

4,9-bis(acetyloxy)-2-benzoyloxy-8-diethylaminomethyl-1,12-dihydroxy-1,2,3,4,5,6,7,8,10,13,14-undecahydro-7,14,14,17-tetramethyl-1,10-methano-20H-cyclonona[2,3]benz[1,2-b]oxete;

4,9-bis(acetyloxy)-2-benzoyloxy-1,12-dihydroxy-1,2,3,4,5,6,7,8,10,13,14-1-undecahydro-7,14,14,17-tetramethyl-8-methylamino-1,10-methano-20H-cyclonona[2,3]benz[1,2-b]oxete;

4,9-bis(acetyloxy)-2-benzoyloxy-1,12-dihydroxy-1,2,3,4,5,6,7,8,10,13,14-undecahydro-7,14,14,17-tetramethyl-8-ethylamino-1,10-methano-20H-cyclonona[2,3]benz[1,2-b]oxete;

4,9-bis(acetyloxy)-2-benzoyloxy-1,12-dihydroxy-1,2,3,4,5,6,7,8,10,13,14-undecahydro-7,14,14,17-tetramethyl-8-methylimino-1,10-methano-20H-cyclonona[2,3]benz[1,2-b]oxete;

4,9-bis(acetyloxy)-2-benzoyloxy-1,12-dihydroxy-1,2,3,4,5,6,7,8,10,13,14-undecahydro-7,14,14,17-tetramethyl-8-methoxyimino-1,10-methano-20H-cyclonona[2,3]benz[1,2-b]oxete;

4,9-bis(acetyloxy)-2-benzoyloxy-1,12-dihydroxy-1,2,3,4,5,6,7,8,10,13,14-undecahydro-7,14,14,17-tetramethyl-8-methylhydrazinomethyl-1,10-methano-20H-cyclonona[2,3]benz[1,2-b]oxete;

4,9-bis(acetyloxy)-2-benzoyloxy-8-cyano-1,12-dihydroxy-1,2,3,4,5,6,7,8,10,13,14-undecahydro-7,14,14,17-tetramethyl1-, 10-methano-20H-cyclonona[2,3]benz[1,2-b]oxete;

4,9-bis(acetyloxy)-2-benzoyloxy-1,12-dihydroxy-1,2,3,4,5,6,7,8,10,13,14-undecahydro-7,14,14,17-tetramethyl-1,10-methano-20H-cyclonona[2,3]benz[1,2-b]oxete-8-methylsulfate;

4,9-bis(acetyloxy)-2-benzoyloxy-1,12-dihydroxy-1,2,3,4,5,6,7,8,10,13,14-undecahydro-7,14,14,17-tetramethyl-1,10-methano-20H-cyclonona[2,3]benz[1,2-b]oxete-8-methylphosphate;

4,9-bis(acetyloxy)-2-benzoyloxy-8-(1,3-dioxolan-2-yl)-1,12-dihydroxy-1,2,3,4,5,6,7,8,10,13,14-undecahydro-7,14,14,17-tetramethyl-1,10-methano-20H-cyclonona[2,3]benz[1,2-b]oxete;

4,9-bis(acetyloxy)-2-benzoyloxy-8-(tetrahydro-oxazole-2-yl)-1,12-dihydroxy-1,2,3,4,5,6,7,8,10,13,14-undecahydro-7,14,14,17-tetramethyl-1,10-methano-20H-cyclonona[2,3]benz[1,2-b]oxete;

4,9-bis(acetyloxy)-2-benzoyloxy-8-(1,3-dithiolane-2-yl)-1,12-dihydroxy-1,2,3,4,5,6,7,8,10,13,14-undecahydro-7,14,14,17-tetramethyl-1,10-methano-20H-cyclonona[2,3]benz[1,2-b]oxete;

β-benzoylamino-α-hydroxybenzenepropanoic acid 4,9-bis(acetyloxy)-2-benzoyloxy-1,2,3,4,5,6,7,8,10,13,14-undecahydro-1-hydroxy-8-hydroxymethyl-7,14,14,17-tetramethyl-1,10-methano-20H-cyclonona[2,3]benz[1,2-b]oxet-12-yl ester;

β-benzoylamino-α-hydroxybenzenepropanoic acid 4,9-bis(acetyloxy)-2-benzoyloxy-1,2,3,4,5,6,7,8,10,13,14-undecahydro-1-hydroxy-8-methoxymethyl-7,14,14,17-tetramethyl-1,10-methano-20H-cycionona[2,3]benz[1,2-b]oxet-12-yl ester;

β-benzoylamino-α-hydroxybenzenepropanoic acid 4,9-bis(acetyloxy)-2-benzoyloxy-1,2,3,4,5,6,7,8,10,13,14-undecahydro-1-hydroxy-8-ethoxymethyl-7,14,14,17-tetramethyl-1,10-methano-20H-cyclonona[2,3]benz[1,2-b]oxet-12-yl ester;

β-benzoylamino-α-hydroxybenzenepropanoic acid 4,9-bis(acetyloxy)-8-acetyloxymethyl-2-benzoyloxy-1,2,3,4,5,6,7,8,10,13,14-undecahydro-1-hydroxy-7,14,14,17-tetramethyl-1,10-methano-20H-cyclonona[2,3]benz[1,2-b]oxet-12-yl ester;

β-benzoylamino-α-hydroxybenzenepropanoic acid 4,9-bis(acetyloxy)-2-benzoyloxy-8-dimethylaminomethyl-1,2,3,4,5,6,7,8,10,13,14-undecahydro-1-hydroxy-7,14,14,17-tetramethyl-1,10-methano-20H-cyclonona[2,3]benz[1,2-b]oxet12-yl ester;

β-benzoylamino-α-hydroxybenzenepropanoic acid 4,9-bis(acetyloxy)-2-benzoyloxy-8-diethylaminomethyl-1,2,3,4,5,6,7,8,10,13,14-undecahydro-1-hydroxy-7,14,14,17-tetramethyl-1,10-methano-20H-cyclonona[2,3]benz[1,2-b]oxet12-yl ester;

1,3-benzoylamino-α-hydroxybenzenepropanoic acid 4,9-bis(acetyloxy)-2-benzoyloxy-1,2,3,4,5,6,7,8,10,13,14-undecahydro-1-hydroxy-7,14,14,17-tetramethyl-8-methylaminomethyl-1,10-methano-20H-cyclonona[2,3]benz[1,2-b]oxet-12-yl ester;

β-benzoylamino-α-hydroxybenzenepropanoic acid 4,9-bis(acetyloxy)-2-benzoyloxy-1,2,3,4,5,6,7,8,10,13,14-undecahydro-1-hydroxy-7,14,14,17-tetramethyl-8-methylimino-1,10-methano-20H-cyclonona[2,3]benz[1,2-b]oxet-12-yl ester;

β-benzoylamino-α-hydroxybenzenepropanoic acid 4,9-bis(acetyloxy)-2-benzoyloxy-1,2,3,4,5,6,7,8,10,13,14-undecahydro-1-hydroxy-7,14,14,17-tetramethyl-8-methoxyimino-1,10-methano-20H-cyclonona[2,3]benz[1,2-b]oxet-12yl ester;

β-benzoylamino-α-hydroxybenzenepropanoic acid 4,9-bis(acetyloxy)-2-benzoyloxy-1,2,3,4,5,6,7,8,10,13,14-undecahydro-1-hydroxy-7,14,14,17-tetramethyl-8-methyihydrazinomethyl-1,10-methano-20H-cyclonona[2,3]benz[1,2-b]oxet-12-yl ester;

β-benzoylamino-α-hydroxybenzenepropanoic acid 4,9-bis(acetyloxy)-2-benzoyloxy-8-cyano-1,2,3,4,5,6,7,8,10,13,14-undecahydro-1-hydroxy-7,14,14,17-tetramethyl-1,10-methano-20H-cyclonona[2,3]benz[1,2-b]oxet-12-yl ester;

β-benzoylamino-α-hydroxybenzenepropanoic acid 4,9-bis(acetyloxy)-2-benzoyloxy-8-(1,3-dioxolane-2-yl)-1,2,3,4,5,6,7,8,10,13,14-undecahydro-1-hydroxy-7,14,14,17-tetramethyl-1,10-methano-20H-cyclonona[2,3]benz[1,2-b]oxet12-yl ester;

β-benzoylamino-α-hydroxybenzenepropanoic acid 4,9-bis(acetyloxy)-2-benzoyloxy-8-(tetrahydro-oxazole-2-yl)-1,2,3,4,5,6,7,8,10,13,14-undecahydro-1-hydroxy-7,14,14,17-tetramethyl-1,10-methano-20H-cyclonona[2,3]benz[1,2-b]oxet-12-yl ester;

β-benzoylamino-α-hydroxybenzenepropanoic acid 4,9-bis(acetyloxy)-2-benzoyloxy-8-(1,3-dithiolane-2-yi)-1,2,3,4,5,6,7,8,10,13,14-undecahydro-1-hydroxy-7,14,14,17-tetramethyl-1,10-methano-20H-cyclonona[2,3]benz[1,2-b]oxet-12-yl ester;

β-tert-butyloxycarbonylamino-α-hydroxybenzenepropanoic acid 4,9-bis(acetyloxy)-2-benzoyloxy-8-formyl-1,2,3,4,5,6,7,8,10,13,14-undecahydro-1-hydroxy-7,14,14,17-tetramethyl-1,10-methano-20H-cyclonona[2,3]benz[1,2-b]oxet-12-yl ester;

β-tert-butyloxycarbonylamino-α-hydroxybenzenepropanoic acid 4,9-bis(acetyloxy)-2-benzoyloxy-1,2,3,4,5,6,7,8,10,13,14-undecahydro-1-hydroxy-8-hydroxymethyl-7,14,14,17-tetramethyl-1,10-methano-20H-cyclonona[2,3]benz[1,2b]oxet-12-yl ester;

β-tert-butyloxycarbonylamino-α-hydroxybenzenepropanoic acid 4,9-bis(acetyioxy)-2-benzoyloxy-1,2,3,4,5,6,7,8,10,13,14-undecahydro-1-hydroxy-8-methoxymethyl-7,14,14,17-tetramethyl-1,10-methano-20H-cyclonona[2,3]benz[1,2b]oxet-12-yl ester;

β-tert-butyloxycarbonylamino-α-hydroxybenzenepropanoic acid 4,9-bis(acetyioxy)-2-benzoyloxy-1,2,3,4,5,6,7,8,10,13,14-undecahydro-1-hydroxy-8-ethoxymethyl-7,14,14,17-tetramethyl-1,10-methano-20H-cyclonona[2,3]benz[1,2b]oxet-12-yl ester;

β-tert-butyloxycarbonylamino-α-hydroxybenzenepropanoic acid 4,9-bis(acetyloxy)-8-acetyloxymethyl-2-benzoyloxy-1,2,3,4,5,6,7,8,10,13,14-undecahydro-1-hydroxy-7,14,14,17-tetramethyl-1,10-methano-20H-cyclonona[2,3]benz[1,2-b]oxet-12-yl ester;

β-tert-butyloxycarbonylamino-α-hydroxybenzenepropanoic acid 4,9-bis(acetyloxy)-2-benzoyloxy-8-dimethylaminomethyl-1,2,3,4,5,6,7,8,10,13,14-undecahydro-1-hydroxy-7,14,14,17-tetramethyl-1,10-methano-20H-cyclonona[2,3]benz[1,2-b]oxet-12-yl ester;

β-tert-butyloxycarbonylamino-α-hydroxybenzenepropanoic acid 4,9-bis(acetyloxy)-2-benzoyloxy-8-diethylaminomethyl-1,2,3,4,5,6,7,8,10,13,14-undecahydro-1-hydroxy-7,14,14,17-tetramethyl-1,10-methano-20H-cyclonona [2,3]benz[1,2-b]oxet-12-yl ester;

β-tert-butyloxycarbonylamino-α-hydroxybenzenepropanoic acid 4,9-bis(acetyloxy)-2-benzoyloxy-1,2,3,4,5,6,7,8,10,13,14-undecahydro-1-hydroxy-7,14,14,17-tetramethyl-8-methylaminomethyl-1,10-methano-20H-cyclonona[2,3]benz[1,2-b]oxet-12-yl ester;

β-tert-butyloxycarbonylamino-α-hydroxybenzenepropanoic acid 4,9-bis(acetyloxy)-2-benzoyloxy-1,2,3,4,5,6,7,8,10,13,14-undecahydro-1-hydroxy-7,14,14,17-tetramethyl-8-methylimino-1,10-methano-20H-cyclonona[2,3]benz[1,2b]oxet-12-yl ester;

β-tert-butyloxycarbonylamino-α-hydroxybenzenepropanoic acid 4,9-bis(acetyloxy)-2-benzoyloxy-1,2,3,4,5,6,7,8,10,13,14-undecahydro-1-hydroxy-7,14,14,17-tetramethyl-8-methoxyimino-1,10-methano-20H-cyclonona[2,3]benz[1,2-b)oxet-12-yl ester;

β-tert-butyloxycarbonylamino-α-hydroxybenzenepropanoic acid 4,9-bis(acetyloxy)-2-benzoyloxy-1,2,3,4,5,6,7,8,10,13,14-undecahydro-1-hydroxy-7,14,14,17-tetramethyl-8-methylhydrazinomethyl-1,10-methano-20H-cyclonona[2,3]benz[1,2-b]oxet-12-yl ester;

β-tert-butyloxycarbonylamino-α-hydroxybenzenepropanoic acid 4,9-bis(acetyloxy)-2-benzoyloxy-8-cyano-1,2,3,4,5,6,7,8,10,13,14-undecahydro-1-hydroxy-7,14,14,17-tetramethyl-1,10-methano-20H-cyclonona[2,3]benz[1,2-b]oxet12-yl ester;

β-tert-butyloxycarbonylamino-α-hydroxybenzenepropanoic acid 4,9-bis(acetyloxy)-2-benzoyloxy-8-(1,3-dioxolane-2-yl)-1,2,3,4,5,6,7,8,10,13,14-undecahydro-1-hydroxy-7,14,14,17-tetramethyl-1,10-methano-20H-cyclonona[2,3]benz[1,2-b]oxet-12-yl ester;

β-tert-butyloxycarbonylamino-α-hydroxybenzenepropanoic acid 4,9-bis(acetyloxy)-2-benzoyloxy-8-(tetrahydro-oxazole-2-yl)-1,2,3,4,5,6,7,8,10,13,14-undecahydro-1-hydroxy-7,14,14,17-tetramethyl-1,10-methano-20H-cyclonona[2,3]benz[1,2-b]oxet-12-yl ester;

β-tert-butyloxycarbonylamino-α-hydroxybenzenepropanoic acid 4,9-bis(acetyloxy)-2-benzoyloxy-8-(1,3-dithiolane-2-yl)-1,2,3,4,5,6,7,8,10,13,14-undecahydro-1-hydroxy-7,14,14,17 otetramethyl-1,10-methano-20H-cyclonona(2,3]benz[1,2-b]oxet-12-yl ester;

β-benzoylamino-α-hydroxy-γ-(1-naphthyl)propanoic acid 4,9-bis(acetyloxy)-2-benzoyloxy-1,2,3,4,5,6,7,8,10,13,14-undecahydro-1-hydroxy-8-hydroxymethyl-7,14,14,17-tetramethyl-1,10-methano-20H-cyclonona[2,3]benz[1,2-b]oxet-12-yl ester;

β-benzoylamino-α-hydroxy-γ-(2-naphthyl)propanoic acid 4,9-bis(acetyloxy)-2-benzoyloxy-1,2,3,4,5,6,7,8,10,13,14-undecahydro-1-hydroxy-8-hydroxymethyl-7,14,14,17-tetramethyl-1,10-methano-20H-cyclonona[2,3]benz[1,2-b]oxet-12-yl ester;

β-benzoylamino-α-hydroxy-γ-(pyridyl)propanoic acid 4,9-bis(acetyloxy)-2-benzoyloxy-1,2,3,4,5,6,7,8,10,13,14-undecahydro-1-hydroxy-8-hydroxymethyl-7,14,14,17-tetramethyl-1,10-methano-20H-cyclonona[2,3]benz[1,2-b]oxet-12-yl ester;

β-tert-benzoylamino-α-hydroxy-γ-(thienyl)propanoic acid 4,9-bis(acetyloxy)-2-benzoyloxy-1,2,3,4,5,6,7,8,10,13,14-undecahydro-1-hydroxy-8-hydroxymethyl-7,14,14,17-tetramethyl-1,10-methano-20H-cyclonona[2,3]benz[1,2-b]oxet-12-yl ester;

β-benzoylamino-α-hydroxy-γ-(furyl)propanoic acid 4,9-bis(acetyloxy)-2-benzoyloxy-1,2,3,4,5,6,7,8,10,13,14-undecahydro-1-hydroxy-8-hydroxymethyl-7,14,14,17-tetramethyl-1,10-methano-20H-cyclonona[2,3]benz[1,2-b]oxet-12-yl ester;

β-benzoylamino-α-hydroxy-γ-(oxazolyl)propanoic acid 4,9-bis(acetyloxy)-2-benzoyloxy-1,2,3,4,5,6,7,8,10,13,14-undecahydro-1-hydroxy-8-hydroxymethyl-7,14,14,17-tetramethyl-1,10-methano-20H-cyclonona[2,3]benz[1,2-b]oxet-12-yl ester;

β-benzoylamino-α-hydroxy-γ-(imidazolyl)propanoic acid 4,9-bis(acetyloxy)-2-benzoyloxy-1,2,3,4,5,6,7,8,10,13,14-undecahydro-1-hydroxy-8-hydroxymethyl-7,14,14,17-tetramethyl-1,10-methano-20H-cyclonona[2,3]benz[1,2-b]oxet-12-yl ester;

β-benzoylamino-α-hydroxy-γ-(pyrazinyl)propanoic acid 4,9-bis(acetyloxy)-2-benzoyloxy-1,2,3,4,5,6,7,8,10,13,14-undecahydro-1-hydroxy-8-hydroxymethyl-7,14,14,17-tetramethyl-1,10-methano-20H-cyclonona[2,3]benz[1,2-b]oxet-12-yl ester;

and

β-benzoylamino-α-hydroxy-γ-(pyridazinyl)propanoic acid 4,9-bis(acetyloxy)-2-benzoyloxy-1,2,3,4,5,6,7,8,10,13,14-undecahydro-1-hydroxy-8-hydroxymethyl-7,14,14,17-tetramethyl-1,10-methano-20H-cyclonona[2,3]benz[1,2-b]oxet-12-yl ester, as well as prodrugs thereof.

Although the above therapeutic agents have been provided for the purposes of illustration, it should be understood that the present invention is not so limited. Further, more than one therapeutic agent may be utilized at a time (i.e., in combination), or delivered sequentially.

C. Methods for Combining Stents with Paclitaxel Derivatives

In the practice of this invention, drug-coated or drug-impregnated implants and medical devices are provided which inhibit fibrosis in and around the device, or prevent "stenosis" of the device/implant in situ, thus enhancing the efficacy. Within various embodiments, fibrosis is inhibited by local or systemic release of specific pharmacological agents that become localized to the tissue adjacent to the device or implant. There are numerous methods available for optimizing delivery of the paclitaxel derivative to the site of the intervention and several of these are described below.

In one aspect, the present invention provides stents which comprise a paclitaxel derivative which inhibits fibrosis on at least one surface of, or around, the medical device once deployed in the patient. In certain embodiments, the stent device may be adapted to release the agent upon deployment of the device in the patient. The paclitaxel derivative may be released from all or only a portion of the stent. For example, the derivative may be released at only the distal ends or along the entire body of the device. Paclitaxel derivatives may be associated with stents in a variety of manners, including by (a) directly affixing to the implant or device a desired therapeutic agent or composition containing the therapeutic agent (e.g:, by either spraying or electrospraying the medical implant with a drug and/or carrier (polymeric or non-polymeric)-drug composition to create a film and/or coating on all, or part of an internal or external surface of the device; by dipping the implant or device into a drug and/or carrier (polymeric or non-polymeric)-drug solution to coat all or part of the device or implant; or by other covalent or noncovalent attachment of the therapeutic agent to the device or implant surface); (b) by coating the medical device or implant with a substance such as a hydrogel which either contains or which will in turn absorb the desired paclitaxel derivative or composition; (c) by interweaving a "thread" comprised of a paclitaxel derivative into the medical implant or device (e.g., a polymeric strand comprised of a paclitaxel derivative composition) or polymers which release a paclitaxel derivative from the thread); (d) by covering all, or a portion of the device or implant with a sleeve, cover, electrospun fabric or mesh comprising a paclitaxel derivative (i.e., a covering comprised of a paclitaxel derivative—a paclitaxel derivative or polymerized composition containing paclitaxel derivatives); (e) constructing all, or part of the device or implant itself with the desired agent or composition (e.g., a paclitaxel derivative or polymerized compositions of paclitaxel derivatives); (f) otherwise impregnating the device or implant with a desired paclitaxel derivative or composition; (g) composing all, or part, of the device or implant from a metal alloy that inhibits fibrosis; (h) utilizing specialized multi-drug releasing medical device systems (for example, U.S. Pat. Nos. 6,527,799; 6,293,967; 6,290,673; 6,241,762, U.S. Application Publication Nos. 2003/0199970A1 and 2003/0167085A1; and PCT Publication WO 03/015664) to deliver paclitaxel derivatives alone or in combination; and (i) constructing all, or part of the device or implant itself from a degradable or non-degradable polymer that is capable of releasing one or more paclitaxel derivatives (e.g., the paclitaxel derivative can be combined with the materials that are used to make the device such that the paclitaxel derivative is incorporated into the final device; this can include the stent structure itself, the outer covering or sleeve, if applicable, or both the stent structure and the outer covering or sleeve).

1) Coating of Stents with Paclitaxel Derivatives

As described above, a range of polymeric and non-polymeric materials can be used to incorporate the paclitaxel derivative onto or into a device. Coating of the device with the paclitaxel derivative or a composition that comprises the paclitaxel derivative is one method that may be used to associate the agent with the device. The anti-fibrosing agent or anti-fibrosing composition may be coated onto the entire device or a portion of the device using a method such as dipping, spraying, painting or vacuum deposition that is appropriate for the particular type of device. For these devices, the coating process can be performed in such a manner as to (a) coat the external surface of the stent, (b) coat the internal (luminal) surface of the stentor (c) coat all or parts of both the internal and external surfaces of the stent.

a) Dip coating

Dip coating is one coating process that can be used. In one embodiment, the paclitaxel derivative is dissolved in a solvent for the fibrosis agent and is then coated onto the device.

Paclitaxel derivative with an inert-solvent

In one embodiment, the solvent is an inert solvent for the device such that the solvent does not dissolve the medical device to any great extent and is not absorbed by the device to any great extent. The device can be immersed, either partially or completely, in the paclitaxel derivative/solvent solution for a specific period of time. The rate of immersion into the paclitaxel derivative/solvent solution can be altered (e.g., 0.001 cm per sec to 50 cm per sec). The device can then be removed from the solution. The rate at which the device can be withdrawn from the solution can be altered (e.g., 0.001 cm per sec to 50 cm per sec). The coated device can be air-dried. The dipping process can be repeated one or more times depending on the specific application. The device can be dried under vacuum to reduce residual solvent levels. This process will result in the paclitaxel derivative being coated on the surface of the device.

Paclitaxel derivative with a swelling solvent

In one embodiment, the solvent is one that will not dissolve the device but will be absorbed by the device. These solvents can thus swell the device to some extent. The device can be immersed, either partially or completely, in the paclitaxel derivative/solvent solution for a specific period of time (seconds to days). The rate of immersion into the paclitaxel derivative/solvent solution can be altered (e.g., 0.001 cm per sec to 50 cm per sec). The device can then be removed from the solution. The rate at which the device can be withdrawn from the solution can be altered (e.g., 0.001 cm per sec to 50 cm per sec). The coated device can be air-dried. The dipping process can be repeated one or more times depending on the specific application. The device can be dried under vacuum to reduce residual solvent levels. This process will result in the paclitaxel derivative being adsorbed into the medical device. The paclitaxel derivative may also be present on the surface of the device. The amount of surface associated paclitaxel derivative may be reduced by dipping the coated device into a solvent for the paclitaxel derivative or by spraying the coated device with a solvent for the paclitaxel derivative.

Paclitaxel derivative with a solvent

In one embodiment, the solvent is one that will be absorbed by the device and that will dissolve the device. The device can be immersed, either partially or completely, in the paclitaxel derivative/solvent solution for a specific period of time (seconds to hours). The rate of immersion into the paclitaxel derivative/solvent solution can be altered (e.g., 0.001 cm per sec to 50 cm per sec). The device can then be removed from the solution. The rate at which the device can be withdrawn from the solution can be altered (e.g., 0.001 cm per sec to 50 cm per sec). The coated device can be air-dried. The dipping process can be repeated one or more times depending on the specific application. The device can be dried under vacuum to reduce residual solvent levels. This process will result in the paclitaxel derivative being adsorbed into the medical device as well as being surface associated. In a preferred embodiment, the exposure time of the device to the solvent can be such that there are no significant permanent dimensional changes to the device. The paclitaxel derivative may also be present on a surface of the device. The amount of surface associated paclitaxel derivative may be reduced by dipping the coated device into a solvent for the paclitaxel derivative or by spraying the coated device with a solvent for the paclitaxel derivative.

In the above description the device can be a device that has not been modified as well as a device that has been further modified by association with a polymer, surface treated by plasma treatment, flame treatment, corona treatment, surface oxidation or reduction, surface etching, mechanical smoothing or roughening, or grafting prior to the affixing process.

In one embodiment, the paclitaxel derivative and a polymer are dissolved in a solvent, for both the polymer and the fibrosis-inhibiting agent, and are then coated onto the device, together or separately.

In any one of the above dip coating methods, the surface of the device can be treated with a plasma polymerization method prior to coating of the scarring agent or scarring agent containing composition, such that a thin polymeric layer is deposited onto a surface of the device. Examples of such methods include parylene coating of devices and the use of various monomers such hydrocyclosiloxane monomers. Parylene coating may be especially advantageous if the device, or a portion of the device, is composed of materials (e.g., stainless steel, nitinol) that do not allow incorporation of the therapeutic agent(s) into a surface using one of the above methods. A parylene primer layer may be deposited onto the device using a parylene coater (e.g., PDS 2010 LABCOTER2 from Cookson Electronics) and a suitable reagent (e.g., di-p-xylylene or dichloro-di-p-xylylene) as the coating feed material. Parylene compounds are commercially available, for example, from Specialty Coating Systems, Indianapolis, Ind.), including PARYLENE N(di-p-xylylene), PARYLENE C (a monchlorinated derivative of PARYLENE N, and PARYLENE D, a dichlorinated derivative of PARYLENE N).

Paditaxel derivative/polymer with an inert-solvent

In one embodiment, the solvent is an inert solvent for the device such that the solvent does not dissolve the medical device to any great extent and is not absorbed by the device to any great extent. The device can be immersed, either partially or completely, in a paclitaxel derivative/polymer/solvent solution for a specific period of time; The rate of immersion into the paclitaxel derivative/polymer/solvent solution can be altered (e.g., 0.001 cm per sec to 50 cm per sec). The device can then be removed from the solution. The rate at which the device can be withdrawn from the solution can be altered (e.g., 0.001 cm per sec to 50 cm per sec). The coated device can be air-dried. The dipping process can be repeated one or more times depending on the specific application. The device can be dried under vacuum to reduce residual solvent levels. This process will result in the paclitaxel derivative/polymer being coated on a surface of the device.

Paclitaxel/derivative/polymer with a swelling solvent

In one embodiment, the solvent is one that will not dissolve the device but will be absorbed by the device. These solvents can thus swell the device to some extent. The device can be immersed, either partially or completely, in a paclitaxel derivative/polymer/solvent solution for a specific period of time (seconds to days). The rate of immersion into the paclitaxel derivative/polymer/solvent solution can be altered (e.g., 0.001 cm per sec to 50 cm per sec). The device can then be removed from the solution. The rate at which the device can be withdrawn from the solution can be altered (e.g., 0.001 cm per sec to 50 cm per sec). The coated device can be air-dried. The dipping process can be repeated one or more times depending on the specific application. The device can be dried under vacuum to reduce residual solvent levels. This process will result in the paclitaxel derivative/polymer being coated on a surface of the device as well as the potential for the paclitaxel derivative being adsorbed into the medical device. The paclitaxel derivative may also be present on a surface of the device. The amount of surface associated paclitaxel derivative may be reduced by dipping the coated device into a solvent for the paclitaxel derivative or by spraying the coated device with a solvent for the paclitaxel derivative.

Paclitaxel derivative/polymer with a solvent

In one embodiment, the solvent is one that will be absorbed by the device and that will dissolve the device. The device can be immersed, either partially or completely, in a paclitaxel derivative/solvent solution for a specific period of time (seconds to hours). The rate of immersion into the paclitaxel derivative/solvent solution can be altered (e.g., 0.001 cm per sec to 50 cm per sec). The device can then be removed from the solution. The rate at which the device can be withdrawn from the solution can be altered (e.g., 0.001 cm per sec to 50 cm per sec). The coated device can be air-dried. The dipping process can be repeated one or more times depending on the specific application. The device can be dried under vacuum to reduce residual solvent levels. In the preferred embodiment, the exposure time of the device to the solvent can be such that there are not significant permanent dimensional changes to the device (other than those associated with the coating itself). The paclitaxel derivative may also be present on a surface of the device. The amount of surface associated paclitaxel derivative may be reduced by dipping the coated device into a solvent for the paclitaxel derivative or by spraying the coated device with a solvent for the paclitaxel derivative.

In the above description the device can be a device that has not been modified as well as a device that has been further modified by coating with a polymer (e.g., parylene), surface treated by plasma treatment, flame treatment, corona treatment, surface oxidation or reduction, surface etching, mechanical smoothing or roughening, or grafting prior to the coating process.

In another embodiment, a suspension of the paclitaxel derivative in a polymer solution can be prepared. The suspension can be prepared by choosing a solvent that can dissolve the polymer but not the paclitaxel derivative or a solvent that can dissolve the polymer and in which the paclitaxel derivative is above its solubility limit. In similar processes described above, a device can be dipped into the suspension of the fibrosis-inhibiting and polymer solution such that the device is coated with a polymer that has a paclitaxel derivative suspended within it.

b) Spray coating

Spray coating is another coating process that can be used. In a spray coating process, a solution or suspension of a paclitaxel derivative, with or without a polymeric or non-polymeric carrier, is nebulized and directed to the device to be coated by a stream of gas. One can use spray devices such as an air-brush (for example models 2020, 360, 175, 100, 200, 150, 350, 250, 400, 3000, 4000, 5000, 6000 from Badger Air-brush Company, Franklin Park, IL), spray painting equipment, TLC reagent sprayers (for example Part# 14545 and 14654, Alltech Associates, Inc. Deerfield, IL, and ultrasonic spray devices (for example those available from Sono-Tek, Milton, NY). One can also use powder sprayers and electrostatic sprayers.

In one embodiment, the paclitaxel derivative is dissolved in a solvent for the fibrosis agent and is then sprayed onto the device.

Paclitaxel derivative with an inert-solvent

In one embodiment, the solvent is an inert solvent for the device such that the solvent does not dissolve the medical device to any great extent and is not absorbed by the device to any great extent. The device can be held in place or the device can be mounted onto a mandrel or rod that has the ability to move in an X, Y or Z plane or a combination of these planes. Using one of the above described spray devices, the device can be spray coated such that the device is either partially or completely coated with the paclitaxel derivative/solvent solution. The rate of spraying of the paclitaxel derivative/solvent solution can be altered (e.g. 0.001 ml per sec to 10 mL per sec) to ensure that a good coating of the paclitaxel derivative is obtained. The coated device can air-dried. The spray coating process can be repeated one or more times depending on the specific application. The device can be dried under vacuum to reduce residual solvent levels. This process will result in the paclitaxel derivative being coated on a surface of the device.

Paclitaxel derivative with a swelling solvent

In one embodiment, the solvent is one that will not dissolve the device but will be absorbed by the device. These solvents can thus swell the device to some extent. The device can be spray coated, either partially or completely, in the paclitaxel derivative/solvent solution. The rate of spraying of the paclitaxel derivative/solvent solution can be altered (e.g., 0.001 mL per sec to 10 mL per sec) to ensure that a good coating of the paclitaxel derivative is obtained. The coated device can be air-dried. The spray coating process can be repeated one or more times depending on the specific application. The device can be dried under vacuum to reduce residual solvent levels. This process will result in the paclitaxel derivative being adsorbed into the medical device. The paclitaxel derivative may also be present in a surface of the device. The amount of surface associated paclitaxel derivative may be reduced by dipping the coated device into a solvent for the paclitaxel derivative or by spraying the coated device with a solvent for the paclitaxel derivative.

Paclitaxel derivative with a solvent

In one embodiment, the solvent is one that will be absorbed by the device and that will dissolve the device. The device can be spray coated, either partially or completely, in the paclitaxel derivative/solvent solution. The rate of spraying of the paclitaxel derivative/solvent solution can be altered (e.g., 0.001 mL per sec to 10 mL per sec) to ensure that a good coating of the paclitaxel derivative is obtained. The coated device can be air-dried. The spray coating process can be repeated one or more times depending on the specific application. The device can be dried under vacuum to reduce residual solvent levels. This process will result in the paclitaxel derivative being adsorbed into the medical device as well as being surface associated. In the preferred embodiment, the exposure time of the device to the solvent can be such that there are not significant permanent dimensional changes to the device. The paclitaxel derivative may also be present on the surface of the device. The amount of surface associated paclitaxel derivative may be reduced by dipping the coated device into a solvent for the paclitaxel derivative or by spraying the coated device with a solvent for the paclitaxel derivative.

In the above description the device can be a device that has not been modified as well as a device that has been further modified by coating with a polymer (e.g., parylene), surface treated by plasma treatment, flame treatment, corona treatment, surface oxidation or reduction, surface etching, mechanical smoothing or roughening, or grafting prior to the coating process.

In one embodiment, the paclitaxel derivative and a polymer are dissolved in a solvent, for both the polymer and the anti-fibrosing agent; and are then spray coated onto the device.

Paclitaxel derivative/polymer with an inert-solvent

In one embodiment, the solvent is an inert solvent for the device such that the solvent does not dissolve the medical device to any great extent and is not absorbed by the device to any great extent. The device can be spray coated, either partially or completely, in the paclitaxel derivative/polymer/solvent solution for a specific period of time. The rate of spraying of the paclitaxel derivative/solvent solution can be altered (e.g., 0.001 ml per sec to 10 ml per sec) to ensure that a good coating of the paclitaxel derivative is obtained. The coated device can be air-dried. The spray coating process can be repeated one or more times depending on the specific application. The device can be dried under vacuum to reduce residual solvent levels. This process will result in the paciitaxel derivative/polymer being coated on the surface of the device.

Paclitaxel derivative/polymer with a swelling solvent

In one embodiment, the solvent is one that will not dissolve the device but will be absorbed by the device. These solvents can thus swell the device to some extent. The device can be spray coated, either partially or completely, in the paclitaxel derivative/polymer/solvent solution. The rate of spraying of the paclitaxel derivative/solvent solution can be altered (e.g., 0.001 mL per sec to 10 mL per sec) to ensure that a good coating of the paclitaxel derivative is obtained. The coated device can be air-dried. The spray coating process can be repeated one or more times depending on the specific application. The device can be dried under vacuum to reduce residual solvent levels. This process will result in the paclitaxel derivative/polymer being coated onto the surface of the device as well as the potential for the paclitaxel derivative being adsorbed into the medical device. The paclitaxel derivative may also be present on the surface of the device. The amount of surface associated paclitaxel derivative may be reduced by dipping the coated device into a solvent for the paclitaxel derivative or by spraying the coated device with a solvent for the paclitaxel derivative.

Paclitaxel derivative/polymer with a solvent

In one embodiment, the solvent is one that will be absorbed by the device and that will dissolve the device. The device can be spray coated, either partially or completely, in the paclitaxel derivative/solvent solution. The rate of spraying of the paclitaxel derivative/solvent solution can be altered (e.g., 0.001 mL per sec to 10 mL per sec) to ensure that a good coating of the paclitaxel derivative is obtained. The coated device can be air-dried. The spray coating process can be repeated one or more times depending on the specific application. The device can be dried under vacuum to reduce residual solvent levels. In the preferred embodiment, the exposure time of the device to the solvent can be such that there are not significant permanent dimensional changes to the device (other than those associated with the coating itself). The paclitaxel derivative may also be present on the surface of the device. The amount of surface associated paclitaxel derivative may be reduced by dipping the coated device into a solvent for the Paclitaxel derivative or by spraying the coated device with a solvent for the paclitaxel derivative.

In the above description the device can be a device that has not been modified as well as a device that has been further modified by coating (entirely or partially) with a polymer (e.g., parylene), surface treated by plasma treatment, flame treatment, corona treatment, surface oxidation or reduction, surface etching, mechanical smoothing or roughening, or grafting prior to the coating process.

In another embodiment, a suspension of the paclitaxel derivative in a polymer solution can be prepared. The suspension can be prepared by choosing a solvent that can dissolve the polymer but not the paclitaxel derivative or a solvent that can dissolve the polymer and in which the paclitaxel derivative is above its solubility limit. In similar processes described above, the suspension of the fibrosis-inhibiting and polymer solution can be sprayed onto the device such that the device is coated with a polymer that has a paclitaxel derivative suspended within it.

In all such embodiments, the devices may comprise one or more partial or complete coatings comprising a paclitaxel derivative. The devices may also comprise a paclitaxel derivative-free top coating.

2) Localized Delivery of Paclitaxel Derivatives to Treatment Site

In another aspect, a paclitaxel derivative may be delivered to the treatment site via systemic, regional or local delivery methods. In one aspect, the paclitaxel derivative or a composition comprising a paclitaxel derivative may be infiltrated into or onto tissue surrounding the stent. The tissue cavity into which the stent is placed can be treated with a paclitaxel derivative prior to, during, or after the procedure. Several of the techniques that can be used to achieve preferentially elevated levels of paclitaxel derivatives in the vicinity of the stent include: (a) using drug-delivery catheters for local, regional or systemic delivery of fibrosis inhibiting agents to the tissue surrounding the device or implant (typically, drug delivery catheters are advanced through the circulation or inserted directly into tissues under radiological guidance (e.g., magnetic, ultrasonic, or MRI guidance) until they reach the desired anatomical location; the fibrosis inhibiting agent can then be released from the catheter lumen in high local concentrations in order to deliver therapeutic doses of the drug to the tissue surrounding the device or implant); (b) chemical modification of the fibrosis-inhibiting drug or formulation designed to increase uptake of the agent into damaged tissues (e.g., antibodies directed against damaged or healing tissue components such as macrophages, neutrophils, smooth muscle cells, fibroblasts, extracellular matrix components, neovascular tissue); (c) chemical modification of the fibrosis inhibiting drug or formulation designed to localize the drug to areas of bleeding or disrupted vasculature; (d) direct injection of the paclitaxel derivative into the tissue, for example, under endoscopic vision; and/or applying the composition into the anatomical space where the device will be placed (e.g., using a sprayable formulation or a polymeric gel loaded with a paclitaxel derivative), where the composition may be applied to the implantation site (e.g., topical application) or the implant/device surface.

Sustained-Release Preparations of Paditaxel Derivatives

As described previously desired paclitaxel derivatives may be admixed with, blended with; conjugated to, or, otherwise modified to contain a polymer composition (which may be either biodegradable or non-biodegradable) or a non-polymeric composition in order to release the therapeutic agent, and in a preferred embodiment, over a prolonged period of time. For many of the aforementioned embodiments, localized delivery as well as localized sustained delivery of the fibrosis inhibiting agent may be desired. For example, a desired paclitaxel derivative may be admixed with, blended with, conjugated to, or, otherwise modified to contain a polymeric composition (which may be either biodegradable or non-biodegradable) or non-polymeric composition in order to release the paclitaxel derivative over a period of time.

Numerous polymeric and non-polymeric compositions may be used in the practice of the invention.

In one aspect, polymeric compositions may include a biodegradable polymer. Representative examples of biodegradable polymers suitable for the delivery of paclitaxel derivatives include albumin, collagen, gelatin, hyaluronic acid, starch, cellulose and cellulose derivatives (e.g., methylcellulose, hydroxypropylcellulose, hydroxypropylmethylcellulose, carboxymethylcellulose, cellulose acetate phthalate, cellulose acetate succinate, hydroxypropylmethylcellulose phthalate), casein, dextrans, polysaccharides, fibrinogen, poly(ether ester) multiblock copolymers, based on poly(ethylene glycol) and poly (butylene terephthalate), tyrosine-derived polycarbonates (e.g., U.S. Pat. No. 6,120,491), poly(hydroxyl acids), poly (D,L-lactide), poly(D,L-lactide-co-glycolide), poly (glycolide), poly(hydroxybutyrate), polydioxanone, poly (alkylcarbonate) and poly(orthoesters), polyesters, poly (hydroxyvaleric acid), polydioxanone, degradable polyesters, poly(malic acid), poly(tartronic acid), poly (acrylamides), polyanhydrides, polyphosphazenes, poly (amino acids), poly(alkylene oxide)-poly(ester) block copolymers (e.g., X—Y, X—Y—X or Y—X—Y, R—(Y—X)$_n$, R—(X—Y)$_n$ where X is a polyalkylene oxide and Y is a polyester (e.g., polyester can comprise the residues of one or more of the monomers selected from lactide, lactic acid, glycolide, glycolic acid, ϵ-caprolactone, gamma-caprolactone, hydroxyvaleric acid, hydroxybutyric acid, beta-butyrolactone, gamma-butyrolactone, gamma-valerolactone, γ-decanolactone, δ-decanolactone, trimethylene carbonate, 1,4-dioxane-2-one or 1,5-dioxepan-2one.), R is a multifunctional initiator and copolymers as well as blends thereof) and the copolymers as well as blends thereof (see generally, Illum. L., Davids, S.S. (eds) "*Polymers in Controlled Drug Delivery*" Wright, Bristol, 1987; Arshady, *J. Controlled Release* 17:1-22, 1991; Pitt, *Int. J. Phar.* 59:173-196, 1990; Holland et al., *J. Controlled Release* *4*:155-0180, 1986).

In another aspect, polymeric compositions may include a non-biodegradable polymer. Representative examples of non-degradable polymers suitable for the delivery of paclitaxel derivatives include poly(ethylene-co-vinyl acetate) ("EVA") copolymers, non-degradable polyesters, such as poly(ethylene terephthalate), silicone rubber, acrylic polymers (polyacrylate, polyacrylic acid, polymethylacrylic acid, polymethylmethacrylate, poly(butyl methacrylate)), poly(alkylcynoacrylate) (e.g., poly(ethylcyanoacrylate), poly(butylcyanoacrylate) poly(hexylcyanoacrylate) poly (octylcyanoacrylate)), acrylic resin, polyethylene, polypropylene, polyamides (nylon 6,6), polyurethanes (e.g., CHRONOFLEX AR, CHRONOFLEX AL, BIONATE; and PELLETHANE), poly(ester urethanes), poly(ether urethanes), poly(ester-urea), cellulose esters (e.g., nitrocellulose), polyethers (poly(ethylene oxide), poly (propylene oxide), polyoxyalkylene ether block copolymers based on ethylene oxide and propylene oxide such as the PLURONIC polymers (e.g., F-127 or F87) from BASF Corporation (Mount Olive, N.J.), and poly(tetramethylene glycol), styrene-based polymers (polystyrene, poly(styrene sulfonic acid), poly(styrene)-block-poly(isobutylene)-block-poly(styrene), poly(styrene)-poly(isoprene) block copolymers), and vinyl polymers (polyvinylpyrrolidone, poly(vinyl alcohol), poly(vinyl acetate phthalate) as well as copolymers and blends thereof. Polymers may also be developed which are either anionic (e.g., alginate, carrageenan, carboxymethyl cellulose, poly(acrylamido-2-methyl propane sulfonic acid) and copolymers thereof, poly (methacrylic acid and copolymers thereof and poly(acrylic acid) and copolymers thereof, as well as blends thereof, or cationic (e.g., chitosan, poly-L-lysine; polyethylenimine, and poly(allyl amine)) and blends, copolymers and branched polymers thereof (see generally, Dunn et al., *J. Applied Polymer Sci:* 50:353-365, 1993; Cascone et al., *J. Materials Sci.: Materials in Medicine* 5:770-774, 1994; Shiraishi et al., *Biol. Pharm. Bull.* 16(11):1164-1168, 1993; Thacharodi and Rao, *Int'l J. Pharm.* 120:115-118, 1995; Miyazaki et al., *Int'l J. Pharm.* 118:257-263, 1995).

Examples of preferred polymeric carriers include poly (ethylene-co-vinyl acetate), polyurethanes (e.g., CHRONOFLEX AR, CHRONOFLEXAL, BIONATE, and PELLETHANE), poly (D,L-lactic acid) oligomers and polymers, poly (L-lactic acid) oligomers and polymers, poly (glycolic acid), copolymers of lactic acid and glycolic acid, poly (caprolactone), poly (valerolactone), polyanhydrides; copolymers of poly (caprolactone) or poly (lactic acid) with a polyethylene glycol (e.g., MePEG), poly(alkylene oxide)-poly(ester)block copolymers (e.g., X—Y, X—Y—X or Y—X—Y, R—(Y—X)$_n$, R—(X—Y)$_n$ where X is a polyalkylene oxide and Y is a polyester (e.g., polyester can comprise the residues of one or more of the monomers selected from lactide, lactic acid, glycolide, glycolic acid, ϵ-caprolactone, gamma-caprolactone, hydroxyvaleric acid, hydroxybutyric acid, beta-butyrolactone, gamma-butyrolactone, gamma-valerolactone, γ-decanolactone, δ-decanolactone, trimethylene carbonate, 1,4-dioxane-2-one or 1,5-dioxepan-2one.), R is a multifunctional initiator and copolymer as well as blends thereof), nitrocellulose, silicone rubbers, poly(styrene)block-poly(isobutylene)-block-poly (styrene), poly(acrylate) polymers and blends, admixtures, or co-polymers of any of the above. Other preferred polymers include collagen, poly(alkylene oxide)-based polymers, polysaccharides such as hyaluronic acid, chitosan and fucans, and copolymers of polysaccharides with degradable polymers, as well as blends thereof.

Other representative polymers capable of release (e.g., sustained localized delivery) of paclitaxel derivatives include carboxylic polymers, polyacetates, polycarbonates, polyethers, polyethylenes, polyvinylbutyrals, polysilanes, polyureas, polyoxides, polystyrenes, polysulfides, polysulfones, polysulfonides, polyvinylhalides, pyrrolidones, rubbers, thermal-setting polymers, cross-linkable acrylic and methacrylic polymers, ethylene acrylic acid copolymers, styrene acrylic copolymers, vinyl acetate polymers and copolymers, vinyl acetal polymers and copolymers, epoxies, melamines, other amino resins, phenolic polymers, and copolymers thereof, water-insoluble cellulose ester polymers (including cellulose acetate propionate, cellulose acetate, cellulose acetate butyrate, cellulose nitrate, cellulose acetate phthalate, and mixtures thereof), polyvinylpyrrolidone, polyethylene glycols, polyethylene oxide, polyvinyl alcohol, polyethers, polysaccharides, hydrophilic polyurethane, polyhydroxyacrylate, dextran, xanthan, hydroxypropyl cellulose, and homopolymers and copolymers of N-vinylpyrrolidone, N-vinyllactam, N-vinyl butyrolactam, N-vinyl caprolactam, other vinyl compounds having polar pendant groups, acrylate and methacrylate having hydrophilic esterifying groups, hydroxyacrylate, and acrylic acid, and combinations thereof; cellulose esters and ethers, ethyl cellulose, hydroxyethyl cellulose, cellulose nitrate, cellulose acetate, cellulose acetate butyrate, cellulose acetate propionate, natural and synthetic elastomers, rubber, acetal, styrene polybutadiene, acrylic resin, polyvinylidene chloride, polycarbonate, homopolymers and copolymers of vinyl compounds, polyvinylchloride, and polyvinylchloride acetate.

Representative examples of patents relating to drug-delivery polymers and the preparation included PCT Publication Nos. WO 98/19713, WO 01/17575, WO 01/41821; WO 01/41822, and WO 01/15526 (as well as the corresponding U.S. applications); U.S. Pat Nos. 4,500,676, 4,582,865, 4,629,623, 4,636,524, 4,713,448, 4,795,741, 4,913,743, 5,069,899, 5,099,013, 5,128,326, 5,143,724, 5,153,174, 5,246,698, 5,266,563, 5,399,351, 5,525,348, 5,800,412, 5,837,226, 5,942,555, 5,997,517, 6,007,833, 6,071,447, 6,090,995, 6,106,473, 6,110,483, 6,121,027, 6,156,345, 6,214,901, 6,368,611, 6,630,155, 6,528,080, RE37,950, 6,46,1631, 6,143,314, 5,990,194, 5,792,469, 5,780,044, 5,759,563, 5,744,153, 5,739,176, 5,733,950, 5,681,873, 5,599,552, 5,340,849, 5,278,202, 5,278,201, 6,589,549, 6,287,588, 6,201,072, 6,117,949, 6,004,573, 5,702,717, 6,413,539, 5,714,159, 5,612,052; and U.S. Patent Application Publication Nos. 2003/0068377, 2002/0192286, 2002/0076441, and 2002/0090398.

In one embodiment, all or a portion of the device is coated with a primer (bonding) layer and a drug release layer, as described in U.S. Patent application entitled, "Stent with Medicated Multi-Layer Hybrid Polymer Coating," filed Sep. 16, 2003 (U.S. Ser. No. 10/662,877).

In order to develop a hybrid polymer delivery system for targeted therapy, it is desirable to be able to control and manipulate the properties of the system both in terms of physical and drug release characteristics. The active agents can be imbibed into a surface hybrid polymer layer, or incorporated directly into the hybrid polymer coating solutions. Imbibing drugs into surface polymer layers is an efficient method for evaluating polymer-drug performance in the laboratory, but for commercial production it may be preferred for the polymer and drug to be premixed in the casting mixture. Greater efficacy can be achieved by combining the two elements in the coating compostions in order to control the ratio of active agent to polymer in the coatings. Such ratios are important parameters to the final properties of the medicated layers, i.e., they allow for better control of active agent concentration and duration of pharmacological activity.

Typical polymers used in the drug-release system can include water-insoluble cellulose esters, various polyurethane polymers including hydrophilic and hydrophobic versions, hydrophilic polymers such as polyethylene glycol (PEG), polyethylene oxide (PEO), polyvinylpyrrolidone (PVP), PVP copolymers such as vinyl acetate, hydroxyethyl methacrylate (HEMA) and copolymers such as methylmethacrylate (PMMA-HEMA), and other hydrophilic and hydrophobic acrylate polymers and copolymers containing functional groups such as carboxyl and/or hydroxyl.

Cellulose esters such as cellulose acetate, cellulose acetate propionate, cellulose acetate butyrate, cellulose acetate phthalate, and cellulose nitrate may be used. In one aspect of the invention, the therapeutic agent is formulated with a cellulose ester. Cellulose nitrate is a preferred cellulose ester because of its compatibility with the active agents and its ability to impart non-tackiness and cohesiveness to the coatings. Cellulose nitrate has been shown to stabilize entrapped drugs in ambient and processing conditions. Various grades of cellulose nitrate are available and may be used in a coating on a device, including cellulose nitrate having a nitrogen content=11.8-12.2%. Various viscosity grades, including 3.5, 0.5 or 0.25 seconds, may be used in order to provide proper rheological properties when combined with the coating solids used in these formulations. Higher or lower viscosity grades can be used. However, the higher viscosity grades can be more difficult to use because of their higher viscosities. Thus, the lower viscosity grades, such as 3.5, 0.5 or 0.25 seconds, are generally preferred. Physical properties such as tensile strength, elongation, flexibility, and softening point are related to viscosity (molecular weight) and can decrease with the lower molecular weight species, especially below the 0.25 second grades.

The cellulose derivatives comprise hydroglucose structures. Cellulose nitrate is a hydrophobic, water-insoluble polymer, and has high water resistance properties. This structure leads to high compatibility with many active agents, accounting for the high degree of stabilization provided to drugs entrapped in cellulose nitrate. The structure of nitrocellulose is given below:

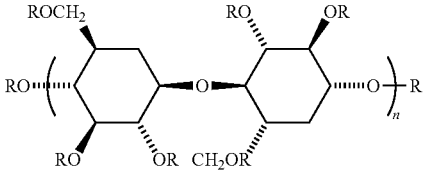

nitrocellulose

R = $NO_2$ or H

Cellulose nitrate is a hard, relatively inflexible polymer, and has limited adhesion to many polymers that are typically used to make medical devices. Also control of drug elution dynamics is limited if only one polymer is used in the binding matrix. Accordingly, in one embodiment of the invention, the therapeutic agent is formulated with two or more polymers before being associated with the device. In one aspect, the agent is formulated with the both polyurethane ((e.g., CHRONOFLEX AR, CHRONOFLEX AL, and BIONATE, PELLETHANE) and cellulose nitrate to provide a hybrid polymer drug loaded matrix. Polyurethanes provide the hybrid polymer matrix with greater flexibility and adhesion to the device, particularly when the device has been pre-coated with a primer. Polyurethanes can also be used to slow or hasten the drug elution from coatings. Aliphatic, aromatic, polytetramethylene ether glycol, and polycarbonate are among the types of polyurethanes, which can be used in the coatings. In one aspect, a paclitaxel derivative (e.g., paclitaxel) may be incorporated into a carrier that includes a polyurethane and a cellulose derivative. A heparin complex, such as benzalkonium heparinate or tridodecylammonium heparinate), may optionally be included in the formulation.

From the structure below, it is possible to see how more or less hydrophilic polyurethane polymers may be created based on the number of hydrophilic groups contained in the polymer structures. In one aspect of the invention, the device is associated with a formulation that includes therapeutic agent, cellulose ester, and a polyurethane that is water-insoluble, flexible, and compatible with the cellulose ester.

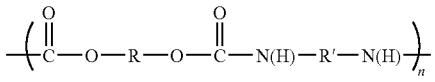

polyurethanes

R = polyether or polyester
R = aliphatic or aromatic

Polyvinylpyrrolidone (PVP) is a polyamide that possesses unusual complexing and colloidal properties and is essentially physiologically inert. PVP and other hydrophilic polymers are typically biocompatible. PVP may be incorporated into drug loaded hybrid polymer compositions in order to increase drug release rates. In one embodiment, the concentration of PVP that is used in drug loaded hybrid polymer compositions can be less than 20%. This concentration cannot make the layers bioerodable or lubricious. In general, PVP concentrations from <1% to greater than 80% are deemed workable. In one aspect of the invention, the therapeutic agent that is associated with an device is formulated with a PVP polymer.

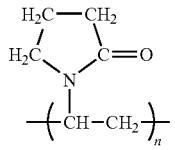

polyvinylpyrrolidone

Acrylate polymers and copolymers including polymethylmethacrylate (PMMA) and polymethylmethacrylate hydroxyethyl methacrylate (PMMA/HEMA) are known for their biocompatibility as a result of their widespread use in contact and intraocular lens applications. This class of polymer generally provokes very little smooth muscle and endothelial cell growth, and very low inflammatory response (Bar). These polymers/copolymers are compatible with drugs and the other polymers and layers of the instant invention. Thus, in one aspect, the device is associated with a composition that comprises a paclitaxel derivative as described above, and an acrylate polymer or copolymer.

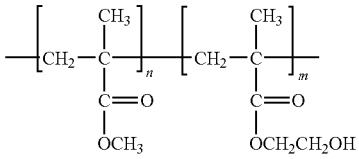

Methylmethacrylate hydroxyethylmethacrylate copolymer

It should be obvious to one of skill in the art that the polymers as described herein can also be blended or copolymerized in various compositions as required to deliver therapeutic doses of paclitaxel derivatives.

Polymeric carriers for paclitaxel derivatives can be fashioned in a variety of forms, with desired release characteristics and/or with specific properties depending upon the device, composition or implant being utilized. For example, polymeric carriers may be fashioned to release a paclitaxel derivative upon exposure to a specific triggering event such as pH (see, e.g., Heller et al., "Chemically Self-Regulated Drug Delivery Systems," in *Polymers in Medicine III*, Elsevier Science Publishers B.V., Amsterdam, 1988, pp. 175-188; Kang et al., *J. Applied Polymer Sci.* 48:343-354, 1993; Dong et al., *J. Controlled Release* 19:171-178, 1992;

Dong and Hoffman, *J. Controlled Release* 15:141-152, 1991; Kim et al., *J. Controlled Release* 28:143-152, 1994; Cornejo-Bravo et al., *J. Controlled Release* 33:223-229, 1995; Wu and Lee, *Pharm. Res.* 10(10):1544-1547, 1993; Serres et al., *Pharm. Res:* 13(2):196-201, 1996; Peppas, "Fundamentals of pH- and Temperature-Sensitive Delivery Systems," in Gurny et al. (eds.), *Pulsatile Drug Delivery*, Wissenschaftliche Verlagsgesellschaft mbH, Stuttgart, 1993, pp. 41-55; Doelker, "Cellulose Derivatives," 1993, in Peppas and Langer (eds.), *Bipolymers I*, Springer-Verlag, Berlin). Representative examples of pH-sensitive polymers include poly (acrylic acid) and its derivatives (including for example, homopolymers such as poly(aminocarboxylic acid); poly(acrylic acid); poly(methyl acrylic acid), copolymers of such homopolymers, and copolymers of poly (acrylic acid) and/or acrylate or acrylamide lmonomers such as those discussed above. Other pH sensitive polymers include polysaccharides such as cellulose acetate phthalate; hydroxypropylmethylcellulose phthalate; hydroxypropylmethylcellulose acetate succinate; cellulose acetate trimellilate; and chitosan. Yet other pH sensitive polymers include any mixture of a pH sensitive polymer and a water-soluble polymer.

Likewise, paclitaxel derivatives can be delivered via polymeric carriers which are temperature sensitive (see, e.g., Chen et al., "Novel Hydrogels of a Temperature-Sensitive PLURONIC Grafted to a Bioadhesive Polyacrylic Acid Backbone for Vaginal Drug Delivery," in *Proceed. Intern. Symp. Control. Rel. Bioact. Mater.* 22:167-168, Controlled Release Society, Inc., 1995; Okano, "Molecular Design of Stimuli-Responsive Hydrogels for Temporal Controlled Drug Delivery," in *Proceed. Intern. Symp. Control. Rel. Bioact. Mater:* 22:111-112, Controlled Release Society, Inc., 1995; Johnston et al., *Pharm. Res.* 9(3):425-433, 1992; Tung, *Int'l J. Pharm.* 107:8590, 1994; Harsh and Gehrke, *J. Controlled Release* 17:175-186, 1991; Bae et al., *Pharm. Res.* 8(4):531-537, 1991; Dinarvand and D'Emanuele, *J. Controlled Release* 36:221-227, 1995; Yu and Grainger, "Novel Thermo-sensitive Amphiphilic Gels: Poly N-isopropylacrylamide-co-sodium acrylate-co-n-N-alkylacrylamide Network Synthesis and Physicochemical Characterization," Dept. of Chemical & Biological Sci., Oregon Graduate Institute of Science & Technology, Beaverton, Oreg., pp. 820-821; Zhou and Smid, "Physical Hydrogels of Associative Star Polymers," Polymer Research Institute, Dept. of Chemistry, College of Environmental Science and Forestry, State Univ. of New York, Syracuse, N.Y., pp. 822-823; Hoffman et al., "Characterizing Pore Sizes and Water 'Structure' in Stimuli-Responsive Hydrogels," Center for Bioengineering, Univ. of Washington, Seattle, Wash., p. 828; Yu and Grainger, "Thermo-sensitive Swelling Behavior in Crosslinked N-isopropylacrylamide Networks: Cationic, Anionic and Ampholytic Hydrogels," Dept. of Chemical & Biological Sci., Oregon Graduate Institute of Science & Technology, Beaverton, Oreg., pp. 829-830; Kim et al., *Pharm. Res.* 9(3):283-290, 1992; Bae et al., *Pharm. Res.* 8(5):624-628, 1991; Kono et al., *J. Controlled Release* 30:69-75, 1994; Yoshida et al., *J. Controlled Release* 32:97-102, 1994; Okano et al., *J. Controlled Release* 36:125-133, 1995; Chun and Kim, *J. Controlled Release* 38:39-47, 1996; D'Emanuele and Dinarvand, *Int'l J. Pharm.* 118:237-242, 1995; Katono et al., *J. Controlled Release* 16:215-228, 1991; Hoffman, "Thermally Reversible Hydrogels Containing Biologically Active Species," in Migliaresi et al. (eds.), *Polymers in Medicine III*, Elsevier Science Publishers B.V., Amsterdam, 1988, pp. 161-167; Hoffman, "Applications of Thermally Reversible Polymers and Hydrogels in Therapeutics and Diagnostics," in *Third International Symposium on Recent Advances in Drug Delivery Systems*, Salt Lake City; UT, Feb. 24-27, 1987, pp. 297-305; Gutowska et al., *J. Controlled Release* 22:95-104, 1992; Palasis and Gehrke, *J. Controlled Release* 18:1-12, 1992; Paavola et al., *Pharm. Res.* 12(12): 1997-2002, 1995).

Representative examples of thermogelling polymers, and the gelatin temperature (LCST (° C.)) include homopolymers such as poly(N-methyl-N-n-propylacrylamide), 19.8° C.; poly(N-n-propylacrylamide), 21.5° C.; poly(N-methyl-N-isopropylacrylamide), 22.3° C.; poly(N-n-propylmethacrylamide), 28.0° C.; poly(N-isopropylacrylamide), 30.9° C.; poly(N, n-diethylacrylamide), 32.0° C.; poly(N-isopropylmethacrylamide), 44.0° C.; poly(N-cyclopropylacrylamide), 45.5° C.; poly(N-ethylmethyacrylamide), 50.0° C.; poly(N-methyl-N-ethylacrylamide), 56.0° C.; poly(N-cyclopropylmethacrylamide), 59.0° C.; poly(N-ethylacrylamide), 72.0° C. Moreover thermogelling polymers may be made by preparing copolymers between (among) monomers of the above, or by combining such homopolymers with other water-soluble polymers such as acrylmonomers (e.g., acrylic acid and derivatives thereof, such as methylacrylic acid, acrylate monomers and derivatives thereof, such as butyl methacrylate, butyl acrylate, lauryl acrylate, and acrylamide monomers and derivatives thereof, such as N-butyl acrylamide and acrylamide).

Other representative examples of thermogelling polymers include cellulose ether derivatives such as hydroxypropyl cellulose, 41° C.; methyl cellulose, 55° C.; hydroxypropylmethyl cellulose, 66° C.; and ethylhydroxyethyl cellulose, polyalkylene oxide-polyester block copolymers of the structure X—Y, Y—X—Y and X—Y—X where X in a polyalkylene oxide and Y is a biodegradable polyester (e.g., PLG-PEG-PLG) and PLURONICs such as F-127, 10° C.- 15° C.; L-122, 19° C.; L-92, 26° C.; L-81, 20° C.; and L-61, 24° C.

Representative examples of patents relating to thermally gelling polymers and the preparation include U.S. Pat. Nos; 6,451,346; 6,201,072; 6,117,949; 6,004,513; 5,702;717; and 5,484,610; and PCT Publication Nos. WO 99/07343; WO 99/18142; WO 03/17972; WO 01/82970; WO 00/18821; WO 97/15287; WO 01/41735; WO 00/00222 and WO 00/38651.

Paclitaxel derivatives may be linked by occlusion in the matrices of the polymer, bound by covalent linkages, or encapsulated in microcapsules. Within certain imbodiments of the invention, therapeutic compositions are provided in non-capsular formulations such as microspheres (ranging from nanometers to micrometers in size), pastes, threads of various size, films, or sprays. In one aspect, the paclitaxel derivative may be incorporated into biodegradable magnetic nanospheres. The nanospheres may be used, for example, to replenish a paclitaxel derivative into an implanted intravascular device, such as a stent containing a weak magnetic alloy (see, e.g., Z. Forbes, B.B. Yellen, G. Friedman, K. Barbee. "An approach to targeted drug delivery based on uniform magnetic fields," IEEE Trans. Magn. 39(5): 3372-3377 (2003)).

Within certain aspects of the present invention, therapeutic compositions may be fashioned in the form of microspheres, microparticles and/or nanoparticles having any size ranging from about 30 nm to 500 μm, depending upon the particular use. These compositions can be formed by spray-drying methods, milling methods, coacervation methods, W/O emulsion methods, W/O/W emulsion methods, and solvent evaporation methods. In other aspects, these compositions can include microemulsions, emulsions, liposomes and micelles. Alternatively, such compositions may also be readily applied as a "spray", which solidifies into a film or coating for use as a device/implant surface coating or to line the tissues of the implantation site. Such, sprays may be prepared from microspheres of a wide array of sizes, including for example, from 0.1 μm to 3 μm, from 10 μm to 30 μm, and from 30 μm to 100 μm.

Therapeutic compositions of the present invention may also be prepared in a variety of "paste" or gel forms. For example, within one embodiment of the invention, therapeutic compositions are provided which are liquid at one temperature (e.g., temperature greater than 37° C., such as 40° C., 45° C., 50° C., 55° C. or 60° C.), and solid or semi-solid at another temperature (e.g., ambient body temperature, or any temperature lower than 37° C.). Such "thermopastes" maybe readily made utilizing a variety of techniques (see, e.g., PCT Publication WO 98/24427). Other pastes may be applied as a liquid, which solidify in vivo due to dissolution of a water-soluble component of the paste and precipitation of encapsulated drug into the aqueous body environment. These "pastes" and "gels" containing paclitaxel derivatives are particularly useful for application to the surface of tissues that will be in contact with the implant or device.

Within yet other aspects of the invention, the therapeutic compositions of the present invention may be formed as a film or tube. These films or tubes can be porous or non-porous. Preferably, such films or tubes are generally less than 5, 4, 3, 2, or 1 mm thick, more preferably less than 0.75 mm, 0.5 mm, 0.25 mm, or, 0.10 mm thick. Films or tubes can also be generated of thicknesses less than 50 μm, 25 μm or 10 μm. Such films are preferably flexible with a good tensile strength (e.g., greater than 50, preferably greater than 100, and more preferably greater than 150 or 200 N/cm$^2$), good adhesive properties (i.e., adheres to moist or wet surfaces), and have controlled permeability. Paclitaxel derivatives contained in polymeric films are particularly useful for application to the surface of a stent as well as to the surface of tissue.

Within further aspects of the present invention, polymeric carriers are provided which are adapted to contain and release a hydrophobic fibrosis-inhibiting compound, and/or the carrier containing the hydrophobic compound in combination with a carbohydrate, protein or polypeptide. Within certain embodiments, the polymeric carrier contains or comprises regions, pockets, or granules of one or more hydrophobic compounds. For example, within one embodiment of the invention, hydrophobic compounds may be incorporated within a matrix which contains the hydrophobic fibrosis-inhibiting compound, following by incorporation of the matrix within the polymeric carrier. A variety of matrices can be utilized in this regard, including for example, carbohydrates and polysaccharides such as starch, cellulose, dextran, methylcellulose, sodium alginate, heparin, chitosan and hyaluronic acid, proteins or polypeptides such as albumin, collagen and gelatin. Within alternative embodiments, hydrophobic compounds may be contained within a hydrophobic core, and this core contained within a hydrophilic shell.

Other carriers that may likewise be utilized to contain and deliver fibrosis-inhibiting paclitaxel derivatives described herein include: hydroxypropyl cyclodextrin (Cserhati and Hollo, *Int. J. Pharm.* 108:69-75, 1994), liposomes (see, e.g., Sharma et al., *Cancer Res. 53*:5877-5881, 1993; Sharma and Straubinger, *Pharm. Res. 11*(60):889-896, 1994; WO 93/18751; U.S. Pat. No. 5,242,073), liposome/gel (WO 94/26254), nanocapsules (Bartoli et al., *J. Microencapsulation* 7(2):191-197, 1990), micelles (Alkan-Onyuksel et al., *Pharm. Res.* 11(2):206-212, 1994); implants (Jampel et al., *Invest. Ophthalm. Vis. Science* 34(11):3076-3083, 1993; Walter et al., *Cancer Res.* 54:22017-2212, 1994), nanoparticles (Violante and Lanzafame PAACR), nanoparticles—modified (U.S. Pat. No. 5,145,684), nanoparticles (surface modified) (U.S. Pat. No. 5,399,363), micelle (surfactant) (U.S. Pat. No. 5,403,858), synthetic phospholipid compounds (U.S. Pat. No. 4,534,899), gas borne dispersion (U.S. Pat. No. 5,301,664), liquid emulsions, foam, spray, gel, lotion, cream, ointment, dispersed vesicles, particles or droplets solid- or liquid- aerosols, microemulsions (U.S. Pat. No. 5,330,756), polymeric shell (nano- and micro- capsule) (U.S. Pat. No. 5,439,686), emulsion (Tarr et al., *Pharm Res.* 4:62-165, 1987), nanospheres (Hagan et al., *Proc. Intern. Symp. Control Rel. Bioact. Mater.* 22, 1995; Kwon et al., *Pharm Res.* 12(2):192-195; Kwon et al., *Pharm Res.* 10(7):970-974; Yokoyama et al., *J. Contr. Rel.* 32:269-277, 1994; Gref et al., *Science* 263:1600-1603, 1994; Bazile et al., *J. Pharm. Sci.* 84:493-498, 1994) and implants (U.S. Pat. No. 4,882,168).

Within another aspect of the present invention, polymeric carriers can be materials that are formed in situ. In one embodiment, the precursors can be monomers or macromers that contain unsaturated groups that can be polymerized and/or crosslinkeds. The monomers or macromers can then, for example, be injected into the treatment area or onto the surface of the treatment area and polymerized in situ using a radiation source (e.g., visible or UV light) or a free radical system (e.g., potassium persulfate and ascorbic acid or iron and hydrogen peroxide). The polymerization step can be performed immediately prior to, simultaneously to or post injection of the reagents into the treatment site. Representative examples of compositions that undergo free radical polymerization reactions are described in WO 01/44307, WO 01/68720, WO 02/072166, WO 03/043552, WO 93/17669, WO 00/64977; U.S. Pat. Nos. 5,900,245, 6,051,248, 6,083,524, 6,177,095, 6,201,065, 6,217,894, 6,639,014, 6,352,710, 6,410,645, 6,531,147, 5,567,435, 5,986,043, 6,602,975; U.S. patent application Publication Nos. 2002/012796A1, 2002/0127266A1, 2002/0151650A1, 2003/0104032A1, 2002/0091229A1, and 2003/0059906A1.

In another embodiment, the reagents can undergo an electrophilic-nucleophilic reaction to produce a crosslinked matrix. For example, a 4-armed thiol derivatized polyethylene glycol can be reacted with a 4 armed NHS-derivatized polyethylene glycol under basic conditions (pH>about 8). Representative examples of compositions that undergo electrophilic-nucleophilic crosslinking reactions are described in U.S. Pat. Nos: 5,752,974; 5,807,581; 5,874,500; 5,936,035; 6,051,648; 6,165,489; 6,312,725; 6,458,889; 6,495,127; 6,534,591; 6,624,245; 6,566,406; 6,610,033; 6,632,457; PCT Application Published Nos. WO 04/060405 and WO 04/060346. Other examples of in situ forming materials that can be used include those based on the crosslinking of proteins (described in U.S. Pat. Nos. RE38158; 4,839,345; 5,514,379, 5,583,114; 6,458,147; 6,371,975; U.S. Publication Nos. 2002/0161399; 2001/0018598 and PCT Publication Nos: WO 03/090683; WO 01/45761; WO 99/66964 and WO 96/03159).

Other examples of compositions and methods for applying (e.g., coating) these compositions to medical devices are described in U.S. Pat. Nos: 6,610,016; 6,358,557; 6,306,176; 6,110,483; 6,106,473; 5,997,517; 5,800,412; 5,525,348; 5,331,027; 5,001,009; 6,562,136; 6,406,754; 6,344,035; 6,254,921; 6,214,901; 6,077,698; 6,603,040; 6,278,018; 6,238,799; 6,096;726, 5,766,158; 5,599,576, 4,119, 094; 4,100,309; 6;599,558; 6,369,168; 6,521,283; 6,497,916; 6,251,964; 6,225,431; 6,087,462; 6,083,257; 5,739,237; 5,739,236; 5,705,583; 5,648,442; 5,645,883; 5,556,710; 5,496,581; 4,689,386; 6,214,115; 6,090,901; 6,599,448; 6,054,504; 4,987,182; 4,847,324; and 4,642,267; U.S. patent application Publication Nos. 2002/0146581, 2003/0129130, 2003/0129130, 2001/0026834; 2003/0190420; 2001/0000785; 2003/0059631; 2003/0190405; 2002/0146581; 2003/020399; 2001/0026834; 2003/0190420; 2001/0000785; 2003/0059631; 2003/0190405; and 2003/020399; and PCT Publication Nos. WO 02/055121; WO 01/57048; WO 01/52915; and WO 01/01957.

Within another aspect of the invention, the paclitaxel derivative can be delivered with a non-polymeric agent. These non-polymeric carriers can include sucrose derivatives (e.g., sucrose acetate isobutyrate, sucrose oleate), sterols such as cholesterol, stigmasterol, β-sitosterol, and estradiol; cholesteryl esters such as cholesteryl stearate; $C_{12}$-$C_{24}$ fatty acids such as lauric acid, myristic acid, palmitic acid, stearic acid, arachidic acid, behenic acid, and lignoceric acid; $C_{18}$-$C_{36}$ mono-, di-and triacylglycerides such as glyceryl monooleate, glyceryl monolinoleate, glyceryl monolaurate; glyceryl monodocosanoate, glyceryl monomyristate, glyceryl monodicenoate, glyceryl dipalmitate, glyceryl didocosanoate, glyceryl dimyristate, glyceryl didecenoate, glyceryl tridocosanoate, glyceryl trimyristate, glyceryl tridecenoate, glycerol tristearate and mixtures thereof; sucrose fatty acid esters such as sucrose distearate and sucrose palmitate; sorbitan fatty acid esters such as sorbitan monostearate, sorbitan monopalmitate and sorbitan tristearate; $C_{16}$-$C_{18}$ fatty alcohols such as cetyl alcohol, myristyl alcohol, stearyl alcohol, and cetostearyl alcohol; esters of fatty alcohols and fatty acids such as cetyl palmitate and cetearyl palmitate; anhydrides of fatty acids such as stearic anhydride; phospholipids including phosphatidylcholine (lecithin), phosphatidylserine, phosphatidylethanolamine, phosphatidylinositol, and lysoderivatives thereof; sphingosine and derivatives thereof; spingomyelins such as stearyl, palmitoyl, and tricosanyl spingomyelins; ceramides such as stearyl and palmitoyl ceramides; glycosphingolipids; lanolin and lanolin alcohols, calcium phosphate, sintered and unscintered hydoxyapatite, zeolites; and combinations and mixtures thereof.

Representative examples of patents relating to non-polymeric delivery systems and the preparation include U.S. Pat. Nos. 5,736,152; 5,888,533; 6,120,789; 5,968,542; and 5,747,058.

The paclitaxel derivative may be delivered as a solution. The paclitaxel derivative can be incorporated directly into the solution to provide a homogeneous solution or dispersion. In certain embodiments, the solution is an aqueous solution. The aqueous solution may further include buffer salts, as well as viscosity modifying agents (e.g., hyaluronic acid, alginates, carboxymethylcelluloe (CMC), and the like). In another aspect of the invention, the solution can include a biocompatible solvent such as ethanol, DMSO, glycerol, PEG-200; PEG-300 or NMP.

Within another aspect of the invention, the paclitaxel derivative can further comprise a secondary carrier. The secondary carrier can be in the form of microspheres (e.g., PLGA, PLLA, PDLLA, PCL, gelatin, polydioxanone, poly(alkylcyanoacrylate)), nanospheres (PLGA, PLLA, PDLLA, PCL, gelatin, polydioxanone, poly(alkylcyanoacrylate)), liposomes, emulsions, microemulsions, micelles (SDS, block copolymers of the form X—Y, X—Y—X or Y—X—Y, R—$(Y—X)_n$, R—$(X—Y)_n$ where X is a polyalkylene oxide (e.g., poly(ethylene oxide, poly(propylene oxide, block copolymers of poly(ethylene oxide) and poly(propylene oxide) and Y is a polyester (e.g., polyester can comprise the residues of one or more of the monomers selected from lactide, lactic acid, glycolide, glycolic acid, ε-caprolactone, gamma-caprolactone, hydroxyvaleric acid, hydroxybutyric acid, beta-butyrolactone, gamma-butyrolactone, gamma-valerolactone, γ-decanolactone, δ-decanolactone, trimethlene carbonate, 1,4-dioxane-2-one or 1,5-dioxepan-2one). R is a multifunctional initiator and copolymers as well as blends thereof.), zeolites or cyclodextrins.

Within another aspect of the invention, these paclitaxel derivative/secondary carrier compositions can be a) incorporated directly into or onto the device, b) incorporated into a solution, c) incorporated into a gel or viscous solution, d) incorporated into the composition used for coating the device or e) incorporated into or onto the device following coating of the device with a coating composition.

For example, paclitaxel derivative loaded PLGA microspheres can be incorporated into a polyurethane coating solution which is then coated onto the device.

In yet another example, the device can be coated with a polyurethane and then allowed to partially dry such that the surface is still tacky. A particulate form of the paclitaxel derivative or paclitaxel derivative/secondary carrier can be applied to all or a portion of the tacky coating after which the device is dried.

In yet another example, the device can be coated with one of the coatings described above. A thermal treatment process can then be used to soften the coating, after which the paclitaxel derivative or the paclitaxel derivative/secondary carrier is applied to the entire device or to a portion of the device (e.g., outer surface)

Within another aspect of the invention, the coated device which inhibits or reduces an in vivo fibrotic reaction is further coated with a compound or compositions which delay the release of and/or activity of the paclitaxel derivative. Representative examples of such agents include biologically inert materials such as gelatin, PLGA/MePEG film, PLA, polyurethanes, silicone rubbers, surfactants, lipids, or polyethylene glycol, as well as biologically active materials such as heparin (e.g., to induce coagulation).

For example, in one embodiment of the invention, the active agent on the device is top-coated with a physical barrier. Such barriers can include non-degradable materials or biodegradable materials such as gelatin, PLGA/MePEG film, PLA, or polyethylene glycol among others. In one embodiment, the rate of diffusion of the therapeutic agent in barrier coat is slower that the rate of diffusion of the therapeutic agent in the layer. In the case of PLGA/MePEG, once the PLGA/Me PEG becomes exposed to the bloodstream, the MePEG can dissolve out of the PLGA, leaving channels through the PLGA layer to an underlying layer containing the paclitaxel derivative, which then can then diffuse into the vessel wall and initiate its biological activity.

In another embodiment of the invention, a particulate form of the active agent may be coated onto the stent (or any of the devices described below) using a polymer (e.g., PLG, PLA, or a polyurethane). A second polymer, that dissolves slowly or degrades (e.g., MePEG-PLGA or PLG) and that does not contain the active agent, may be coated over the first layer. Once the top layer dissolves or degrades, it exposes the under coating which allows the active agent to be exposed to the treatment site or to be released from the coating.

Within another aspect of the invention, the outer layer of the coating of a coated device, which inhibits an in vivo fibrotic response, is further treated to crosslink the outer layer of the coating. This can be accomplished by subjecting the coated device to a plasma treatment process. The degree of crosslinking and nature of the surface modification can be altered by changing the RF power setting, the location with respect to the plasma, the duration of treatment as well as the gas composition introduced into the plasma chamber.

Protection of a biologically active surface can also be utilized by coating the device surface with an inert molecule that prevents access to the active site through steric hindrance, or by coating the surface with an inactive form of the paclitaxel derivative, which is later activated. For example, the device can be coated with an enzyme, which causes either release of the paclitaxel derivative or activates the paclitaxel derivative.

In another embodiment, the device is coated with a paclitaxel derivative and then further coated with a composition that comprises an anticoagulant such as heparin. As the antlcoagulant dissolves away, the anticoagulant activity slows or stops, and the newly exposed paclitaxel derivative is available to inhibit or reduce fibrosis from occurring in the adjacent tissue.

The device can be coated with an inactive form of the paclitaxel derivative, which is then activated once the device is deployed. Such activation can be achieved by injecting another material into the treatment area after the device (as described below) is deployed or after the paclitaxel derivative has been administered to the treatment area (via, e.g., injections, spray, wash, drug delivery catheters or balloons). For example, the device can be coated with an inactive form of the paclitaxel derivative. Once the device is deployed, the activating substance is injected or applied into or onto the treatment site where the inactive form of the paclitaxel derivative has been applied. For example, a device can be coated with a biologically active paclitaxel derivative and a first substance having moieties that capable of forming an ester bond with another material. The coating can be covered with a second substance such as polyethylene glycol. The first and second substances can react to form an ester bond via, e.g., a condensation reaction. Prior to the deployment of the device, an esterase is injected into the treatment site around the outside of the device, which can cleave the bond between the ester and the paclitaxel derivative, allowing the agent to initiate fibrosis-inhibition.

In another aspect, a medical device may include a plurality of reservoirs within its structure, each reservoir configured to house and protect a therapeutic drug. The reservoirs may be formed from divets in the device surface or micropores or channels in the device body. In one aspect, the reservoirs are formed from voids in the structure of the device. The reservoirs may be coated with a single type of drug or more than one type of drug. The drug(s) may be formulated with a carrier (e.g., a polymeric or non-polymeric material) that is coated on the reservoirs. The coated reservoir can function as a drug delivery depot which can release drug over a period of time dependent on the release kinetics of the drug from the carrier. In certain embodiments, the reservoir may be coated with a plurality of layers. Each layer may include a different drug having a particular amount (dose) of drug, and each layer may have a different composition to further tailor the amount of drug that is released from the substrate. The multi-layered carrier may further include a barrier layer that prevents release of the drug(s). The barrier layer can be used, for example, to control the direction that the drug elutes from the void. In a preferred embodiment, this drug-coated medical device may further comprise a paclitaxel derivative in one or more reservoirs.

Within certain embodiments of the invention, the therapeutic compositions may also comprise additional ingredients such as surfactants (e.g., PLURONICS, such as F-127, L-122, L-101, L-92, L-81, and L-61), anti-inflammatory agents (e.g., dexamethasone or aspirin), anti-thrombotic agents (e.g., heparin, high activity heparin, heparin quaternary amine complexes (e.g., heparin benzalkonium chloride complex)), anti-infective agents (e.g., 5-fluorouracil, triclosan, rifamycim, and silver compounds), preservatives, anti-oxidants and/ or anti-platelet agents.

Within certain embodiments of the invention, the therapeutic agent or carrier can also comprise radio-opaque, echogenic materials and magnetic resonance imaging (MRI) responsive materials (i.e., MRI contrast agents) to aid in visualization of the device under ultrasound, fluoroscopy and/or MRI. For example, a device may be made with or coated with a composition which is echogenic or radiopaque (e.g., made with echogenic or radiopaque with materials such as powdered tantalum, tungsten, barium carbonate, bismuth oxide, barium sulfate, metrazimide, iopamidol, iohexol, iopromide, iobitridol, iomeprol, iopentol, ioversol, ioxilan, iodixanol, iotrolan, acetrizoic acid derivatives, diatrizoic acid derivatives, iothalamic acid derivatives, ioxithalamic acid derivatives, metrizoic acid derivatives, iodamide, lypophylic agents, iodipamide and ioglycamic acid or, by the addition of microspheres or bubbles which present an acoustic interface). Visualization of a device by ultrasonic imaging may be achieved using an echogenic coating. Echogenic coatings are described in, e.g., U.S. Pat. Nos. 6,106,473 and 6,610,016. For visualization under MRI, contrast agents (e.g., gadolinium (III) chelates or iron oxide compounds) may be incorporated into or onto the device, such as, for example, as a component in a coating or within the void volume of the device (e.g., within a lumen, reservoir, or within the structural material used to form the device). In some embodiments, a medical device may include radio-opaque or MRI visible markers (e.g., bands) that may be used to orient and guide the device during the implantation procedure.

In another embodiment, these agents can be contained within the same coating layer as the therapeutic agent or they may be contained in a coating layer (as described above) that is either applied before or after the therapeutic agent containing layer.

The medical implants may, alternatively, or in addition, be visualized under visible light, using fluorescence, or by other spectroscopic means. Visualization agents that can be included for this purpose include dyes, pigments, and other colored agents. In one aspect, the medical implant may further include a colorant to improve visualization of the implant in vivo and/or ex vivo. Frequently, implants can be difficult to visualize upon insertion, especially at the margins of implant. A coloring agent can be incorporated into a medical implant to reduce or eliminate the incidence or severity of this problem. The coloring agent provides a unique color, increased contrast, or unique fluorescence characteristics to the device. In one aspect, a solid implant is provided that includes a colorant such that it is readily visible (under visible light or using a fluorescence technique) and easily differentiated from its implant site. In another aspect, a colorant can be included in a liquid or semi-solid composition. For example, a single component of a two component mixture may be colored, such that when combined ex-vivo or in-vivo, the mixture is sufficiently colored.

The coloring agent may be, for example, an endogenous compound (e.g., an amino acid or vitamin) or a nutrient or food material and may be a hydrophobic or a hydrophilic compound. Preferably, the colorant has a very low or no toxicity at the concentration used. Also preferred are colorants that are safe and normally enter the body through absorption such as β-carotene. Representative examples of colored nutrients (under visible light) include fat soluble vitamins such as Vitamin A (yellow); water soluble vitamins such as Vitamin B12 (pink-red) and folic acid (yellow-orange); carotenoids such as β-carotene (yellow-purple) and lycopene (red). Other examples of coloring agents include natural product (berry and fruit) extracts such as anthrocyanin (purple) and saffron extract (dark red). The coloring agent may be a fluorescent or phosphorescent compound such as α-tocopherolquinol (a Vitamin E derivative) or L-tryptophan. Derivatives, analogues, and isomers of any of the above colored compound also may be used. The method for incorporating a colorant into an implant or therapeutic composition may be varied depending on the properties of and the desired location for the colorant. For example, a hydrophobic colorant may be selected for hydrophobic matrices. The colorant may be incorporated into a carrier matrix, such as micelles. Further, the pH of the environment may be controlled to further control the color and intensity.

In one aspect, the composition of the present invention include one or more coloring agents, also referred to as dyestuffs, which will be present in an effective amount to impart observable voloration to the composition, e.g., the gel. Example of coloring agents include dyes suitable for food such as those known as F.D. & C. dyes and natural coloring agents such as grape skin extract, beet red powder, beta carotene, annato, carmine, turmeric, paprika, and so forth. Derivatives, analogues, and isomers of any of the above colored compound also may be used. The method for incorporating a colorant into an implant or therapeutic composition may be varied depending on the properties of and the desired location for the colorant. For example, a hydrophobic color and may be selected for hydrophobic matrices. The colorant may be incorporated into a carrier matrix, such as micelles. Further, the pH of the environment may be controlled to further control the color and intensity.

In one aspect, the compositions of the present invention include one or more preservatives or bacteriostatic agents, present in an effective amount to preserve the composition and/or inhibit bacterial growth in the composition, for example, bismuth tribromophenate, methyl hydroxybenzoate, bacitracin, ethyl hydroxybenzoate, propyl hydroxybenzoate, erythromycin, 5-fluorouracil, methotrexate, doxorubicin, mitoxantrone, rifamycin, chlorocresol, benzalkonium chlorides, and the like. Examples of the preservative include paraoxybenzoic acid esters, chlorobutanol, benzylalcohol, phenethyl alcohol, dehydroacetic acid, sorbic acid, etc. In one aspect, the compositions of the present invention include one or more bactericidal (also known as bacteriacidal) agents.

In one aspect, the compositions of the present invention include one or more antioxidants, present in an effective amount. Examples of the antioxidant include sulfites, alpha-tocopherol and ascorbic acid.

Within certain aspects of the present invention, the therapeutic composition should be biocompatible, and release one or more paclitaxel derivatives over a period of several hours, days, or, months. As described above, "release of an agent" refers to any statistically significant presence of the agent, or a subcomponent thereof, which has disassociated from the compositions. The compositions of the present invention may release the paclitaxel derivative at one or more phases, the one or more phases having similar or different performance (e. g., release) profiles. The therapeutic agent may be made available to the tissue at amounts which may be sustainable, intermittent, or continuous; in one or more phases; and/or rates of delivery; effective to reduce or inhibit any one or more components of fibrosis (or scarring), including: formation of new blood vessels (angiogenesis), migration and proliferation of connective tissue cells (such as fibroblasts or smooth muscle cells), deposition of extracellular matrix (ECM), and remodeling (maturation and organization of the fibrous tissue).

Thus, release rate may be programmed to impact fibrosis (or scarring) by releasing a paclitaxel derivative at a time such that at least one of the components of fibrosis is inhibited or reduced. Moreover, the predetermined release rate may reduce agent loading and/or concentration as well as potentially providing minimal drug washout and thus, increases efficiency of drug effect. Any one of the at least one paclitaxel derivatives may perform one or more functions, including inhibiting the formation of new blood vessels (angiogenesis), inhibiting the migration and proliferation of connective tissue cells (such as fibroblasts or smooth muscle cells), inhibiting the deposition of extracellular matrix (ECM), and inhibiting remodeling (maturation and organization of the fibrous tissue). In one embodiment, the rate of release may provide a sustainable level of the paclitaxel derivative to the susceptible tissue site. In another embodiment, the rate of release is substantially constant. The rate may decrease and/or increase over time, and it may optionally include a substantially non-release period. The release rate may comprise a plurality of rates. In an embodiment, the plurality of release rates may include rates selected from the group consisting of substantially constant, decreasing, increasing, substantially non-releasing.

The total amount of paclitaxel derivative made available on, in or near the device may be in an amount ranging from about 0.01 μg (micrograms) to about 2500 mg (milligrams). Generally, the paclitaxel derivative may be in the amount ranging from 0.01 μg to about 10 μg; or from 10 μg to about 1 mg; or from 1 mg to about 10 mg; or from 10 mg to about 100 mg; or from 100 mg to about 500 mg; or from 500 mg to about 2500 mg.

The total surface amount of paclitaxel derivative on, in or near the device may be in an amount ranging from less than 0.01 μg to about 2500 μg per $mm^2$ of device surface area. Generally, the paclitaxel derivative may be in the amount ranging from less than 0.01 μg; or from 0.01 μg to about 10 μg; or from 10 μg to about 250 μg; or from 250 μg to about 2500 μg.

The paclitaxel derivative that is on, in or near the device may be released from the composition in a time period that may be measured from the time of implantation, which ranges from about less than 1 day to about 180 days. Generally, the release time may also be from about less than 1 day to about 7 days; from 7 days to about 14 days; from 14 days to about 28 days; from 28 days to about 56 days; from 56 days to about 90 days; from 90 days to about 180 days. In certain embodiments, the drug is released in effective concentrations for a period ranging from about 1 to about 90 days.

The amount of paclitaxel derivative released from the composition as a function of time may be determined based on the in vitro release characteristics of the agent from the composition. The in vitro release rate may be determined by placing the paclitaxel derivative within the composition or device in an appropriate buffer such as 0.1M phosphate buffer (pH 7.4)) at 37° C. Samples of the buffer solution are then periodically removed for analysis by HPLC, and the buffer is replaced to avoid any saturation effects.

Based on the in vitro release rates, the release of paclitaxel derivative per day may range from an amount ranging from about 0.01 μg (micrograms) to about 2500 mg (miiligrams). Generally, the paclitaxel derivative that may be released in a day may be in the amount ranging from 0.01 μg to about 10 μg; or from 10 μg to about 1 mg; or from 1 mg to about 10 mg; or from 10 mg to about 100 mg; or from 100 mg to about 500 mg; or from 500 mg to about 2500 mg.

In one embodiment, the paclitaxel derivative is made available to the susceptible tissue site in a programmed, sustained, and/or controlled manner which results in increased efficiency and/or efficacy. Further, the release rates may vary during either or both of the initial and subsequent release phases. There may also be additional phase(s) for release of the same substance(s) and/or different substance(s).

Further, therapeutic compositions and devices of the present invention should preferably be have a stable shelf-life for several months and capable of being produced and maintained under sterile conditions. Many pharmaceuticals are manufactured to be sterile and this criterion is defined by the USP XXII <1211>. The term "USP" refers to U.S. Pharmacopeia (see www.usp.org, Rockville, Md.). Sterilization may be accomplished by a number of means accepted in the industry and listed in the USP XXII <1211>, including gas sterilization, ionizing radiation or, when appropriate, filtration. Sterilization may be maintained by what is termed asceptic processing, defined also in USP XXII <1211>. Acceptable gases used for gas sterilization include ethylene oxide. Acceptable radiation types used for ionizing radiation methods include gamma, for instance from a cobalt 60 source and electron beam. A typical dose of gamma radiation is 2.5 MRad. Filtration may be accomplished using a filter with suitable pore size, for example 0.22 μm and of a suitable material, for instance polytetrafluoroethylene (e.g., TEFLON from E. I. DuPont De Nemours and Company, Wilmington, Del.).

D. Methods of Utilizing Stent Devices

There are numerous types of stents where the occurrence of a fibrotic reaction will adversely affect the functioning of the device or the biological problem for which the device was implanted or used. The coating of paclitaxel derivatives such as paclitaxel derivatives onto or incorporation of paclitaxel derivatives into stent devices provides a solution to the clinical problems that can be encountered with these devices.

Generally, stents are inserted in a similar fashion regardless of the site or the disease being treated. Briefly, a preinsertion examination, usually a diagnostic imaging procedure, endoscopy, or direct visualization at the time of surgery, is generally first performed in order to determine the appropriate positioning for stent insertion. A guidewire is then advanced through the lesion or proposed site of insertion, and over this is passed a delivery catheter which allows a stent in its collapsed form to be inserted. Intravascular stents may be inserted into an artery such as the femoral artery in the groin and advanced through the circulation under radiological guidance until they reach the anatomical location of the plaque in the coronary or peripheral circulation. Typically, stents are capable of being compressed, so that they can be inserted through tiny cavities via small catheters, and then expanded to a larger diameter once they are at the desired location. The delivery catheter then is removed, leaving the stent standing on its own as a scaffold. Once expanded, the stent physically forces the walls of the passageway apart and holds them open. A post insertion examination, usually an x-ray, is often utilized to confirm appropriate positioning.

Stents are typically maneuvered into place under, radiologic or direct visual control, taking particular care to place the stent precisely within the vessel being treated. In certain aspects the stent can further include a radio-opaque, echogenic material, or MRI responsive material (e.g., MRI contrast agent) to aid in visualization of the device under ultrasound, fluoroscopy and/or magnetic resonance imaging. The radio-opaque or MRI visible material may be in the form of one or more markers (e.g., bands of material that are disposed on either end of the stent) that may be used to orient and guide the device during the implantation procedure.

In another aspect, the paclitaxel derivative or a composition comprising a paclitaxel derivative may be infiltrated into or onto tissue surrounding the stent. Alternatively, the tissue cavity into which the stent is placed can be treated with a paclitaxel derivative prior to, during, or after the procedure.

Infiltration of paclitaxel derivatives or compositions comprising paclitaxel derivatives may be accomplished, for example, using drug-delivery catheters for local, regional or systemic delivery of fibrosis inhibiting agents to the tissue surrounding the device. The drug delivery catheter may be advanced through the circulation of inserted directly into tissues under radiological guidance (e.g., magnetic, ultrasonic or MRI) until they reach the desired anatomical location. The paclitaxel derivative can then be released from the catheter lumen in high local concentrations in order to deliver therapeutic doses of the drug to the tissue surrounding the device or implant. Alternatively, or in addition, the paclitaxel derivative or composition comprising the paclitaxel derivative may be injected directly into the treatment site (e.g., into the space around the stent or into tissue surrounding the stent) under endoscopic vision.

Other methods of infiltrating paclitaxel derivatives into the treatment site include (a) topical application of the paclitaxel derivative into the anatomical space where the device will be placed (particularly useful for this embodiment is the use of polymeric carriers which release the anti-fibrosing agent over a period ranging from several hours to several weeks. Compositions that can be used for this application include, e.g., fluids, microspheres, pastes, gels, hydrogels, crosslinked gels, microparticulates, sprays, aerosols, solid implants and other formulations which release a fibrosis inhibiting agent into the region where the device or implant will be implanted); (b) microparticulate forms of the therapeutic agent are also useful for directed delivery into the implantation site; (c) sprayable collagen-containing formulations such as COSTASIS (from Angiotech Pharmaceuticals, Inc., Canada), either alone, or loaded with a paclitaxel derivative, applied to the implantation site (or the implant/device surface); (d) sprayable PEG-containing formulations such as COSEAL (Angiotech Pharmaceuticals, lnc.), SPRAYGEL or DURASEAL (both from Confluent Surgical, Inc., Boston, Mass.), FOCALSEAL (Genzyme Corporation, Cambridge, Mass.) either alone, or loaded with a paclitaxel derivative, applied to the implantation site (or the implant/device surface); (e) fibrin-containing formulations such as FLOSEAL or TISSEEL (both from Baxter Healthcare Corporation, Fremont, Calif.), either alone, or loaded with a paclitaxel derivative, applied to the implantation site (or the implant/device surface); (f) hyaluronic acid-containing formulations such as RESTYLANE or PERLANE (both from Q-Med AB, Sweden), HYLAFORM (Inamed Corporation (Santa Barbara, Calif.)), SYNVISC (Biomatrix, Inc., Ridgefield, N.J.), SEPRAFILM or SEPRACOAT (both from Genzyme Corporation, Cambridge, Mass.), INTERGEL (Lifecore Biomedical) loaded with a paclitaxel derivative applied to the implantation site (or the implant/device surface); (g) polymeric gels for surgical implantation such as REPEL (Life Medical Sciences, Inc., Princeton, N.J.) or FLOGEL (Baxter Healthcare Corporation) loaded with a paclitaxel derivative applied to the implantation site (or the implant/device surface); (h) surgical adhesives containing cyanoacrylates such as DERMABOND (Johnson & Johnson, Inc., New Brunswick, N.J.), INDERMIL (U.S. Surgical Company, Norwalk, Conn.), GLUSTITCH (Blacklock Medical Products Inc., Canada), TISSUMEND II (Veterinary Products Laboratories,, Phoenix, Ariz.), VETBOND (3M Company, St. Paul, Minn.), HISTOACRYL BLUE (Davis & Geck, St. Louis, Mo.) and ORABASE SMOOTHE N-SEAL Liquid Protectant (Colgate-Palmolive Company, New York, N.Y.), either alone, or loaded with a paclitaxel derivative, applied to the implantation site (or the implant/device surface).

Drugs and Dosage

As described above, any paclitaxel derivative described above can be combined with a stent device. Further, stent devices may be adapted to release a paclitaxel derivative that inhibits one or more of the four general components of the process of fibrosis (or scarring), including: formation of new blood vessels (angiogenesis), migration and proliferation of connective tissue cells (such as fibroblasts or smooth muscle cells), deposition of extracellular matrix (ECM), and remodeling (maturation and organization of the fibrous tissue). By inhibiting one or more of the components of fibrosis (or scarring), the overgrowth of granulation tissue may be inhibited or reduced.

As stent devices are made in a variety of configurations and sizes, the exact dose administered will vary with device size, surface area and design. However, certain principles can be applied in the application of this art. Drug dose can be calculated as a function of dose per unit area (of the portion of the device being coated), total drug dose administered, and appropriate surface concentrations of active drug can be determined. Drugs are to be used at concentrations that range from several times more than 10%, 5%, or even less than 1% of the concentration typically used in a single chemotherapeutic systemic dose application.

Several examples of agents for use with stents include the following: 9-deoxotaxol, 7-deoxy-9-deoxotaxol, and 10-desacetoxy-7-deoxy-9-deoxotaxol.

Regardless of the method of application of the drug to the intravascular device, the exemplary agents, used alone or in combination, should be administered under the following dosing guidelines. The total dose of agent in or on the device may be in the range of about 0.01 μg-10 μg, or 10 μg-250 μg, or 250 μg-1 mg, or 1 mg-10 mg, or 10 mg-250 mg, or 250 mg-1000 mg, or 1000 mg-2500 mg. The dose of paclitaxel derivative per unit area of device surface to which the agent is applied may be in the range of about 0.01 $\mu g/mm^2$-1 $\mu g/mm^2$, or 1 $\mu g/mm^2$-10 $\mu g/mm^2$, or 10 $\mu g/mm^2$-250 $\mu g/mm^2$; 250 $\mu g/mm^2$-1000 $\mu g/mm^2$, or 1000 $\mu g/mm^2$-2500 $\mu g/mm^2$.

Provided below are exemplary dosage ranges for various paclitaxel derivatives that can be used in conjunction with stent devices in accordance with the invention. A) paclitaxel derivatives (e.g., 9-deoxotaxol, 7-deoxy-9-deoxotaxol, and 10-desacetoxy-7-deoxy-9-deoxotaxol): total dose not to exceed 10 mg (range of 0.1 μg to 10 mg); preferred 1 μg to 3 mg. The dose per unit area of the device of 0.1 μg-10 μg per $mm^2$; preferred dose of 0.25 $\mu g/mm^2$-5 $\mu g/mm^2$. Minimum concentration of $10^{-8}$-$10^{-4}$ M of paclitaxel is to be maintained on the device surface.

It should be apparent to one of skill in the art that potentially any paclitaxel derivative described above can be utilized alone; or in combination, in the practice of this embodiment. In various aspect, the present invention provides a medical device contain a paclitaxel derivative as described herein in a dosage as set forth above.

The following examples are offered by way of illustration, and not by way of limitation.

EXAMPLES

Example 1

Parylene Coating

The metallic portion of a coronary stent is washed by dipping it into HPLC grade isopropanol. The cleaned device is then coated with a parylene coating using a parylene coater and either di-p-xylylene or dichloro-di-p-xylylene as the coating feed material. This procedure may be used to coat other types of stents that include a metallic portion (e.g., peripheral stents, covered stents).

Example 2

Paclitaxel Coating—End Coating

Solutions are prepared by dissolving 9-deoxotaxol in 5 mL HPLC grade THF. The ends of a parylene coated coronary stent (prepared as in Example 1) are then dipped into the paclitaxel derivative/THF solution. After various incubation times, the devices are removed and dried in a forced air oven (50° C.). The device is then further dried in a vacuum oven overnight. The amount of 9-deoxotaxol used in each solution is varied such that the amount of 9-deoxotaxol coated onto the ends of the device is in the range of 0.06 $mg/mm^2$ to 10 $mg/mm^2$. This procedure may be used to coat other types of devices that include a metallic portion (e.g., peripheral stents, covered stents).

Example 3

Paclitaxel Coating—Complete Coating

Paclitaxel derivative solutions are prepared by dissolving 9-deoxotaxol in 5 mL HPLC grade THF. A parylene coated coronary stent (as prepared in Example 1) is then dipped entirely into the paclitaxel/THF solution. After various incubation times, the device is removed and dried in a forced air oven (50° C.). The device is then further dried in a vacuum oven overnight. The amount of paclitaxel used in each solution is varied such that the amount of paclitaxel coated onto the ends of the device is in the range of 0.06 $mg/mm^2$ to 10 $mg/mm^2$. In addition to paclitaxel, the following are exemplary compounds that may be also used to coat the device: 7-deoxy-9-deoxotaxol and 10-desacetoxy-7-deoxy-9-deoxotaxol. This procedure may be used to coat other types of parylene coated devices that include a metallic portion (e.g., peripheral stents, covered stents).

Example 4

Application of a Parylene Overcoat

A paclitaxel derivative coated device is placed in a parylene coater and an additional thin layer of parylene is deposited on the paclitaxel coated device (see Example 2 or 3). The coating duration is altered such that the parylene top-coat thickness is varied such that different elution profiles of the paclitaxel may be obtained.

Example 5

Application of an Echogenic Coating Layer

DESMODUR (Bayer AG, Germany), an isocyanate prepolymer, is dissolved in a 50:50 mixture of dimethylsulfoxide and tetrahydrofuran. A paclitaxel/parylene overcoated coronary stent (prepared as in Example 4) is then dipped into the pre-polymer solution. The device is then removed and the coating is then partially dried at room temperature for 3 to 5 minutes. The device is then immersed in a beaker of water (room temperature) for 3-5 minutes to cause the polymerization reaction to occur rapidly. An echogenic coating is formed. This procedure may be used to coat other types of devices (e.g., peripheral stents, covered stents).

Example 6

Paclitaxel/Polymer Coating—End Coating

5% solutions of poly(ethylene-co-vinyl acetate) (EVA) (60% vinyl acetate) are prepared using THF as the solvent. Various amounts of 9-deoxotaxol are added to each of the EVA solutions. The ends of a coronary stent are dipped into the 9-deoxotaxol/EVA solution. After removing the end-coated device from the solution, the coating is dried by placing the device in a forced air oven (40° C.) for 3 hours. The coated device is then further dried under vacuum for 24 hours. The dip coating process may be repeated to increase the amount of polymer/9-deoxotaxol coated onto the device. In addition to 9-deoxotaxol, the following are exemplary compounds that may also be used to coat the device: 7-deoxy-9-deoxotaxol and 10-desacetoxy-7-deoxy-9-deoxotaxol. This procedure may be used to coated other types of devices (e. g., peripheral stents, nasal stents).

Example 7

Paclitaxel-Heparin Coating—End Coating

5% solutions of poly(ethylene-co-vinyl acetate) (EVA) (60% vinyl acetate) are prepared using THF as the solvent. Various amounts of 9-deoxotaxol and a solution of tridodecyl methyl ammonium chloride-heparin complex (PolySciences) are added to each of the EVA solutions. The ends of a stent device are dipped into the 9-deoxotaxol/EVA solution. After removing the end-coated device from the solution, the coating is dried by placing the device in a forced air oven (40° C.) for 3 hours. The coated stent is then further dried under vacuum for 24 hours. In addition to 9-deoxotaxol, the following are exemplary compounds that may be used to coat the device: 7-deoxy-9-deoxotaxol and 10-desacetoxy-7-deoxy-9-deoxotaxol. This procedure may be used to coated other types of devices including coronary stents and peripheral stents.

Example 8

Paclitaxel—Heparin/Heparin Coating

The uncoated portions of 9-deoxotaxol-heparin coated devices (Example 7) are dipped into a 5% EVA solution containing different amounts of a tridodecyl methyl ammonium chloride-heparin complex solution (PolySciences). After removing the end-coated device from the solution, the coating is dried by placing the stent device in a forced air oven (40° C.) for 3 hours. The coated device is then further dried under vacuum for 24 hours. This provides a device with a 9-deoxotaxol/heparin coating on the ends of the device and a heparin coating on the remaining parts of the device. In addition to 9-deoxotaxol, the following are exemplary compounds that may be used to coat the device: 7-deoxy-9-deoxotaxol and 10-desacetoxy-7-deoxy-9-deoxotaxol. This procedure may be used to coat other types of devices including coronary stents and peripheral stents.

Example 9

Paclitaxel Derative/Polymer Coating—End Coating

5% solutions of poly(styrene-co-isobutylene-styrene) (SIBS) are prepared using THF as the solvent. Various amounts of 9-deoxotaxol are added to each of the SIBS solutions. The ends of a central venous catheter device are dipped into the paclitaxel/SIBS solution. After removing the end-coated device from the solution, the coating is dried by placing the device in a forced air oven (40° C.) for 3 hours. The coated device is then further dried under vacuum for 24 hours. The dip coating process may be repeated to increase the amount of polymer/9-deoxotaxol coated onto the device. In addition to 9-deoxotaxol, the following are exemplary compounds that may be used to coat the device: 7-deoxy-9-deoxotaxol and 10-desacetoxy-7-deoxy-9-deoxotaxol. This procedure may be used to coat other types of devices including coronary stents, non-vascular stents, and peripheral stents.

Example 10

Paclitaxel Derivative/Polymer Coating—Echogenic Coating

A coated stent from Example 9 is dipped into a DESMODUR solution (50:50 mixture of dimethylsulfoxide and tetrahydrofuran). The device is then removed and the coating is then partially dried at room temperature for 3 to 5 minutes. The device is then immersed in a beaker of water (room temperature) for 3-5 minutes to cause the polymerization reaction to occur rapidly. An echogenic coating is formed. In addition to 9-deoxotaxol, the following are exemplary compounds that may be used to coat the device: 7-deoxy-9-deoxotaxol and 10-desacetoxy-7-deoxy-9-deoxotaxol.

Example 11

Polymer/Echogenic Coating

5% solutions of poly(styrene-co-isobutylene-styrene) (SIBS) are prepared using THF as the solvent. A Gl stent device is dipped into the SIBS solution. After removing the device from the solution, the coating is dried by placing the device in a forced air oven (40° C.) for 3 hours. The coated device is then further dried under vacuum for 24 hours.

The coated device is dipped into a DESMODUR solution (50:50 mixture of dimethylsulfoxide and tetrahydrofuran). The device is then removed and the coating is then partially dried at room temperature for 3 to 5 minutes. The device is then immersed in a beaker of water (room temperature) for 3-5 minutes to cause the polymerization reaction to occur rapidly. The device is dried under vacuum for 24 hours at room temperature. The ends of the coated device are immersed into a solution of 9-deoxotaxol. The device is removed and dried at 40° C. for 1 hour and then under vacuum for 24 hours.

The amount of 9-deoxotaxol absorbed by the polymeric coating may be altered by changing the 9-deoxotaxol concentration, the immersion time as well as the solvent composition of the solution. In addition to 9-deoxotaxol, the following are exemplary compounds that may be used to coat the device: 7-deoxy-9-deoxotaxol and 10-desacetoxy-7-deoxy-9-deoxotaxol. This procedure may be used to coat other types of devices including coronary stents, peripheral stents, and tracheal/bronchial stents, nasal stents, and fallopian tube stents.

Example 12

Paclitaxel/Siloxane Coating—End Coating

A tracheal stent is coated with a siloxane layer by exposing the device to gaseous tetramethylcyclotetrasiloxane that is then polymerized by low energy plasma polymerization onto the device surface. The thickness of the siloxane layer may be increased by increasing the polymerization time. The ends of the device are then immersed into a 9-deoxotaxol/THF solution. The 9-deoxotaxol is absorbed into the siloxane coating. The device is then removed from the solution and is dried for 2 hours at 40° C. in a forced air oven. The device is then further dried under vacuum at room temperature for 24 hours. The amount of 9-deoxotaxol coated onto the device ends may be varied by altering the concentration of the paclitaxel/THF solution as well as altering the immersion time of the device ends in the paclitaxel THF solution. In addition to 9-deoxotaxol, the following are exemplary compounds that may be used to coat the device: 7-deoxy-9-deoxotaxol and 10-desacetoxy-7-deoxy-9-deoxotaxol. This procedure may be used to coat other types of devices including coronary stents and peripheral stents.

Example 13

Heparin Coating

A tracheal stent is dipped into a solution containing different amounts of a tridodecyl methyl ammonium chloride-heparin complex solution (PolySciences). After various incubation times, the device is removed and dried in a forced air oven (50° C.). The device is then further dried in a vacuum oven overnight. Other types of devices that may be coated with this procedure include coronary stents, peripheral stents, nasal and sinus stents, and bronchial stents.

Example 14

Spray-Coated Devices

2% solutions poly(styrene-co-isobutylene-styrene) (SIBS) are prepared using THF as the solvent. Various amounts of 9-deoxotaxol are added to each solution. A biliary stent held with a pair of tweezers and is then spray coated with one of the paclitaxel/polymer solutions using an airbrush. The device is then air-dried. The device is then held in a new location using the tweezers and a second coat of paclitaxel/polymer is applied. The device is air-dried and is then dried under vacuum overnight. The total amount of 9-deoxotaxol coated onto the device may be altered by changing the paclitaxel content in the solution as well as by increasing the number of coatings applied. In addition to 9-deoxotaxol, the following are exemplary compounds that may be used to coat the device: 7-deoxy-9-deoxotaxol and 10-desacetoxy-7-deoxy-9-deoxotaxol.

Example 15

Drug Coated Covered Stent-Non-Degradable

A covered stent (WALLGRAFT, Boston Scientific Corporation) is attached to a rotating mandrel. A solution of paclitaxel (5% w/w) in a polyurethane (CHRONOFLEX 85A)/THF solution (2.5% w/v) is then sprayed onto the outer surface of the covered stent. The solution is sprayed on at a rate that ensures that the graft material is not damaged or saturated with the sprayed solution. The covered stent is allowed to air dry after which it is dried under vacuum for 24 hours. In addition to 9-deoxotaxol, the following are exemplary compounds that may be used to coat the device: 7-deoxy-9-deoxotaxol and 10-desacetoxy-7-deoxy-9-deoxotaxol.

Example 16

Drug Coated Covered Stent-Degradable

A WALLGRAFT stent is attached to a rotating mandrel. Paclitaxel (5% w/w) in a PLGA/ethyl acetate solution (2.5% w/v) is then sprayed onto the outer surface of the covered stent. The solution is sprayed on at a rate that ensures that the graft material is not damaged or saturated with the sprayed solution. The covered stent is allowed to air dry after which it is dried under vacuum for 24 hours. In addition to 9-deoxotaxol, the following are exemplary compounds that may be used to coat the device: 7-deoxy-9-deoxotaxol and 10-desacetoxy-7-deoxy-9-deoxotaxol.

Example 17

Drug Coated Covered Stent—Degradable Overcoat

A drug-coated WALLGRAFT stent from either Example 15 or Example 16 is attached to a rotating mandrel. A PLGA/ethyl acetate solution (2.5% w/v) is then sprayed onto the outer surface of the covered stent such that a coating is formed over the initial drug containing coating. The solution is sprayed on at a rate that ensures that the graft material is not damaged or saturated with the sprayed solution. The covered stent is allowed to air dry after which it is dried under vacuum for 24 hours.

Example 18

Drug-Loaded Microsphere Formulation 9-deoxotaxol (10% w/w) is added to a solution of PLGA (50/50, Mw≈54,000) in DCM (5% w/v). The solution is vortexed and then poured into a stirred (overhead stirrer with a 3 bladed TEFLON coated stirrer) aqueous PVA (approximately 89% hydrolyzed, Mw≈13,000, 2% w/v). The solution is stirred for 6 hours after which the solution is centrifuged to sediment the microspheres. The microspheres were resuspended in water. The centrifugation-washing process is repeated 4 times. The final microsphere solution is flash frozen in an acetone/dry-ice bath. The frozen solution is then freeze-dried to produce a fine powder. The size of the microspheres formed may be altered by changing the stirring speed and/or the PVA solution concentration. The freeze dried powder may be resuspended in PBS or saline and may be used for direct injection, as an incubation fluid or as an irrigation fluid. In addition to 9-deoxotaxol, the following are exemplary compounds that may be used to coat the device: 7-deoxy-9-deoxotaxol and 10-desacetoxy-7-deoxy-9-deoxotaxol.

Example 19

Drug Coated Stent (Exterior Coating)

A coronary stent is dipped into a polyurethane (CHRONOFLEX 85A)/THF solution (2.5% w/v). The coated stent is allowed to air dry for 10 seconds. The stent is then rolled in powdered 9-deoxotaxol that is spread thinly on a piece of release liner. The rolling process is done in such a manner that the paclitaxel powder predominantly adheres to the exterior side of the coated stent. The stents are air-dried for 1 hour followed by vacuum drying for 24 hours. In addition to 9-deoxotaxol, the following are exemplary compounds that may be used to coat the device: 7-deoxy-9-deoxotaxol and 10-desacetoxy-7-deoxy-9-deoxotaxol.

Example 20

Drug Coated Stent (Exterior Coating) With a Heparin Coating

The drug-coated stent from Example 19 is further coated with a heparin coating. The stents that are prepared in Example 19 are dipped into a solution of heparin-benzalkonium chloride complex (1.5% (w/v) in isopropanol, STS Biopolymers). The stents are removed from the solution and are air-dried for 1 hour followed by vacuum drying for 24 hours. This process results in both the interior and exterior surfaces of the covered stent being coated with heparin.

Example 21

Partial Drug Coating of a Covered Stent

A WALLGRAFT covered stent is attached to a rotating mandrel. A mask system is set up so that only the middle of the outer surface of the covered stent may be sprayed. A solution of 9-deoxotaxol (5% w/w) in a polyurethane (CHRONOFLEX 85A)/THF solution (2.5% w/v) is then sprayed onto the outer surface of the covered stent. The solution is sprayed on at a rate that ensures that the graft material is not damaged or saturated with the sprayed solution. The covered stent is allowed to air dry after which it is dried under vacuum for 24 hours. In addition to 9-deoxotaxol, the following are exemplary compounds that may be used to coat the device: 7-deoxy-9-deoxotaxol and 10-desacetoxy-7-deoxy-9-deoxotaxol.

Example 22

Paclitaxel Derivative Coated Covered Stent

A WALLGRAFT covered stent is attached to a rotating mandrel. A mask system is set up so that only the middle of the outer surface of the covered stent may be sprayed. A solution of 9-deoxotaxol (5% w/w) in a polyurethane (CHRONOFLEX 85A)/THF solution (2.5% w/v) is then sprayed onto the outer surface of the covered stent. The solution is sprayed on at a rate that ensures that the graft material is not damaged or saturated with the sprayed solution. The covered stent is allowed to air dry. The mask is then rearranged so that only the ends of the outer surface of the covered stent may be sprayed. The ends of the outer surface of the covered stent are then sprayed with a dexamethasone (10% w/w)/polyurethane (CHRONOFLEX 85A)/THF solution (2.5% w/v). The sample is air dried after which it is dried under vacuum for 24 hours. In addition to 9-deoxotaxol, the following are exemplary compounds that may be used to coat the device: 7-deoxy-9-deoxotaxol and 10-desacetoxy-7-deoxy-9-deoxotaxol.

Example 23

Drug-Heparin Coated Covered Stent

A WALLGRAFT covered stent is attached to a rotating mandrel. A mask system is set up so that only the middle of the outer surface of the covered stent may be sprayed. A solution of 9-deoxotaxol (5% w/w) in a polyurethane (CHRONOFLEX 85A)/THF solution (2.5% w/v) is then sprayed onto the outer surface of the covered stent. The solution is sprayed on at a rate that ensures that the graft material is not damaged or saturated with the sprayed solution. The covered stent is allowed to air dry. The mask is then rearranged so that only the ends of the outer surface of the covered stent may be sprayed. The ends of the outer surface of the covered stent are then sprayed with a heparin-benzalkonium chloride complex (1.5% (w/v) in isopropanol, STS Biopolymers). The sample is air dried after which it is dried under vacuum for 24 hours. In addition to 9-deoxotaxol, the following are exemplary compounds that may be used to coat the device: 7-deoxy-9-deoxotaxol and 10-desacetoxy-7-deoxy-9-deoxotaxol.

Example 24

Drug-Dexamethaxone Coated Covered Stent

A WALLGRAFT stent is attached to a rotating mandrel. A solution of 9-deoxotaxol (5% w/w) and dexamethazone (5% w/w) in a PLGA (50/50, Mw≈54,000)/ ethyl acetate solution (2.5% w/v) is sprayed onto the outer surface of the covered stent. The solution is sprayed on at a rate that ensures that the graft material is not damaged or saturated with the sprayed solution. The covered stent is allowed to air dry after which it is dried under vacuum for 24 hours. In addition to 9-deoxotaxol, the following are exemplary compounds that may be used to coat the device: 7-deoxy-9-deoxotaxol and 10-desacetoxy-7-deoxy-9-deoxotaxol.

Example 25

Drug-Dexamethasone Coated Covered Stent (Sequential Coating)

A WALLGRAFT stent is attached to a rotating mandrel. A solution of 9-deoxotaxol (5% w/w) in a PLGA (50/50, Mw≈54,000)/ethyl acetate solution (2.5% w/v) is sprayed onto the outer surface of the covered stent. The solution is sprayed on at a rate that ensures that the graft material is not damaged or saturated with the sprayed solution. The covered stent is allowed to air dry. A methanol solution of dexamethasone is then sprayed onto the outer surface of the covered stent (at a rate that ensures that the graft material is not damaged or saturated with the sprayed solution). The covered stent is allowed to air dry after which it is dried under vacuum for 24 hours. In addition to 9-deoxotaxol, the following are exemplary compounds that may be used to coat the device: 7-deoxy-9-deoxotaxol and 10-desacetoxy-7-deoxy-9-deoxotaxol.

Example 26

Screening Assay for Assessing the Effect of Paclitaxel Compounds on Nitric Oxide Production by Macrophages The murine macrophage cell line RAW 264.7 was trypsinized to remove cells from flasks and plated in individual wells of a 6-well plate. Approximately $2\times10^6$ cells were plated in 2 mL of media containing 5% heat-inactivated fetal bovine serum (FBS). RAW 264.7 cells were incubated at 37° C. for 1.5 hours to allow adherence to plastic. Paclitaxel was prepared in DMSO at a concentration of $10^{-2}$ M and serially diluted 10-fold to give a range of stock concentrations ($10^{-8}$ M to $10^{-2}$ M). Media was then removed and cells were incubated in 1 ng/mL of recombinant murine IFNγ and 5 ng/mL of LPS with or without paclitaxel in fresh media containing 5% FBS. Paclitaxel was added to cells by directly adding paclitaxel DMSO stock solutions, prepared earlier, at a 1/1000 dilution, to each well. Plates containing IFNγ, LPS plus or minus paclitaxel were incubated at 37° C. for 24 hours (Chem. Ber. (1879) 12: 426; J. AOAC (1977) 60-594; Ann. Rev. Biochem. (1994) 63: 175).

At the end of the 24 hour period, supernatants were collected from the cells and assayed for the production of nitrites. Each sample was tested in triplicate by aliquoting 50 μL of supernatant in a 96-well plate and adding 50 μL of Greiss Reagent A (0.5 g sulfanilamide, 1.5 ml $H_3PO_4$, 48.5 ml $ddH_2O$) and 50 μL of Greiss Reagent B (0.05 g N-(1-naphthyl)-ethylenediamine, 1.5 mL $H_3PO_4$, 48.5 mL $ddH_2O$). Optical density was read immediately on microplate spectrophotometer at 562 nm absorbance. Absorbance over triplicate wells was averaged after subtracting background and concentration values were obtained from the nitrite standard curve (1 μM to 2 mM). Inhibitory concentration of 50% ($IC_{50}$) was determined by comparing average nitrite concentration to the positive control (cell stimulated with IFNγ and LPS). An average of n=4 replicate experiments was used to determine $IC_{50}$ values for paclitaxel: $IC_{50}$ (nM): 7 nM.

Example 27

Surgical Adhesions Model to Assess Fibrosis Inhibiting Agents

The rabbit uterine horn model is used to assess the anti-fibrotic capacity of formulations in vivo. Mature New Zealand White (NZW) female rabbits are placed under general anesthetic. Using aseptic precautions, the abdomen is opened in two layers at the midline to expose the uterus. Both uterine horns are lifted out of the abdominal cavity and assessed for size on the French Scale of catheters. Horns between #8 and #14 on the French Scale (2.5-4.5 mm diameter) are deemed suitable for this model. Both uterine horns and the opposing peritoneal wall are abraded with a #10 scalpel blade at a 45° angle over an area 2.5 cm in length and 0.4 cm in width until punctuate bleeding is observed. Abraded surfaces are tamponaded until bleeding stops. The individual horns are then opposed to the peritoneal wall and secured by two sutures placed 2 mm beyond the edges of the abraded area. The formulation is applied and the abdomen is closed in three layers. After 14 days, animals are evaluated post mortem with the extent and severity of adhesions being scored both quantitatively and qualitatively.

Example 28

Screening Assay for Assessing the Effect of Paclitaxel Compounds on Cell Proliferation Fibroblasts at 70-90% confluency were trypsinized, replated at 600 cells/well in media in 96-well plates and allowed to attach overnight. Paclitaxel was prepared in DMSO at a concentration of $10^{-2}$ M and diluted 10-fold to give a range of stock concentrations ($10^{-8}$ M to $10^{-2}$ M). Drug dilutions were diluted 1/1000 in media and added to cells to give a total volume of 200 μL/well. Each drug concentration was tested in triplicate wells. Plates containing fibroblasts and paclitaxel were incubated at 37° C. for 72 hours (In vitro toxicol. (1990) 3: 219; Biotech. Histochem. (1993) 68: 29; Anal. Biochem. (1993) 213: 426).

Figure 8:
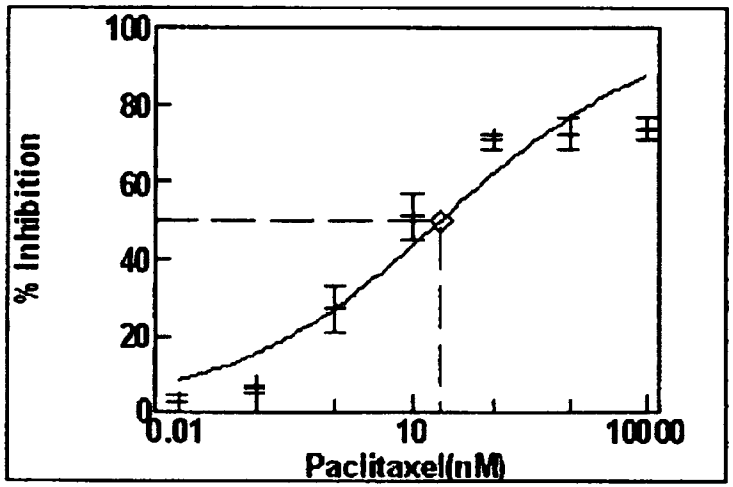
FIG. 8 is graph showing the results of a screening assay for assessing the effect of paclitaxel on cell proliferation of human fibroblasts.

To terminate the assay, the media was removed by gentle aspiration. A 1/400 dilution of CYQUANT 400X GR dye indicator (Molecular Probes; Eugene, Oreg.) was added to 1X Cell Lysis buffer, and 200 μL of the mixture was added to the wells of the plate. Plates were incubated at room temperature, protected from light for 3-5 minutes. Fluorescence was read in a fluorescence microplate reader at ~480 nm excitation wavelength and ~520 nm emission maxima. Inhibitory concentration of 50% ($IC_{50}$) was determined by taking the average of triplicate wells and comparing average relative fluorescence units to the DMSO control. An average of n=4 replicate experiments was used to determine $IC_{50}$ values. $IC_{50}$ (nM): paclitaxel, 23 (FIG. 8)

Example 29

Evaluation of Paclitxel Containing Mesh on Intimal Hyperplasia Development in a Rat Balloon Injury Carotid Artery Model A rat balloon injury carotid artery model was used to demonstrate the efficacy of a paclitaxel containing mesh system on the development of intimal hyperplasia fourteen days following placement.

Control Group

Wistar rats weighing 400-500 g were anesthetized with 1.5% halothane in oxygen and the left external carotid artery was exposed. A 2 French Fogarty balloon embolectomy catheter (Baxter, Irvine, Calif.) was advanced through an arteriotomy in the external carotid artery down the left common carotid artery to the aorta. The balloon was inflated with enough saline to generate slight resistance (approximately 0.02 ml) and it was withdrawn with a twisting motion to the carotid bifurcation. The balloon was then deflated and the procedure repeated twice more. This technique produced distension of the arterial wall and denudation of the endothelium. The external carotid artery was ligated after removal of the catheter. The right common carotid artery was not injured and was used as a control.

Local Perivascular Paclitaxel Treatment

Immediately after injury of the left common carotid artery, a 1 cm long distal segment of the artery was exposed and treated with a 1×1 cm paclitaxel-containing mesh. The wound was then closed the animals were kept for 14 days.

Histology and Immunohistochemistry

At the time of sacrifice, the animals were euthanized with carbon dioxide and pressure perfused at 100 mmHg with 10% phosphate buffered formaldehyde for 15 minutes. Both carotid arteries were harvested and left overnight in fixative. The fixed arteries were processed and embedded in paraffin wax. Serial cross-sections were cut at 3 μm thickness every 2 mm within and outside the implant region of the injured left carotid artery and at corresponding levels in the control right carotid artery. Cross-sections were stained with Mayer's hematoxylin-and-eosin for cell count and with Movat's pentachrome stains for morphometry analysis and for extracellular matrix composition assessment.

Results

Figure 2:
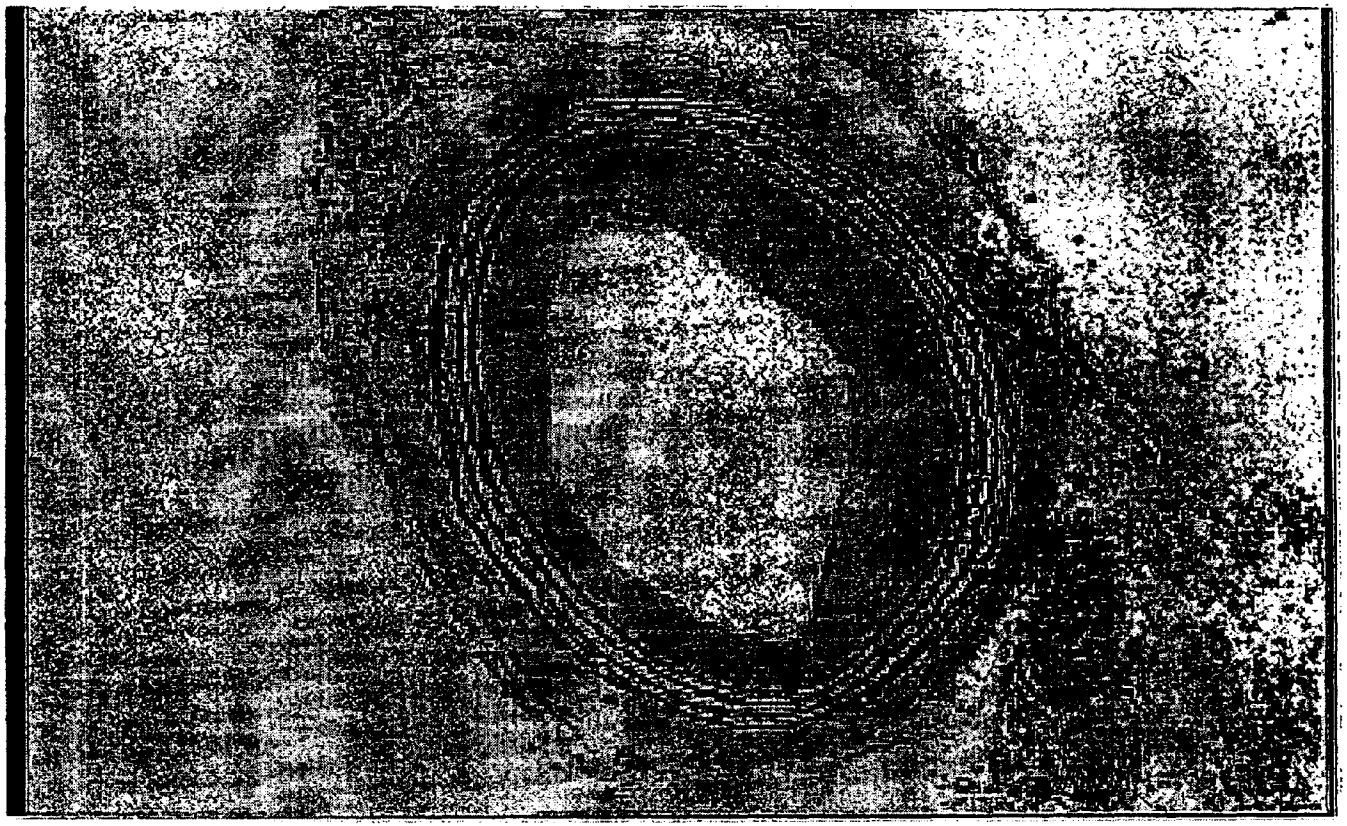
FIG. 2 is a picture that shows an injured carotid artery from a rat balloon injury model.
Figure 3:
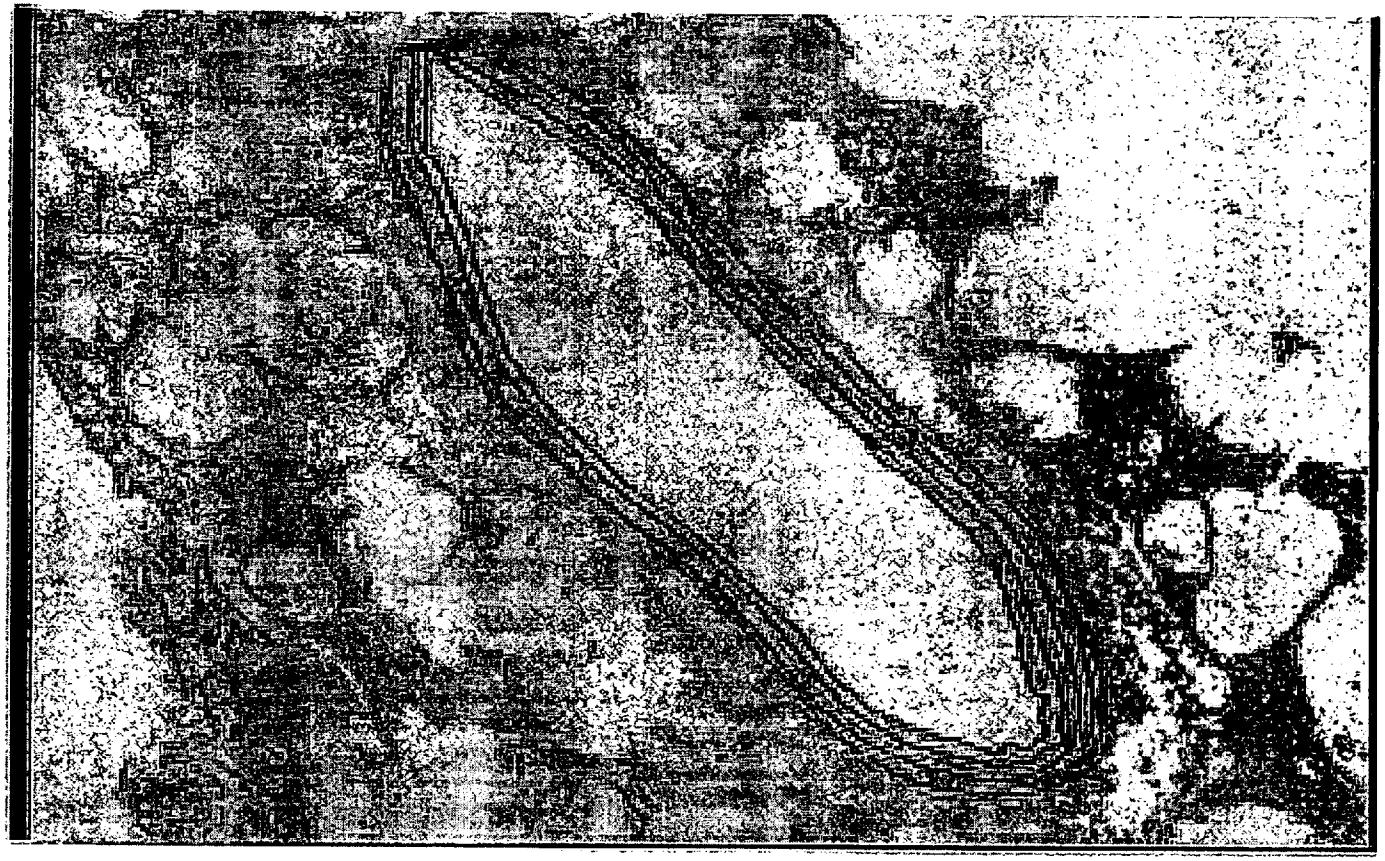
FIG. 3 is a picture that shows a paclitaxel/mesh treated carotid artery in a rat balloon injury model (345 μg paclitaxel in a 50:50 PLG coating on a 10:90 PLG mesh).

From FIGS. 1-3, it is evident that the perivascular delivery of paclitaxel using the paclitaxel mesh formulation resulted is a dramatic reduction in intimal hyperplasia.

Example 30

Effect of Paclitaxel and Other Anti-Microtubule Agents on Matrix Metalloproteinase Production A. Materials and Methods 1. IL-1 stimulated AP-1 transcriptional activity is inhibited by paclitaxel Chondrocytes were transfected with constructs containing an AP-1 driven CAT reporter gene, and stimulated with IL-1, IL-1 (50 ng/ml) was added and incubated for 24 hours in the absence and presence of paclitaxel at various concentrations. Paclitaxel treatment decreased CAT activity in a concentration dependent manner (mean±SD). The data noted with an asterisk (*) have significance compared with IL-1-induced CAT activity according to a t-test, $P<0.05$. The results shown are representative of three independent experiments.

2. Effect of paclitaxel on IL-1 induced AP-1 DNA binding activity, AP-1 DNA

Binding activity was assayed with a radiolabeled human AP-1 sequence probe and gel mobility shift assay. Extracts from chondrocytes untreated or treated with various amounts of paclitaxel ($10^{-7}$ to $10^{-5}$ M) followed by IL-1β (20 ng/ml) were incubated with excess probe on ice for 30 minutes, followed by non-denaturing gel electrophoresis. The "com" lane contains excess unlabeled AP-1 oligonucleotide. The results shown are representative of three independent experiments.

3. Effect of paclitaxel on IL-1 induced MMP-1 and MMP-3 mRNA expression

Cells were treated with paclitaxel at various concentrations ($10^{-7}$ to $10^{-5}$ M) for 24 hours, then treated with IL-1β (20 ng/ml) for additional 18 hours in the presence of paclitaxel. Total RNA was isolated, and the MMP-1 mRNA levels were determined by Northern blot analysis. The blots were subsequently stripped and reprobed with $^{32}$P-radiolabeled rat GAPDH eDNA, which was used as a housekeeping gene. The results shown are representative of four independent experiments. Quantitation of collagenase-1 and stromelysin-expression mRNA levels. The MMP-1 and MMP-3 expression levels were normalized with GAPDH.

4. Effect of other anti-microtubules on collagenase expression

Primary chondrocyte cultures were freshly isolated from calf cartilage. The cells were plated at $2.5\times10^6$ per ml in 100×20 mm culture dishes and incubated in Ham's F12 medium containing 5% FBS overnight at 37° C. The cells were starved in serum-free medium overnight and then treated with anti-microtubule agents at various concentrations for 6 hours. IL-1 (20 ng/ml) was then added to each plate and the plates incubated for an additional 18 hours. Total RNA was isolated by the acidified guanidine isothiocyanate method and subjected to electrophoresis on a denatured gel. Denatured RNA samples (15 μg) were analyzed by gel electrophoresis in a 1% denatured gel, transferred to a nylon membrane and hybridized with the $^{32}$P-labeled collagenase cDNA probe. $^{32}$P-labeled glyceraldehyde phosphate dehydrase (GAPDH) cDNA as an internal standard to ensure roughly equal loading. The exposed films were scanned and quantitatively analyzed with IMAGEQUANT.

B. Results

1. Promoters on the family of matrix metalloproteinases

Figure 4A:
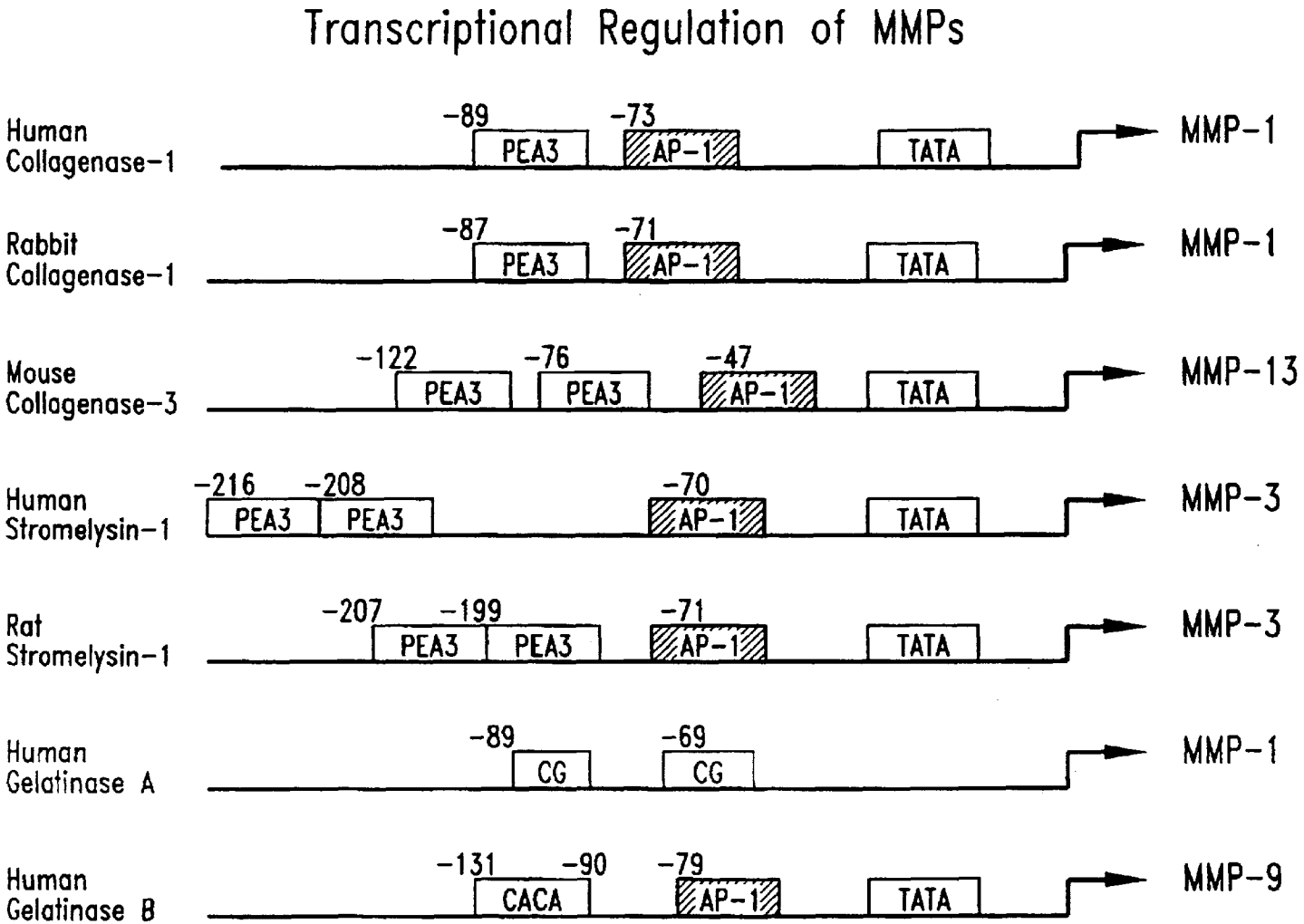
FIG. 4A schematically depicts the transcriptional regulation of matrix metalloproteinases.

FIG. 4A shows that all matrix metalloproteinases contained the transcriptional elements AP-1 and PEA-3 with the exception of Gelatinase B. It has been well established that expression of matrix metalloproteinases such as collagenases and stromelysins are dependent on the activation of the transcription factors AP-1. Thus inhibitors of AP-1 may inhibit the expression of matrix metalloproteinases.

2. Effect of paclitaxel on AP-1 transcriptional activity

Figure 4B:
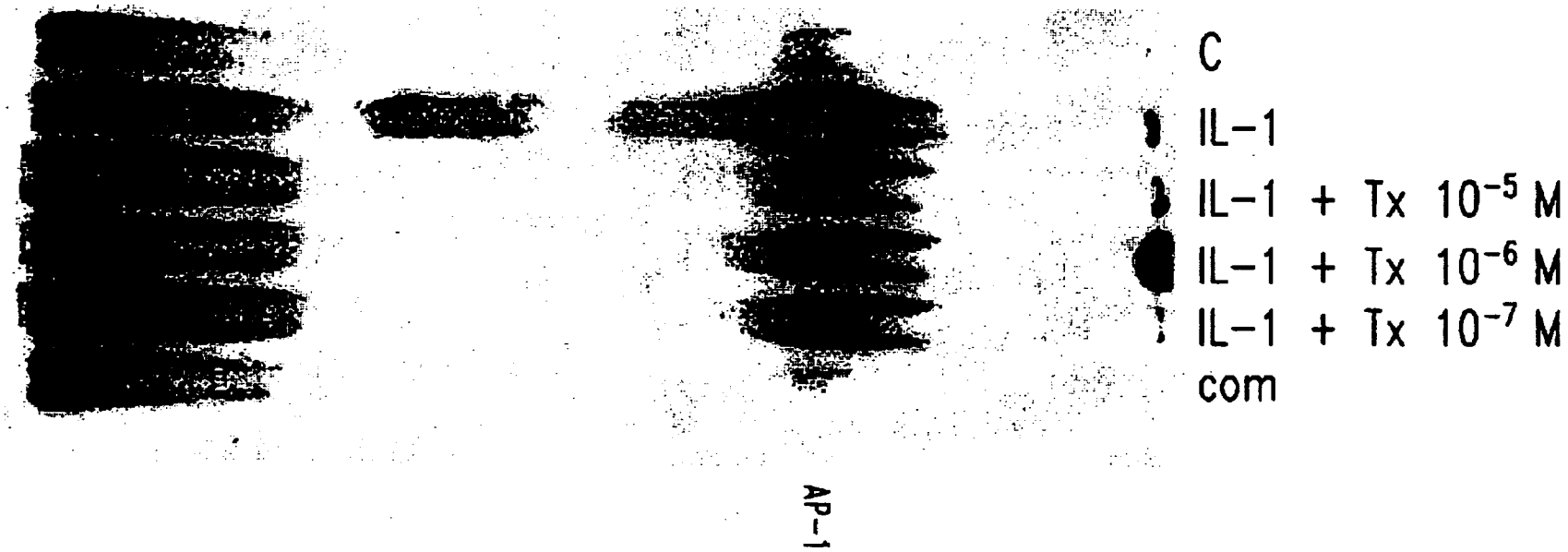
FIG. 4B is a blot which demonstrates that IL-1 stimulates AP-1 transcriptional activity.

As demonstrated in FIG. 4B, IL-1 stimulated AP-1 transcriptional activity 5-fold. Pretreatment of transiently transfected chondrocytes with paclitaxel reduced IL-1 induced AP-1 reporter gene CAT activity. Thus, IL-1 induced AP-1 activity was reduced in chondrocytes by paclitaxel in a concentration dependent manner ($10^{-7}$ to $10^{-5}$ M). These data demonstrated that paclitaxel was a potent inhibitor of AP-1 activity in chondrocytes.

3. Effect of paclitaxel on AP-1 DNA binding activity

Figure 4C:
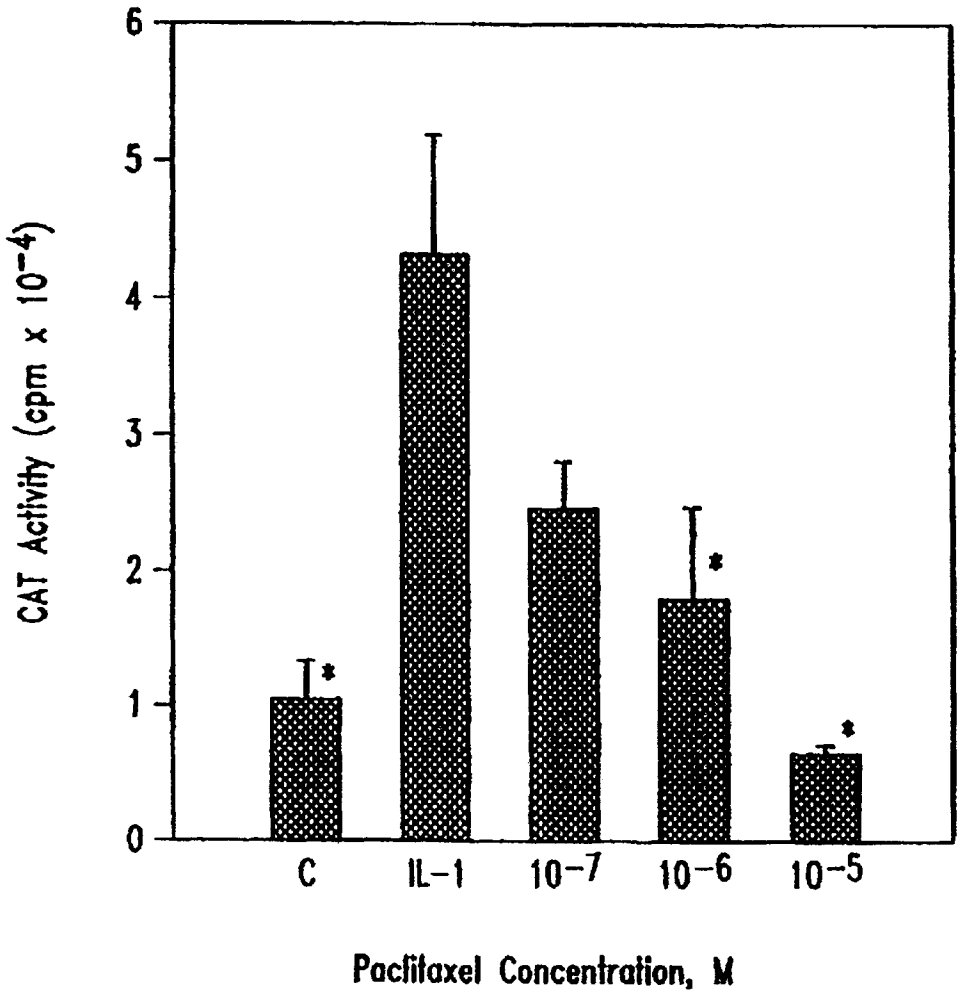
FIG. 4C is a graph that shows that IL-1 induced binding activity decreased in lysates from chondrocytes which were pretreated with paclitaxel.

To confirm that paclitaxel inhibition of AP-1 activity was not due to nonspecific effects, the effect of paclitaxel on IL-1 induced AP-1 binding to oligonucleotides using chondrocyte nuclear lysates was examined. As shown in FIG. 4C, IL-1 induced binding activity decreased in lysates from chondrocyte which had been pretreated with paclitaxel at concentration $10^{-7}$ to $10^{-5}$ M for 24 hours. Paclitaxel inhibition of AP-1 transcriptional activity closely correlated with the decrease in AP-1 binding to DNA.

4. Effect of paclitaxel on collagenase and stromelysin expression

Figure 4D:
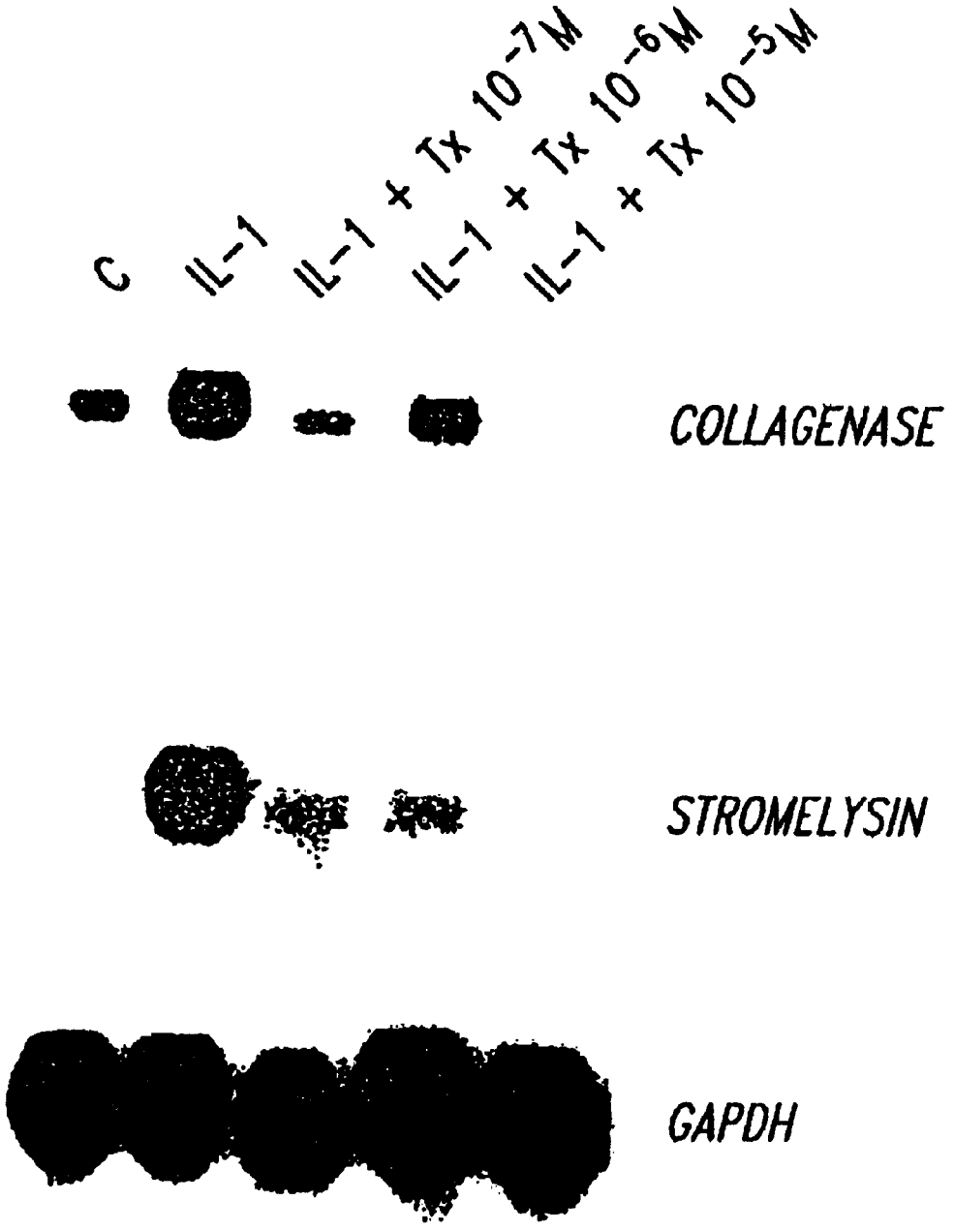
FIG. 4D is a blot which shows that IL-1 induction increases collagenase and stromelysin in RNA levels in chondrocytes, and that this induction can be inhibited by pretreatment with paclitaxel.
Figure 5A:
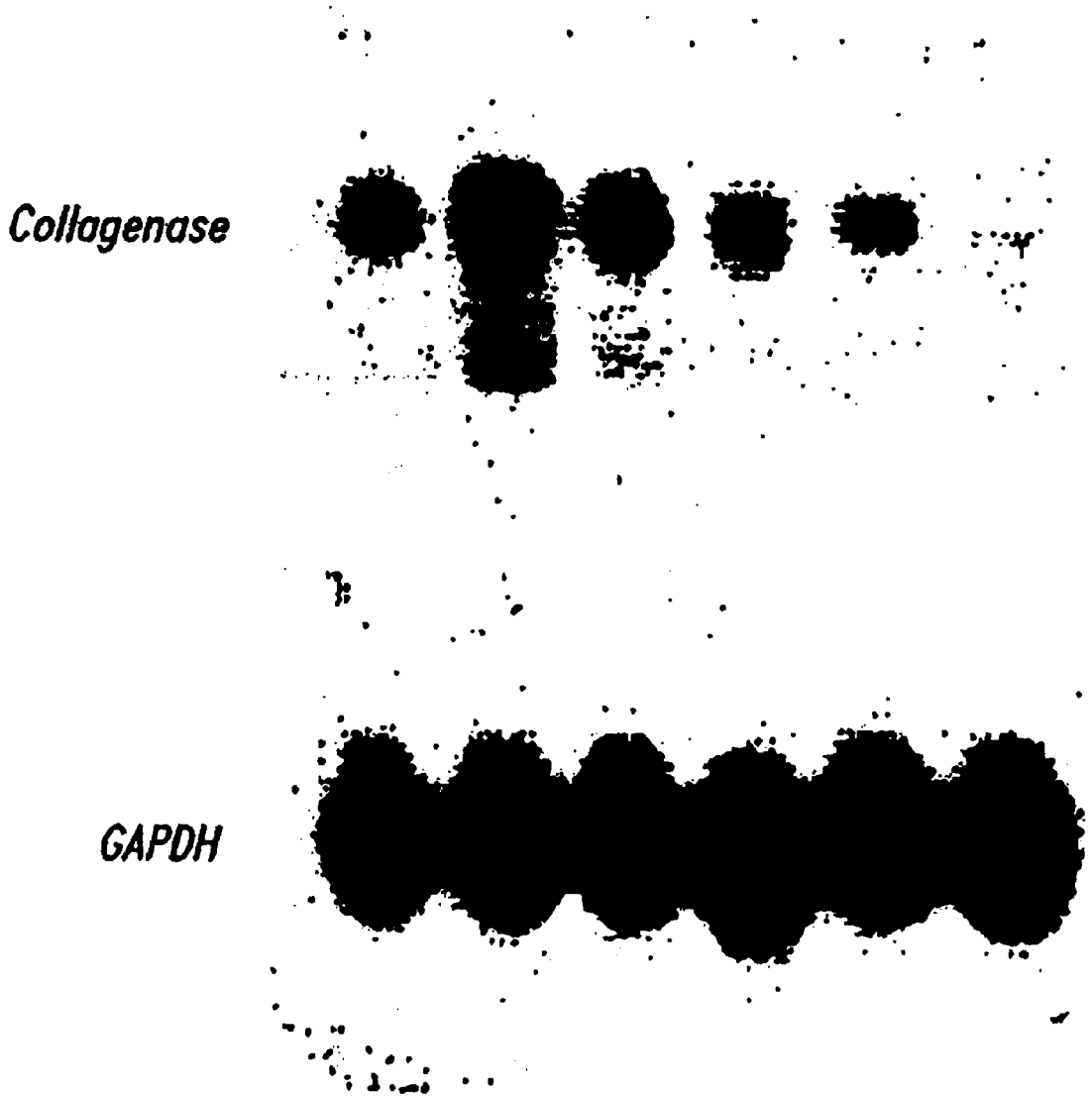
FIGS. 5A-H are blots that show the effect of various antimicrotubule agents in inhibiting collagenase expression.
Figure 5B:
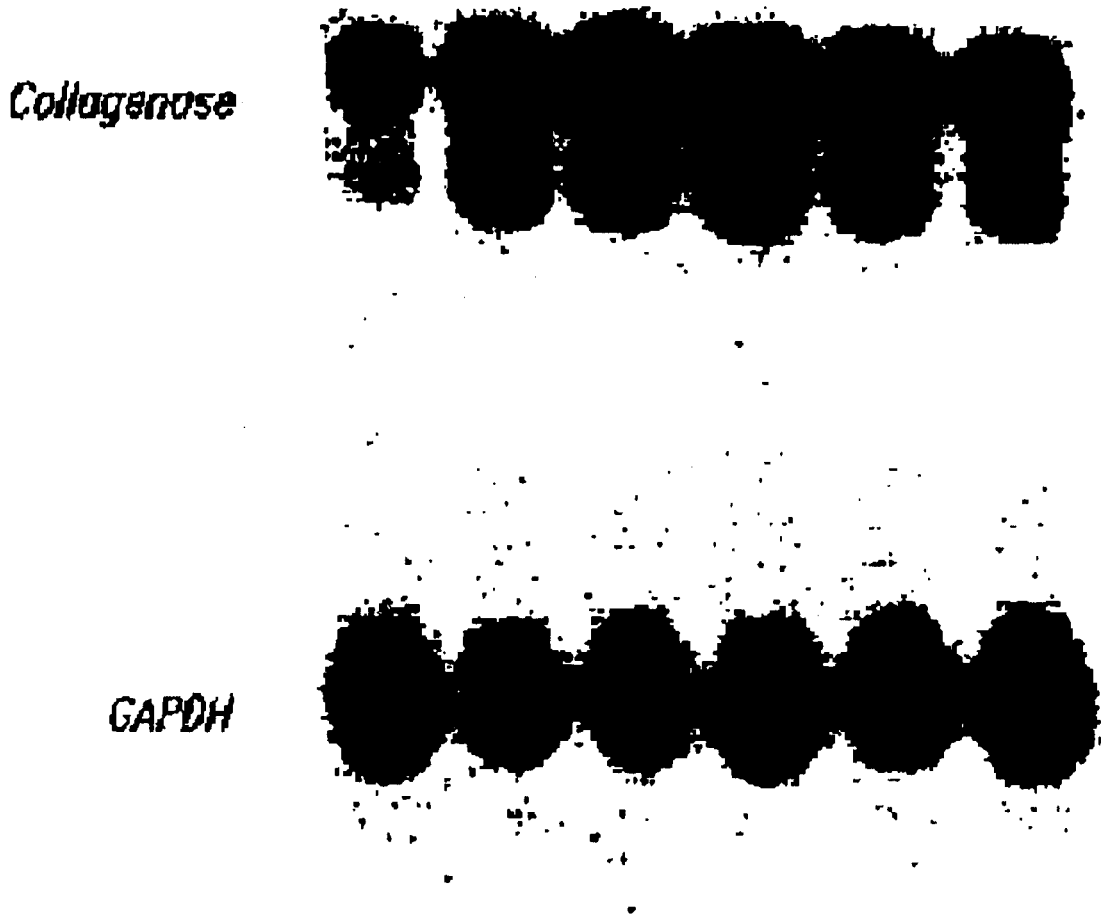
Figure 5C:
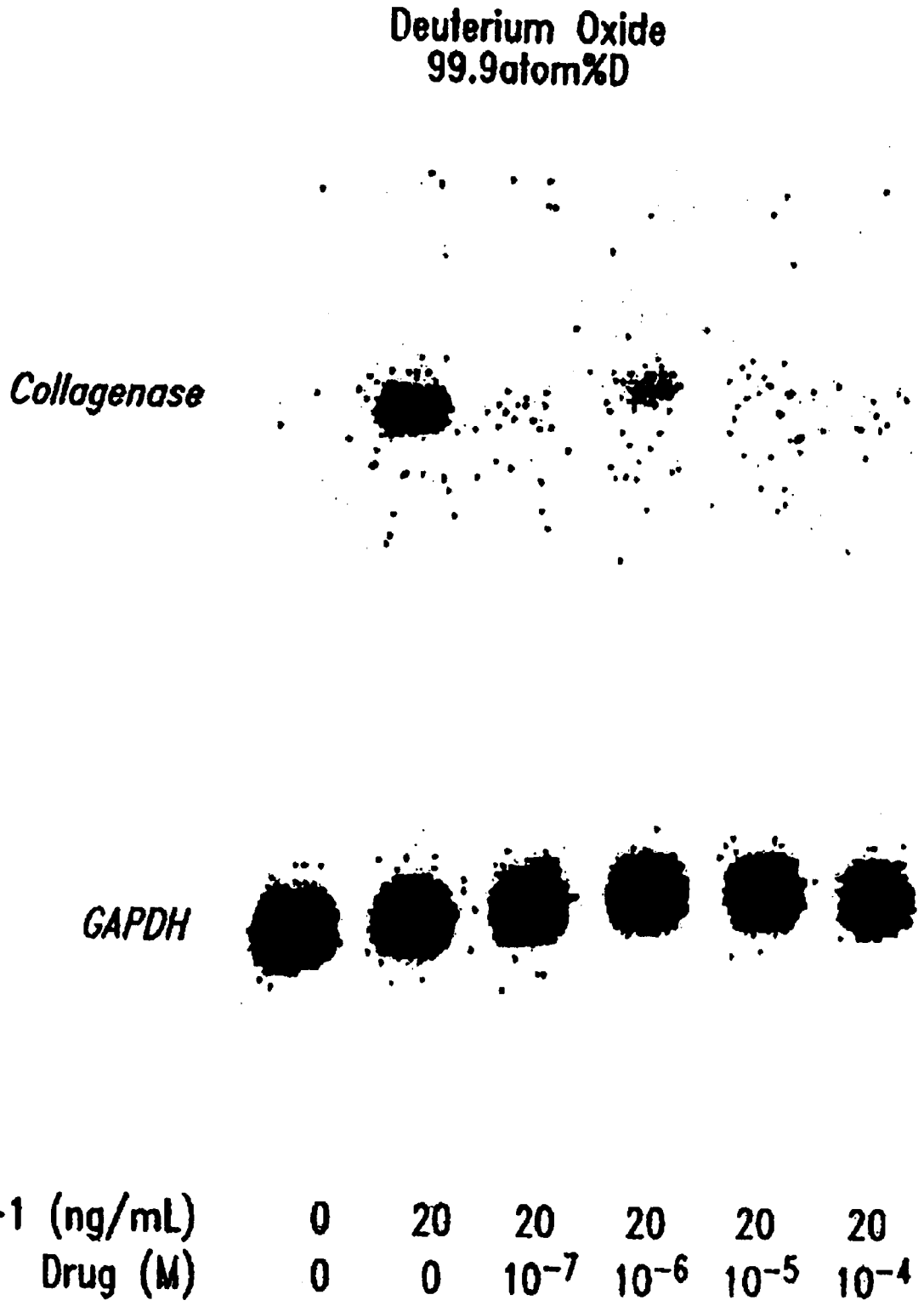
Figure 5D:
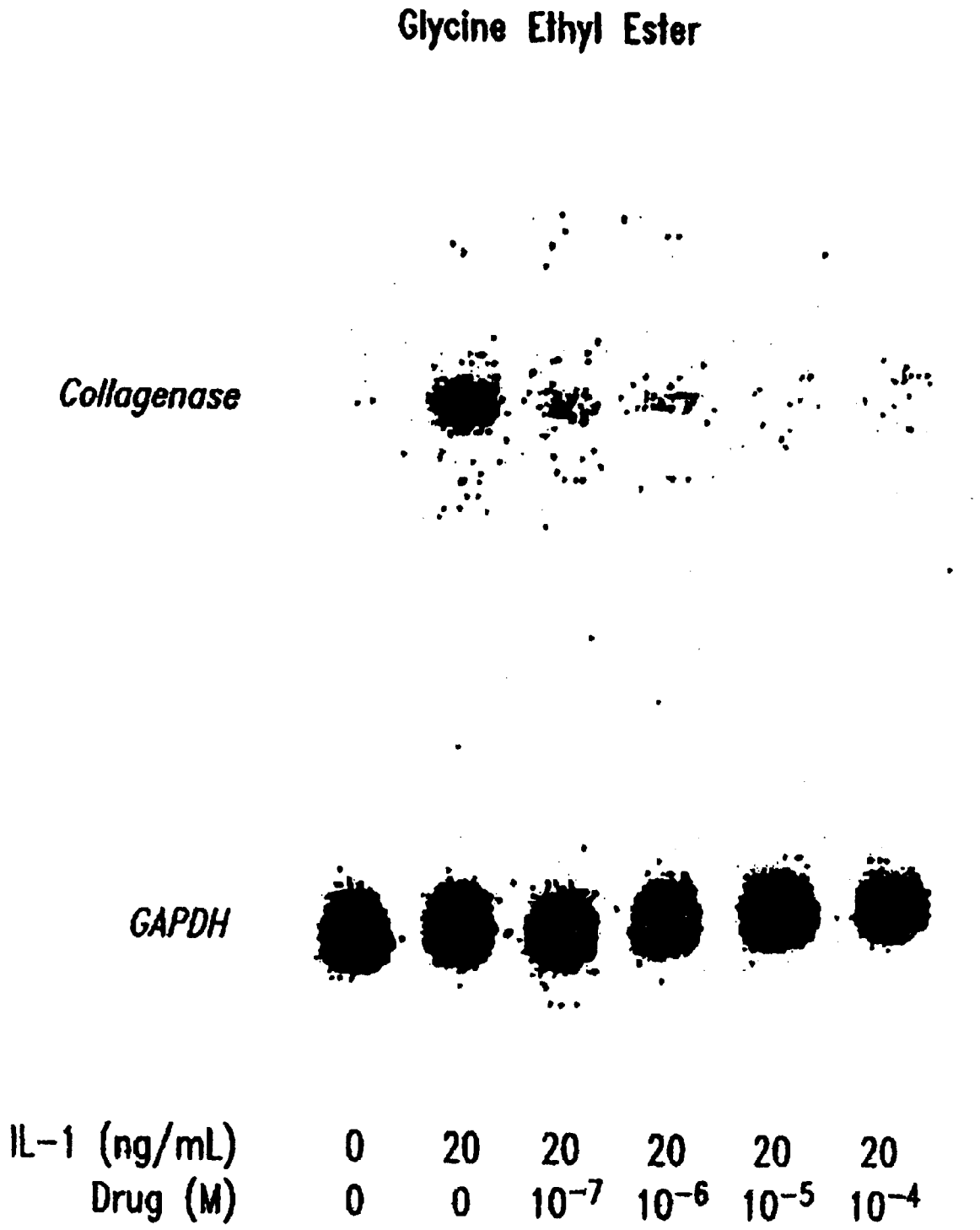
Figure 5E:
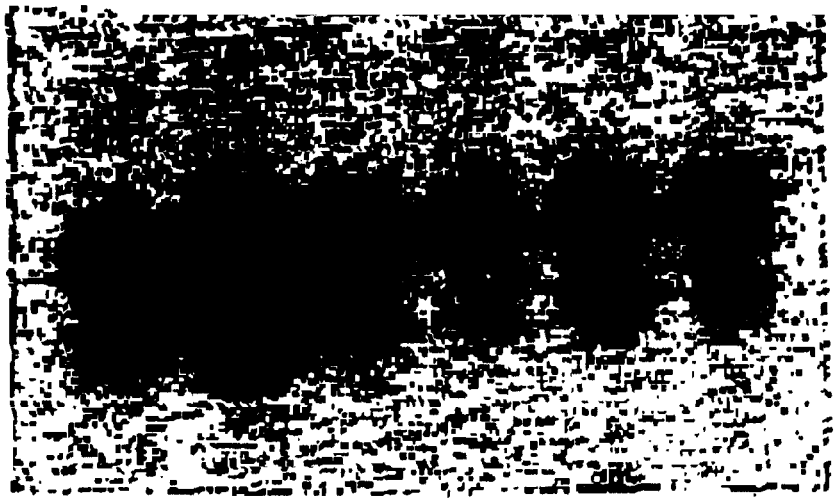
Figure 5E:
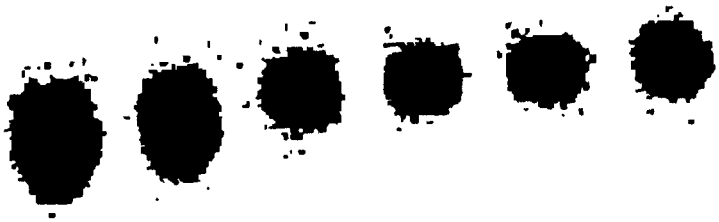
Figure 5F:
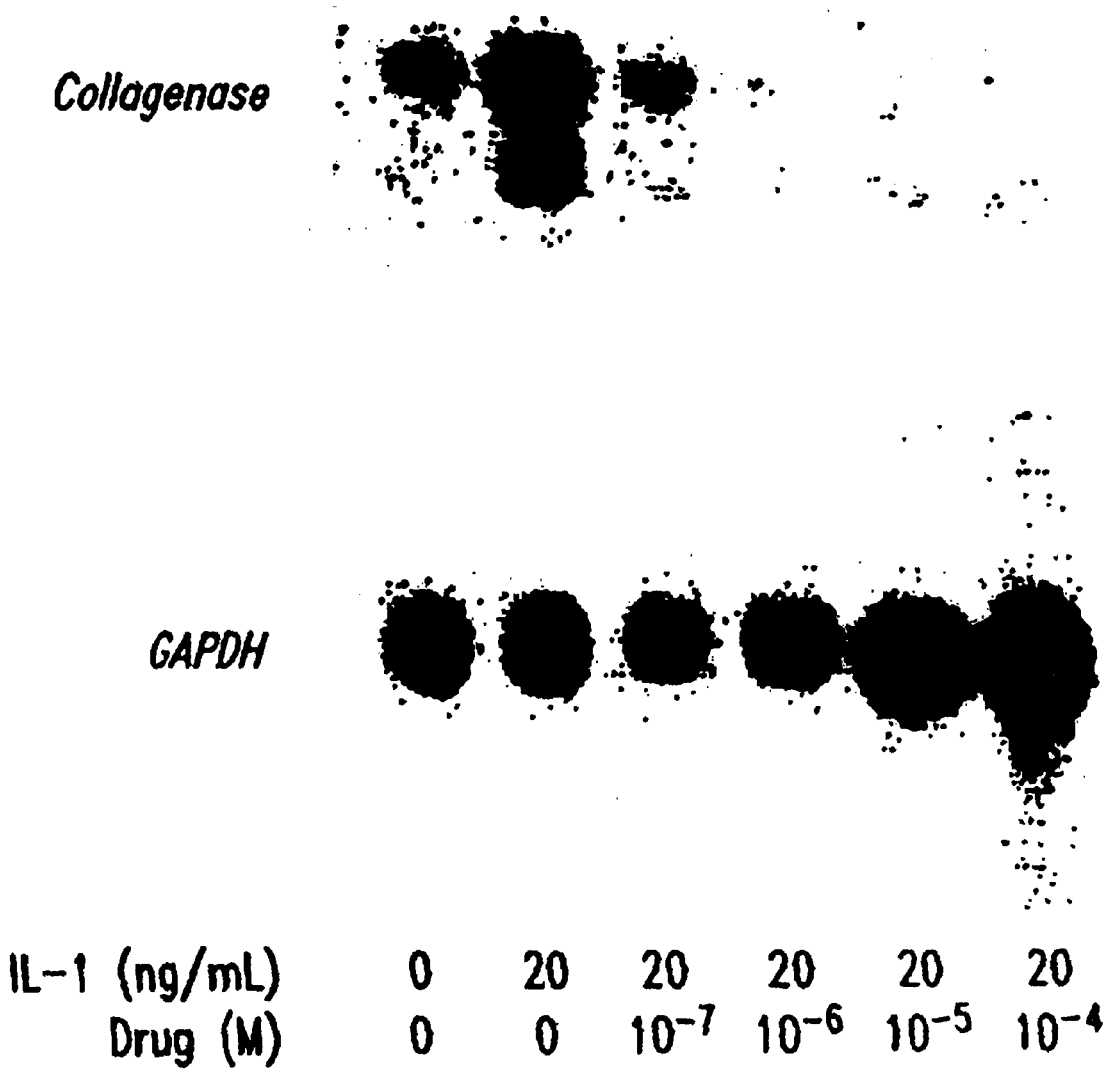
Figure 5G:
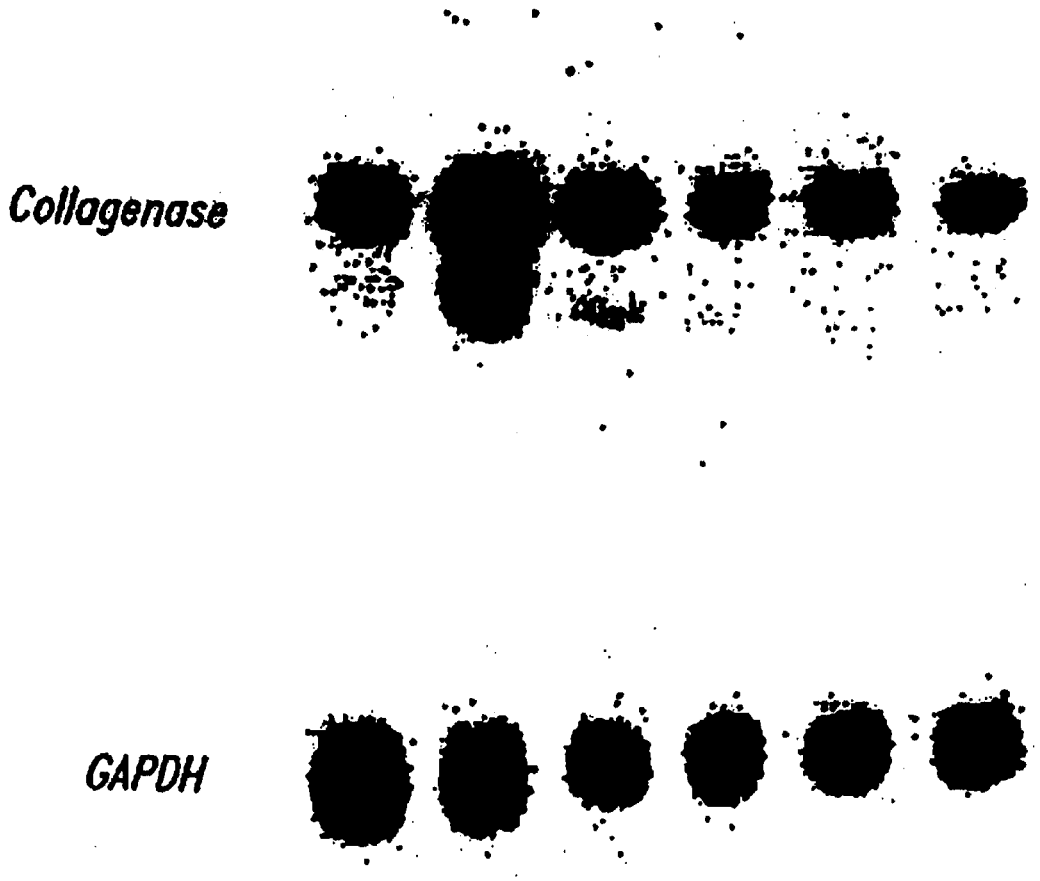
Figure 5H:
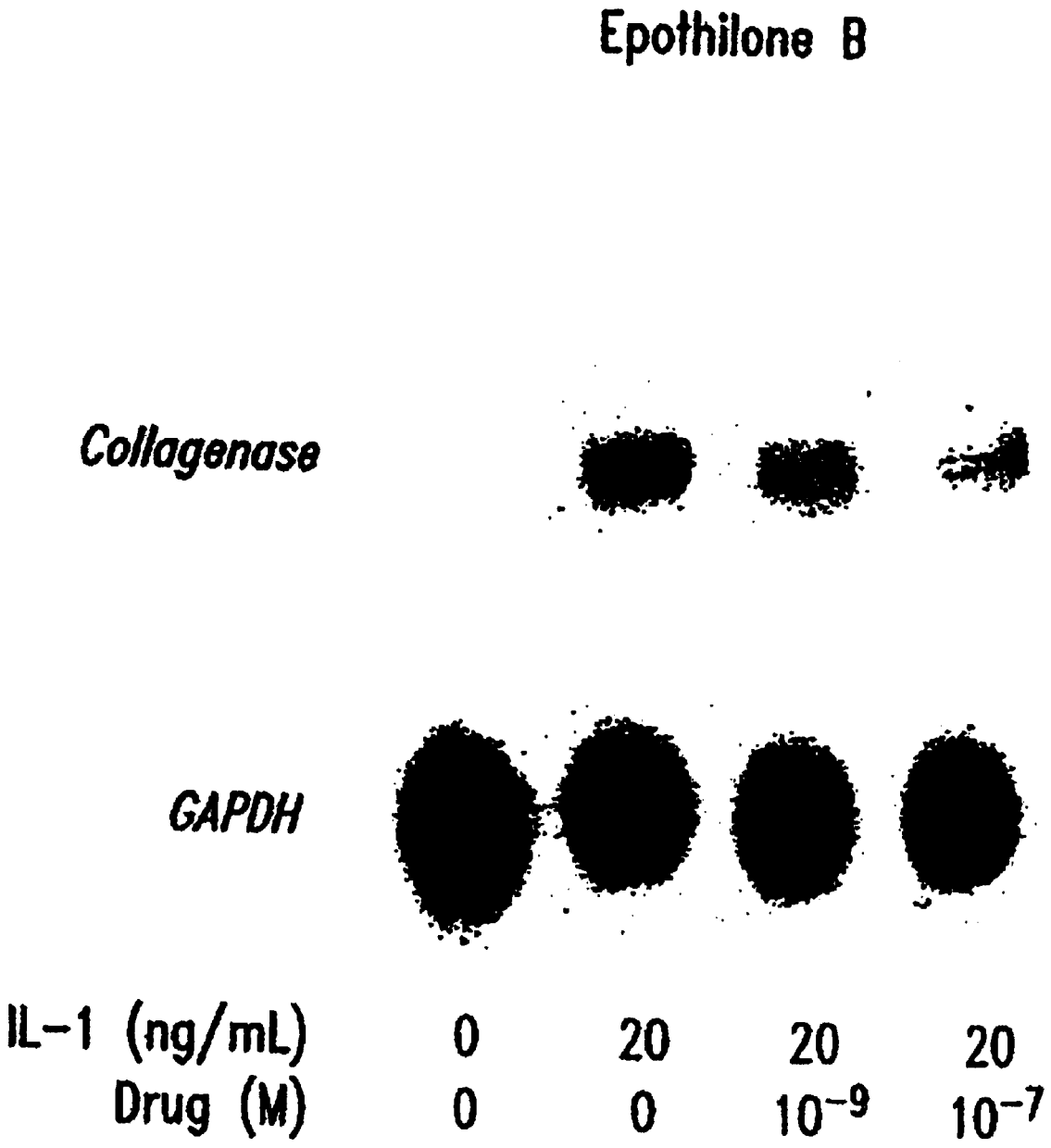

Since paclitaxel was a potent inhibitor of AP-1 activity, the effect of paclitaxel or IL-1 induced collagenase and stromelysin expression, two important matrix metalloproteinases involved in inflammatory diseases was examined. Briefly, as shown in FIG. 4D, IL-1 induction increases collagenase and stromelysin mRNA levels in chondrocytes. Pretreatment of chondrocytes with paclitaxel for 24 hours significantly reduced the levels of collagenase and stromelysin mRNA. At $10^{-5}$ M paclitaxel, there was complete inhibition. The results show that paclitaxel completely inhibited the expression of two matrix metalloproteinases at concentrations similar to which it inhibits AP-1 activity.

5. Effect of other anti-microtubules on collagenase expression

FIGS. 5A-H demonstrate that anti-microtubule agents inhibited collagenase expression. Expression of collagenase was stimulated by the addition of IL-1 which is a proinflammatory cytokine. Pre-incubation of chondrocytes with various anti-microtubule agents, specifically LY290181, hexylene glycol, deuterium oxide, glycine ethyl ester, ethylene glycol bis-(succinimidylsuccinate), tubercidin, $AlF_3$, and epothilone, all prevented IL-1-induced collagenase expression at concentrations as low as $1\times10^{-7}$ M.

C. Discussion

Paclitaxel was capable of inhibiting collagenase and stromelysin expression in vitro at concentrations of $10^{-6}$ M. Since this inhibition may be explained by the inhibition of AP-1 activity, a required step in the induction of all matrix metalloproteinases with the exception of gelatinase B, it is expected that paclitaxel may inhibit other matrix metalloproteinases which are AP-1 dependent. The levels of these matrix metalloproteinases are elevated in all inflammatory diseases and play a principle role in matrix degradation, cellular migration and proliferation, and angiogenesis. Thus, paclitaxel inhibition of expression of matrix metalloproteinases such as collagenase and stromelysin will have a beneficial effect in inflammatory diseases.

In addition to paclitaxel's inhibitory effect on collagenase expression, LY290181, hexylene glycol, deuterium oxide, glycine ethyl ester, $AlF_3$, tubercidin epothilone, and ethylene glycol bis-(succinimidylsuccinate), all prevented IL-1-induced collagenase expression at concentrations as low as $1\times10^{-7}$ M. Thus, anti-microtubule agents are capable of inhibiting the AP-1 pathway at varying concentrations.

Example 31

Inhibition of Angiogenesis by Paclitaxel

A. Chick Chorioallantoic Membrane ("CAM") Assays

Fertilized, domestic chick embryos were incubated for 3 days prior to shell-less culturing. In this procedure, the egg contents were emptied by removing the shell located around the air space. The interior shell membrane was then severed and the opposite end of the shell was perforated to allow the contents of the egg to gently slide out from the blunted end. The egg contents were emptied into round-bottom sterilized glass bowls and covered with petri dish covers. These were then placed into an incubator at 90% relative humidity and 3% $CO_2$ and incubated for 3 days.

Paclitaxel (Sigma, St. Louis, Mich.) was mixed at concentrations of 0.25, 0.5, 1, 5, 10, 30 μg per 10 ul aliquot of 0.5% aqueous methylcellulose. Since paclitaxel is insoluble in water, glass beads were used to produce fine particles. Ten microliter aliquots of this solution were dried on parafilm for 1 hour forming disks 2 mm in diameter. The dried disks containing paclitaxel were then carefully placed at the growing edge of each CAM at day 6 of incubation. Controls were obtained by placing paclitaxel-free methylcellulose disks on the CAMs over the same time course. After a 2 day exposure (day 8 of incubation) the vasculature was examined with the aid of a stereomicroscope. Liposyn II, a white opaque solution, was injected into the CAM to increase the visibility of the vascular details. The vasculature of unstained, living embryos were imaged using a Zeiss stereomicroscope which was interfaced with a video camera (Dage-MTI Inc., Michigan City, Ind.). These video signals were then displayed at 160× magnification and captured using an image analysis system (Vidas, Kontron; Etching, Germany). Image negatives were then made on a graphics recorder (Model 3000; Matrix Instruments, Orangeburg, N.Y.).

The membranes of the 8 day-old shell-less embryo were flooded with 2% glutaraldehyde in 0.1 M sodium cacodylate buffer; additional fixative was injected under the CAM. After 10 minutes in situ, the CAM was removed and placed into fresh fixative for 2 hours at room temperature. The tissue was then washed overnight in cacodylate buffer containing 6% sucrose. The areas of interest were postfixed in 1% osmium tetroxide for 1.5 hours at 4° C. The tissues were then dehydrated in a graded series of ethanols, solvent exchanged with propylene oxide, and embedded in Spurr resin. Thin sections were cut with a diamond knife, placed on copper grids, stained, and examined in a Joel 1200EX electron microscope. Similarly, 0.5 mm sections were cut and stained with toluene blue for light microscopy.

At day 11 of development, chick embryos were used for the corrosion casting technique. Mercox resin (Ted Pella, Inc., Redding, Calif.) was injected into the CAM vasculature using a 30-gauge hypodermic needle. The casting material consisted of 2.5 grams of Mercox CL-2B polymer and 0.05 grams of catalyst (55% benzoyl peroxide) having a 5 minute polymerization time. After injection, the plastic was allowed to sit in situ for an hour at room temperature and then overnight in an oven at 65° C. The CAM was then placed in 50% aqueous solution of sodium hydroxide to digest all organic components. The plastic casts were washed extensively in distilled water, air-dried, coated with gold/palladium, and viewed with the s 501B scanning electron microscope.

Results of the assay were as follows. At day 6 of incubation, the embryo was centrally positioned to a radially expanding network of blood vessels; the CAM developed adjacent to the embryo. These growing vessels lie close to the surface and are readily visible making this system an idealized model for the study of angiogenesis. Living, unstained capillary networks of the CAM may be imaged noninvasively with a stereomicroscope.

Transverse sections through the CAM show an outer ectoderm consisting of a double cell layer, a broader mesodermal layer containing capillaries which lie subjacent to the ectoderm, adventitial cells, and an inner, single endodermal cell layer. At the electron microscopic level, the typical structural details of the CAM capillaries are demonstrated. Typically, these vessels lie in close association with the inner cell layer of ectoderm.

After 48 hours exposure to paclitaxel at concentrations of 0.25, 0.5, 1, 5, 10, or 30 μg, each CAM was examined under living conditions with a stereomicroscope equipped with a video/computer interface in order to evaluate the effects on angiogenesis. This imaging setup was used at a magnification of 160× which permitted the direct visualization of blood cells within the capillaries; thereby blood flow in areas of interest may be easily assessed and recorded. For this study, the inhibition of angiogenesis was defined as an area of the CAM (measuring 2-6 mm in diameter) lacking a capillary network and vascular blood flow. Throughout the experiments, avascular zones were assessed on a 4 point avascular gradient (Table 1). This scale represents the degree of overall inhibition with maximal inhibition represented as a 3 on the avascular gradient scale. Paclitaxel was very consistent and induced a maximal avascular zone (6 mm in diameter or a 3 on the avascular gradient scale) within 48 hours depending on its concentration.

TABLE 1

| Avascular Gradient | |
|---|---|
| 0 | normal vascularity |
| 1 | lacking some microvascular movement |
| 2* | small avascular zone approximately 2 mm in diameter |
| 3* | avascularity extending beyond the disk (6 mm in diameter) |

The dose-dependent, experimental data of the effects of paclitaxel at different concentrations are shown in Table 2.

TABLE 2

| Agent | Delivery Vehicle | Concentration | Inhibition/n |
|---|---|---|---|
| paclitaxel | methylcellulose (10 ul) | 0.25 ug | 2/11 |
| | methylcellulose (10 ul) | 0.5 ug | 6/11 |
| | methylcellulose (10 ul) | 1 ug | 6/15 |
| | methylcellulose (10 ul) | 5 ug | 20/27 |
| | methylcellulose (10 ul) | 10 ug | 16/21 |
| | methylcellulose (10 ul) | 30 ug | 31/31 |

Typical paclitaxel-treated CAMs are also shown with the transparent methylcellulose disk centrally positioned over the avascular zone measuring 6 mm in diameter. At a slightly higher magnification, the periphery of such avascular zones is clearly evident; the surrounding functional vessels were often redirected away from the source of paclitaxel. Such angular redirecting of blood flow was never observed under normal conditions. Another feature of the effects of paclitaxel was the formation of blood islands within the avascular zone representing the aggregation of blood cells.

In summary, this study demonstrated that 48 hours after paclitaxel application to the CAM, angiogenesis was inhibited. The blood vessel inhibition formed an avascular zone which was represented by three transitional phases of paclitaxel's effect. The central, most affected area of the avascular zone contained disrupted capillaries with extravasated red blood cells; this indicated that intercellular junctions between endothelial cells were absent. The cells of the endoderm and ectoderm maintained their intercellular junctions and therefore these germ layers remained intact; however, they were slightly thickened. As the normal vascular area was approached, the blood vessels retained their junctional complexes and therefore also remained intact. At the periphery of the paclitaxel-treated zone, further blood vessel growth was inhibited which was evident by the typical redirecting or "elbowing" effect of the blood vessels.

Example 32

Screening Assay for Assessing the Effect of Paclitaxel on Smooth Muscle Cell Migration Primary human smooth muscle cells were starved of serum in smooth muscle cell basal media containing insulin and human basic fibroblast growth factor (bFGF) for 16 hours prior to the assay. For the migration assay, cells were trypsinized to remove cells from flasks, washed with migration media and diluted to a concentration of 2-2.5×$10^5$ cells/mL in migration media. Migration media consists of phenol red free Dulbecco's Modified Eagle Medium (DMEM) containing 0.35% human serum albumin. A 100 μL volume of smooth muscle cells (approximately 20,000-25,000 cells) was added to the top of a Boyden chamber assembly (Chemicon QCM CHEMOTAXIS 96-well migration plate).

To the bottom wells, the chemotactic agent, recombinant human platelet derived growth factor (rhPDGF-BB) was added at a concentration of 10 ng/mL in a total volume of 150 μL. Paclitaxel was prepared in DMSO at a concentration of $10^{-2}$ M and serially diluted 10-fold to give a range of stock concentrations ($10^{-8}$ M to $10^{-2}$ M). Paclitaxel was added to cells by directly adding paclitaxel DMSO stock solutions, prepared earlier, at a 1/1000 dilution, to the cells in the top chamber. Plates were incubated for 4 hours to allow cell migration.

Figure 6:
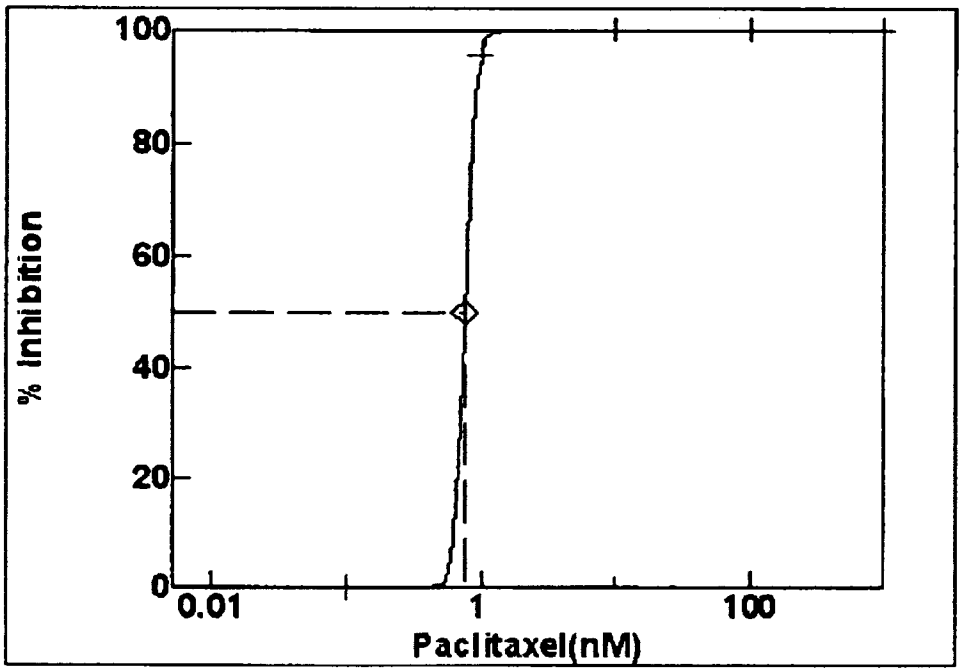
FIG. 6 is a graph showing the results of a screening assay for assessing the effect of paclitaxel on smooth muscle cell migration (paclitaxel $IC_{50}$=0.76 nM).

At the end of the 4 hour period, cells in the top chamber were discarded and the smooth muscle cells attached to the underside of the filter were detached for 30 minutes at 37° C. in Cell Detachment Solution (Chemicon). Dislodged cells were lysed in lysis buffer containing the DNA binding CYQUANT GR dye and incubated at room temperature for 15 minutes. Fluorescence was read in a fluorescence microplate reader at ~480 nm excitation wavelength and ~520 nm emission maxima. Relative fluorescence units from triplicate wells were averaged after subtracting background fluorescence (control chamber without chemoattractant) and average number of cells migrating was obtained from a standard curve of smooth muscle cells serially diluted from 25,000 cells/well down to 98 cells/well. Inhibitory concentration of 50% ($IC_{50}$) was determined by comparing the average number of cells migrating in the presence of paclitaxel to the positive control (smooth muscle cell chemotaxis in response to rhPDGF-BB). See FIG. 6 ($IC_{50}$=0.76 nM). References: Biotechniques (2000) 29: 81; J. Immunol Methods (2001) 254: 85

Example 33

Preparation of Release Buffer

The release buffer is prepared by adding 8.22 g sodium chloride, 0.32 g sodium phosphate monobasic (monohydrate) and 2.60 g sodium phosphate dibasic (anhydrous) to a beaker. 1L HPLC grade water is added and the solution is stirred until all the salts are dissolved. If required, the pH of the solution is adjusted to pH 7.4±0.2 using either 0.1 N NaOH or 0.1 N phosphoric acid.

Example 34

Release Study to Determine Release Profile of the Therapeutic Agent From a Coated Device A sample of the therapeutic agent-loaded catheter is placed in a 15 ml culture tube. 15 ml release buffer (Example 33) is added to the culture tube. The tube is sealed with a TEFLON lined screw cap and is placed on a rotating wheel in a 37° C. oven. At various time points, the buffer is withdrawn from the culture tube and is replaced with fresh buffer. The withdrawn buffer is then analyzed for the amount of therapeutic agent contained in this buffer solution using HPLC.

Example 35

Screening Assay for Assessing the Effect of Paclitaxel on Cell Proliferation

Smooth muscle cells at 70-90% confluency were trypsinized, replated at 600 cells/well in media in 96-well plates and allowed to attachment overnight. Paclitaxel was prepared in DMSO at a concentration of $10^{-2}$ M and diluted 10-fold to give a range of stock concentrations ($10^{-8}$ M to $10^{-2}$ M). Drug dilutions were diluted 1/1000 in media and added to cells to give a total volume of 200 μL/well. Each drug concentration was tested in triplicate wells. Plates containing cells and paclitaxel were incubated at 37° C. for 72 hours.

Figure 7:
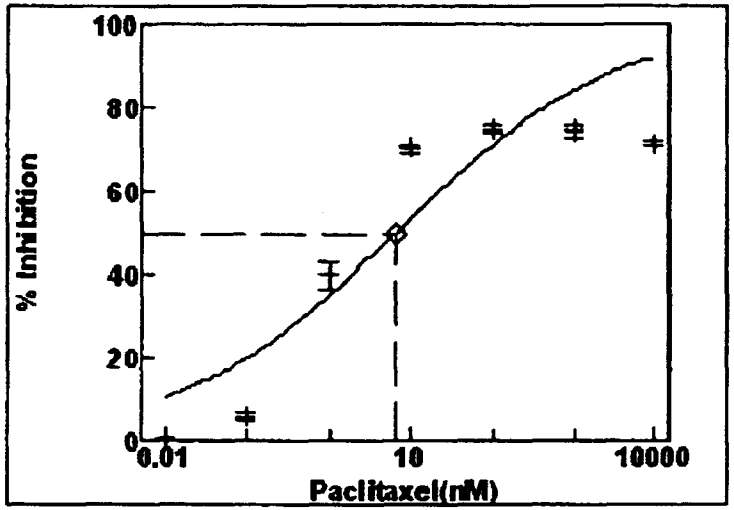
FIG. 7 is graph showing the results of a screening assay for assessing the effect of paclitaxel on proliferation of smooth muscle cells.

To terminate the assay, the media was removed by gentle aspiration. A 1/400 dilution of CYQUANT 400X GR dye indicator (Molecular Probes; Eugene, Oreg.) was added to 1X Cell Lysis buffer, and 200 μL of the mixture was added to the wells of the plate. Plates were incubated at room temperature, protected from light for 3-5 minutes. Fluorescence was read in a fluorescence microplate reader at ~480 nm excitation wavelength and ~520 nm emission maxima. Inhibitory concentration of 50% ($IC_{50}$) was determined by taking the average of triplicate wells and comparing average relative fluorescence units to the DMSO control. An average of n=3 replicate experiments was used to determine $IC_{50}$ values. See FIG. 7 ($IC_{50}$=7 nM).

Figure 9:
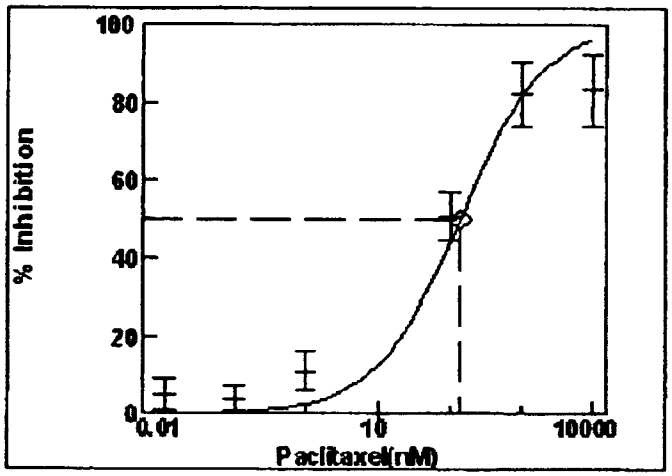
FIG. 9 is graph showing the results of a screening assay for assessing the effect of paclitaxel ($IC_{50}$=134 nM) for proliferation of the murine RAW 264.7 macrophage cell line.

This assay also may be used assess the effect of compounds on proliferation of fibroblasts and murine macrophage cell line RAW 264.7. The results of the assay for assessing the effect of paclitaxel on proliferation of murine RAW 264.7 macrophage cell line were shown in FIG. 9 ($IC_{50}$=134 nM).

Reference: In vitro toxicol. (1990) 3: 219; Biotech. Histochem. (1993) 68: 29; Anal. Biochem. (1993) 213: 426.

Example 36

Perivascular Administration of Paclitaxel

WISTAR rats weighing 250-300 g are anesthetized by the intramuscular injection of Innovar (0.33 ml/kg). Once sedated, they are then placed under Halothane anesthesia. After general anesthesia is established, fur over the neck region is shaved, the skin clamped and swabbed with betadine. A vertical incision is made over the left carotid artery and the external carotid artery exposed. Two ligatures are placed around the external carotid artery and a transverse arteriotomy is made. A number 2 FRENCH FOGART balloon catheter is then introduced into the carotid artery and passed into the left common carotid artery and the balloon is inflated with saline. The catheter is passed up and down the carotid artery three times. The catheter is then removed and the ligature is tied off on the left external carotid artery.

Paclitaxel (33%) in ethelyne vinyl acetate (EVA) is then injected in a circumferential fashion around the common carotid artery in ten rats. EVA alone is injected around the common carotid artery in ten additional rats. (The paclitaxel may also be coated onto an EVA film which is then placed in a circumferential fashion around the common carotid artery.) Five rats from each group are sacrificed at 14 days and the final five at 28 days. The rats are observed for weight loss or other signs of systemic illness. After 14 or 28 days the animals are anesthetized and the left carotid artery is exposed in the manner of the initial experiment. The carotid artery is isolated, fixed at 10% buffered formaldehyde and examined for histology.

A statistically significant reduction in the degree of initimal hyperplasia, as measured by standard morphometric analysis, indicates a drug induced reduction in fibrotic response.

The invention claimed is:

1. A device, comprising a stent and a paclitaxel derivative or a composition comprising a paclitaxel derivative, wherein the paclitaxel derivative inhibits scarring between the device and a host into which the device is implanted.

2. The device of claim 1 wherein the paclitaxel derivative is 9-deoxotaxol, 7-deoxy-9-deoxotaxol, 10-desacetoxy-7-deoxy-9-deoxotaxol, 9-dihydrotaxol compound, 2'-O-ethoxyethyl-7-O-trietylsilyl-9-dihydrotaxol, 2'-O-ethoxyethyl-9-dihydrotaxol, 10-deacetyl-9-dihydrotaxol, 9-dihydrotaxol-7,9-isopropylidene ketal, 9-dihydrotaxol-7, 9-propylidene acetal, or 9-dihydrotaxol-7,9-benzylidene acetal.

3. The device of claim 1 wherein the paclitaxel derivative is 9-dihydrotaxol-7,9-(3,4-dihydroxy) butylidene acetal, 9-dihydrotaxol-7,9-thionocarbonate, 9-dihydrotaxol-7-O-allyl ether, 9-dihydrotaxol 7-O-(2,3-dihydroxypropyl) ether, 9-dihydrotaxol 7-O-(2-dimethylaminoethyl) ether, 9-dihydrotaxol 7-O-(2-hydroxyethyl) ether, 9-dihydrotaxol 7-O-(2-acetoxyethyl) ether, N-debenzoyl-N-t-butoxycarbonyl-9-dihydrotaxol, 10-deacetyl-N-debenzoyl-N-t-butoxycarbonyl-9-dihydrotaxol, or N-debenzoyl-N-t-butylacetyl-9-dihydrotaxol.

4. The device of claim 1 wherein the paclitaxel derivative is N-debenzoyl-N-isobutoxycarbonyl-9-dihydrotaxol, N-debenzoyl-N-adamantoxycarbonyl-9-dihydrotaxol, N-debenzoyl-N-isopropoxycarbonyl-9-dihydrotaxol, N-debenzoyl-N-benzyloxycarbonyl-9-dihydrotaxol, N-debenzoyl-9-dihydrotaxol, N-debenzoyl-N-pivaloyl-9-dihydrotaxol, N-debenzoyl-N-acetyl-9-dihydrotaxol, N-debenzoyl-N-t-butylcarbamyl-9-dihydrotaxol, 9-dihydro-13-acetylbaccatin III, or 2'-O-(1-ethyoxyethyl)-9-dihydrotaxol.

5. The device of claim 1 wherein the paclitaxel derivative is 4,9,12-tris(acetyloxy)-2-benzoyloxy-8-formyl-1,2,3,4,5,6,7,8,10,13,14-undecahydro-1-hydroxy-7,14,-14,17-tetramethyl-1,10-methano-20H-cyclonona[2,3]benz[1,2-b]oxete, β-tertbutyloxycarbonylamino-α-hydroxybenzenepropanoic acid 4,9-bis(acetyloxy)-2-benzoyloxy-8-formyl-1,2,3,4,5,6,7,8,10,13,14-undecahydro-1-hydroxy-7,14,14,17-tetramethyl-1,10-methano-20H-cyclonona[2,3]benz[1,2-b]oxet-12-yl ester, β-benzoylamino-α-hydroxybenzenepropanoic acid 4,9-bis(acetyloxy)-2-benzoyloxy-8-formyl-1,2,3,4,5,6,7,8,10,13,14-undecahydro-1-hydroxy-7,14,14,17-tetramethyl-1,10-methano-20H-cyclonona[2,3]benz[1,2-b]oxet-12-yl ester, 4,9,12(tris(acetyloxy)-2-benzoyloxy-8-formyl-1,2,3,4,5,6,7,8,10,13,14-undecahydro-1-hydroxy-7,14,14,17-tetramethyl-1,10-methano-20H-cyclonona[2,3]benz[1,2-b]oxete, 4,9,12-tris(acetyloxy)-2-benzoyloxy-1,2,3,4,5,6,7,8,10,13,14-undecahydro-1-hydroxy-8-hydroxymethyl-7,14,14,17-tetramethyl-1,10-methano-20H-cyclonona[2,3]benz[1,2-b]oxete, 4,9,12-tris(acetyloxy)-2-benzoyloxy-1,2,3,4,5,6,7,8,10,13,14-undecahydro-1-hydroxy-8-methoxymethyl-7,14,14,17-tetramethyl-1,10-methano-20H-cyclonona[2,3]benz[1,2-b]oxete, 4,9,12-tris(acetyloxy)-2-benzoyloxy-1,2,3,4,5,6,7,8,10,13,14-undecahydro-1-hydroxy-8-ethoxymethyl-7,14,14,17-tetramethyl-1,10-methano-20H-cyclonona[2,3]benz[1,2-b]oxete, 4,9,12-tris(acetyloxy)-8-acetyloxymethyl-2-benzoyloxy-1,2,3,4,5,6,7,8,10,13,14-undecahydro-1-hydroxy-7,14,14,17-tetramethyl-1,10-methano-20H-cyclonona[2,3]benz[1,2-b]oxete, 4,9,12-tris(acetyloxy)-2-benzoyloxy-8-dimethylaminomethyl-1,2,3,4,5,6,7,8,10,13,14-undecahydro-1-hydroxy-7,14,14,17-tetramethyl-1,10-methano-20H-cyclonona[2,3]benz[1,2-b]oxete, or 4,9,12-tris(acetyloxy)-2-benzoyloxy-8-diethylaminomethyl-1,2,3,4,5,6,7,8,10,13,14-undecahydro-1-hydroxy-7,14,14,17-tetramethyl-1,10-methano-20H-cyclonona[2,3]benz[1,2-b]oxete.

6. The device of claim 1 wherein the paclitaxel derivative is 4,9,12-tris(acetyloxy)-2-benzoyloxy-1,2,3,4,5,6,7,8,10,13,14-undecahydro-1-hydroxy-7,14,14,17-tetramethyl-8-methylamino-1,10-methano-20H-cyclonona[2,3]benz[1,2-b]oxete, 4,9,12-tris(acetyloxy)-2-benzoyloxy-1,2,3,4,5,6,7,8,10,13,14-undecahydro-1-hydroxy-7,14,14,17-tetramethyl-8-ethylamino-1,10-methano-20H-cyclonona[2,3]benz[1,2-b]oxete, 4,9,12-tris(acetyloxy)-2-benzoyloxy-1,2,3,4,5,6,7,8,10,13,14-undecahydro-1-hydroxy-7,14,14,17-tetramethyl-8-methylimino-1,10-methano-20H-cyclonona[2,3]benz[1,2-b]oxete, 4,9,12-tris(acetyloxy)-2-benzoyloxy-1,2,3,4,5,6,7,8,10,13,14-undecahydro-1-hydroxy-7,14,14,17-tetramethyl-8-methoxyimino-1,10-methano-20H-cyclonona[2,3]benz[1,2-b]oxete, 4,9,12-tris(acetyloxy)-2-benzoyloxy-1,2,3,4,5,6,7,8,10,13,14-undecahydro-1-hydroxy-7,14,14,17-tetramethyl-8-methylhydrazinomethyl-1,10-methano-20H-cyclonona[2,3]benz[1,2-b]oxete, 4,9,12-tris(acetyloxy)-2-benzoyloxy-8-cyano-1,2,3,4,5,6,7,8,10,13,14-1-undecahydro-1-hydroxy-7,14,14,17-tetramethyl-1,10-methano-20H-cyclonona[2,3]benz[1,2-b]oxete, 4,9,12-tris(acetyloxy)-2-benzoyloxy-1,2,3,4,5,6,7,8,10,13,14-undecahydro-1-hydroxy-7,14,14,17-tetramethyl-1,10-methano-20H-cyclonona[2,3]benz[1,2-b]oxete-8-methylsulfate, 4,9,12-tris(acetyloxy)-2-benzoyloxy-1,2,3,4,5,6,7,8,10,13,14-undecahydro-1-hydroxy-7,14,14,17-tetramethyl-1,10-methano-20H-cyclonona[2,3]benz[1,2-b]oxete-8-methylphosphate, 4,9,12-tris(acetyloxy)-2-benzoyloxy-8-(1,3-dioxolan-2-yl)-1,2,3,4,5,6,7,8,10,13,14-undecahydro-1-hydroxy-7,14,14,17-tetramethyl-1,10-methano-20H-cyclonona[2,3]benz[1,2-b]oxete, or 4,9,12-tris(acetyloxy)-2-benzoyloxy-8-(tetrahydro-oxazole-2-yl)-1,2,3,4,5,6,7,8,10,13,14-undecahydro-1- hydroxy-7,14,14,17-tetramethyl-1,10-methano-20H-cyclonona[2,3]benz[1,2-b]oxete.

7. The device of claim 1 wherein the paclitaxel derivative is 4,9,12-tris(acetyloxy)-2-benzoyloxy-8-(1,3-dithiolane-2-yl)-1,2,3,4,5,6,7,8,10,13,14-undecahydro-1-hydroxy-7,14,14,17-tetramethyl-1,10-methano-20H-cyclonona[2,3]benz[1,2-b]oxete, 4,9-bis(acetyloxy)-2-benzoyloxy-8-formyl-1,12-dihydroxy-1,2,3,4,5,6,7,8,10,13,14-undecahydro-7,14,14,17-tetramethyl-1,10-methano-20H-cyclonona[2,3]benz[1,2-b]oxete, 4,9-bis(acetyloxy)-2-benzoyloxy-1,12-dihydroxy-1,2,3,4,5,6,7,8,10,13,14-undecahydro-8-hydroxymethyl-7,14,14,17-tetramethyl-1,10-methano-20H-cyclonona[2,3]benz[1,2-b]oxete, 4,9-bis(acetyloxy)-2-benzoyloxy-1,12-dihydroxy-1,2,3,4,5,6,7,8,10,13,14-undecahydro-8-methoxymethyl-7,14,14,17-tetramethyl-1,10-methano-20H-cyclonona[2,3]benz[1,2-b]oxete, 4,9-bis(acetyloxy)-2-benzoyloxy-1,12-dihydroxy-1,2,3,4,5,6,7,8,10,13,14-undecahydro-8-ethoxymethyl-7,14,14,17-tetramethyl-1,10-methano-20H-cyclonona[2,3]benz[1,2-b]oxete, 4,9-bis(acetyloxy)-8-acetyloxymethyl-2-benzoyloxy-1,12-dihydroxy-1,2,3,4,5,6,7,8,10,13,14-undecahydro-7,14,14,17-tetramethyl-1,10-methano-20H-cyclonona[2,3]benz[1,2-b]oxete, 4,9-bis(acetyloxy)-2-benzoyloxy-8-dimethylaminomethyl-1,12-dihydroxy-1,2,3,4,5,6,7,8,10,13,14-undecahydro-7,14,14,17-tetramethyl-1,10-methano-20H-cyclonona[2,3]benz[1,2-b]oxete, 4,9-bis(acetyloxy)-2-benzoyloxy-8-diethylaminomethyl-1,12-dihydroxy-1,2,3,4,5,6,7,8,10,13,14-undecahydro-7,14,14,17-tetramethyl-1,10-methano-20H-cyclonona[2,3]benz[1,2-b]oxete, 4,9-bis(acetyloxy)-2-benzoyloxy-1,12-dihydroxy-1,2,3,4,5,6,7,8,10,13,14-1-undecahydro-7,14,14,17-tetramethyl-8-methylamino-1,10-methano-20H-cyclonona[2,3]benz[1,2-b]oxete, or 4,9-bis(acetyloxy)-2-benzoyloxy-1,12-dihydroxy-1,2,3,4,5,6,7,8,10,13,14-undecahydro-7,14,14,17-tetramethyl-8-ethylamino-1,10-methano-20H-cyclonona[2,3]benz[1,2-b]oxete.

8. The device of claim 1 wherein the paclitaxel derivative is 4,9-bis(acetyloxy)-2-benzoyloxy-1,12-dihydroxy-1,2,3,4,5,6,7,8,10,13,14-undecahydro-7,14,14,17-tetramethyl-8-methylimino-1,10-methano-20H-cyclonona[2,3]benz[1,2-b]

oxete, 4,9-bis(acetyloxy)-2-benzoyloxy-1,12-dihydroxy-1,2,3,4,5,6,7,8,10,13,14-undecahydro-7,14,14,17-tetramethyl-8-methoxyimino-1,10-methano-20H-cyclonona[2,3]benz[1,2-b]oxete, 4,9-bis(acetyloxy)-2-benzoyloxy-1,12-dihydroxy-1,2,3,4,5,6,7,8,10,13,14-undecahydro-7,14,14,17-tetramethyl-8-methylhydrazinomethyl-1,10-methano-20H-cyclonona[2,3]benz[1,2-b]oxete, 4,9-bis(acetyloxy)-2-benzoyloxy-8-cyano-1,12-dihydroxy-1,2,3,4,5,6,7,8,10,13,14-undecahydro-7,14,14,17-tetramethyl-1,10-methano-20H-cyclonona[2,3]benz[1,2-b]oxete, 4,9-bis(acetyloxy)-2-benzoyloxy-1,12-dihydroxy-1,2,3,4,5,6,7,8,10,13,14-undecahydro-7,14,14,17-tetramethyl-1,10-methano-20H-cyclonona[2,3]benz[1,2-b]oxete-8-methylsulfate, 4,9-bis(acetyloxy)-2-benzoyloxy-1,12-dihydroxy-1,2,3,4,5,6,7,8,10,13,14-undecahydro-7,14,14,17-tetramethyl-1,10-methano-20H-cyclonona[2,3]benz[1,2-b]oxete-8-methylphosphate, 4,9-bis(acetyloxy)-2-benzoyloxy-8-(1,3-dioxolan-2-yl)-1,12-dihydroxy-1,2,3,4,5,6,7,8,10,13,14-undecahydro-7,14,14,17-tetramethyl-1,10-methano-20H-cyclonona[2,3]benz[1,2-b]oxete, 4,9-bis(acetyloxy)-2-benzoyloxy-8-(tetrahydro-oxazole-2-yl)-1,12-dihydroxy-1,2,3,4,5,6,7,8,10,13,14-undecahydro-7,14,14,17-tetramethyl-1,10-methano-20H-cyclonona[2,3]benz[1,2-b]oxete, 4,9-bis(acetyloxy)-2-benzoyloxy-8-(1,3-dithiolane-2-yl)-1,12-dihydroxy-1,2,3,4,5,6,7,8,10,13,14-undecahydro-7,14,14,17-tetramethyl-1,10-methano-20H-cyclonona[2,3]benz[1,2-b]oxete, or β-benzoylamino-α-hydroxybenzenepropanoic acid 4,9-bis(acetyloxy)-2-benzoyloxy-1,2,3,4,5,6,7,8,10,13,14-undecahydro-1-hydroxy-8-hydroxymethyl-7,14,14,17-tetramethyl-1,10-methano-20H-cyclonona[2,3]benz[1,2-b]oxet-12-yl ester.

9. The device of claim 1 wherein the paclitaxel derivative is β-benzoylamino-α-hydroxybenzenepropanoic acid 4,9-bis(acetyloxy)-2-benzoyloxy-1,2,3,4,5,6,7,8,10,13,14-undecahydro-1-hydroxy-8-methoxymethyl-7,14,14,17-tetramethyl-1,10-methano-20H-cycionona[2,3]benz[1,2-b]oxet-12-yl ester, β-benzoylamino-α-hydroxybenzenepropanoic acid 4,9-bis(acetyloxy)-2-benzoyloxy-1,2,3,4,5,6,7,8,10,13,14-undecahydro-1-hydroxy-8-ethoxymethyl-7,14,14,17-tetramethyl-1,10-methano-20H-cyclonona[2,3]benz[1,2-b]oxet-12-yl ester, β-benzoylamino-α-hydroxybenzenepropanoic acid 4,9-bis(acetyloxy)-8-acetyloxymethyl-2-benzoyloxy-1,2,3,4,5,6,7,8,10,13,14-undecahydro-1-hydroxy-7,14,14,17-tetramethyl-1,10-methano-20H-cyclonona[2,3]benz[1,2-b]oxet-12-yl ester, β-benzoylamino-α-hydroxybenzenepropanoic acid 4,9-bis(acetyloxy)-2-benzoyloxy-8-dimethylaminomethyl-1,2,3,4,5,6,7,8,10,13,14-undecahydro-1-hydroxy-7,14,14,17-tetramethyl-1,10-methano-20H-cyclonona[2,3]benz[1,2-b]oxet-12-yl ester, β-benzoylamino-α-hydroxybenzenepropanoic acid 4,9-bis(acetyloxy)-2-benzoyloxy-8-diethylaminomethyl-1,2,3,4,5,6,7,8,10,13,14-undecahydro-1-hydroxy-7,14,14,17-tetramethyl-1,10-methano-20H-cyclonona[2,3]benz[1,2-b]oxet-12-yl ester, 1,3-benzoylamino-α-hydroxybenzenepropanoic acid 4,9-bis(acetyloxy)-2-benzoyloxy-1,2,3,4,5,6,7,8,10,13,14-undecahydro-1-hydroxy-7,14,14,17-tetramethyl-8-methylaminomethyl-1,10-methano-20H-cyclonona[2,3]benz[1,2b]oxet-12-yl ester, β-benzoylamino-α-hydroxybenzenepropanoic acid 4,9-bis(acetyloxy)-2-benzoyloxy-1,2,3,4,5,6,7,8,10,13,14-undecahydro-1-hydroxy-7,14,14,17-tetramethyl-8-methylimino-1,10-methano-20H-cyclonona[2,3]benz[1,2-b]oxet-12-yl ester, β-benzoylamino-α-hydroxybenzenepropanoic acid 4,9-bis(acetyloxy)-2-benzoyloxy-1,2,3,4,5,6,7,8,10,13,14-undecahydro-1-hydroxy-7,14,14,17-tetramethyl-8-methoxyimino-1,10-methano-20H-cyclonona[2,3]benz[1,2-b]oxet-12yl ester, β-benzoylamino-α-hydroxybenzenepropanoic acid 4,9-bis(acetyloxy)-2-benzoyloxy-1,2,3,4,5,6,7,8,10,13,14-undecahydro-1-hydroxy-7,14,14,17-tetramethyl-8-methyihydrazinomethyl-1,10-methano-20H-cyclonona[2,3]benz[1,2-b]oxet-12-yl ester, or β-benzoylamino-α-hydroxybenzenepropanoic acid 4,9-bis(acetyloxy)-2-benzoyloxy-8-cyano-1,2,3,4,5,6,7,8,10,13,14-undecahydro-1-hydroxy-7,14,14,17-tetramethyl-1,10-methano-20H-cyclonona[2,3]benz[1,2-b]oxet-12-yl ester.

10. The device of claim 1 wherein the paclitaxel derivative is β-benzoylamino-α-hydroxybenzenepropanoic acid 4,9-bis(acetyloxy)-2-benzoyloxy-8-(1,3-dioxolane-2-yl)-1,2,3,4,5,6,7,8,10,13,14-undecahydro-1-hydroxy-7,14,14,17-tetramethyl-1,10-methano-20H-cyclonona[2,3]benz[1,2-b]oxet12-yl ester, β-benzoylamino-α-hydroxybenzenepropanoic acid 4,9-bis(acetyloxy)-2-benzoyloxy-8-(tetrahydro-oxazole-2-yl)-1,2,3,4,5,6,7,8,10,13,14-undecahydro-1-hydroxy-7,14,14,17-tetramethyl-1,10-methano-20H-cyclonona[2,3]benz[1,2-b]oxet-12-yl ester, β-benzoylamino-α-hydroxybenzenepropanoic acid 4,9-bis(acetyloxy)-2-benzoyloxy-8-(1,3-dithiolane-2-yi)-1,2,3,4,5,6,7,8,10,13,14-undecahydro-1-hydroxy-7,14,14,17-tetramethyl-1,10-methano-20H-cyclonona[2,3]benz[1,2-b]oxet12-yl ester, β-tert-butyloxycarbonylamino-α-hydroxybenzenepropanoic acid 4,9-bis(acetyloxy)-2-benzoyloxy-8-formyl-1,2,3,4,5,6,7,8,10,13,14-undecahydro-1-hydroxy-7,14,14,17-tetramethyl-1,10-methano-20H-cyclonona[2,3]benz[1,2-b]oxet-12-yl ester, β-tert-butyloxycarbonylamino-α-hydroxybenzenepropanoic acid 4,9-bis(acetyloxy)-2-benzoyloxy-1,2,3,4,5,6,7,8,10,13,14-undecahydro-1-hydroxy-8-hydroxymethyl-7,14,14,17-tetramethyl-1,10-methano-20H-cyclonona[2,3]benz[1,2b]oxet-12-yl ester, β-tert-butyloxycarbonylamino-α-hydroxybenzenepropanoic acid 4,9-bis(acetyioxy)-2-benzoyloxy-1,2,3,4,5,6,7,8,10,13,14-undecahydro-1-hydroxy-8-methoxymethyl-7,14,14,17-tetramethyl-1,10-methano-20H-cyclonona[2,3]benz[1,2-b]oxet-12-yl ester, β-tert-butyloxycarbonylamino-α-hydroxybenzenepropanoic acid 4,9-bis(acetyioxy)-2-benzoyloxy-1,2,3,4,5,6,7,8,10,13,14-undecahydro-1-hydroxy-8-ethoxymethyl-7,14,14,17-tetramethyl-1,10-methano-20H-cyclonona[2,3]benz[1,2-b]oxet-12-yl ester, β-tert-butyloxycarbonylamino-α-hydroxybenzenepropanoic acid 4,9-bis(acetyloxy)-8-acetyloxymethyl-2-benzoyloxy-1,2,3,4,5,6,7,8,10,13,14-undecahydro-1-hydroxy-7,14,14,17-tetramethyl-1,10-methano-20H-cyclonona[2,3]benz[1,2-b]oxet-12-yl ester, β-tert-butyloxycarbonylamino-α-hydroxybenzenepropanoic acid 4,9-bis(acetyloxyl-2-benzoyloxy-8-dimethylaminomethyl-1,2,3,4,5,6,7,8,10,13,14-undecahydro-1-hydroxy-7,14,14,17-tetramethyl-1,10-methano-20H-cyclonona[2,3]benz[1,2-b]oxet-12-yl ester, or β-tert-butyloxycarbonylamino-α-hydroxybenzenepropanoic acid 4,9-bis(acetyloxy)-2-benzoyloxy-8-diethylaminomethyl-1,2,3,4,5,6,7,8,10,13,14-undecahydro-1-hydroxy-7,14,14,17-tetramethyl-1,10-methano-20H-cyclonona[2,3]benz[1,2-b]oxet-12-yl ester.

11. The device of claim 1 wherein the paclitaxel derivative is β-tert-butyloxycarbonylamino-α-hydroxybenzenepropanoic acid 4,9-bis(acetyloxy)-2-benzoyloxy-1,2,3,4,5,6,7,8,10,13,14-undecahydro-1-hydroxy-7,14,14,17-tetramethyl-8-methylaminomethyl-1,10-methano-20H-cyclonona[-2,3]benz[1,2-b]oxet-12-yl ester, β-tert-butyloxycarbonylamino-α-hydroxybenzenepropanoic acid 4,9-bis(acetyloxy)-2-benzoyloxy-1,2,3,4,5,6,7,8,10,13,14-undecahydro-1-hydroxy-7,14,14,17-tetramethyl-8-methylimino-1,10-methano-20H-cyclonona[2,3]benz[1,2b]oxet-12-yl ester, β-tert-butyloxycarbonylamino-α-hydroxybenzenepropanoic acid 4,9-bis(acetyloxy)-2-benzoyloxy-1,2,3,4,5,6,7,8,10,13,14-undecahydro-1-hydroxy-7,14,14,17-tetramethyl-8-methoxyimino-1,10-methano-20H-cyclonona[2,3]benz[1,2-b]oxet-12-yl ester, β-tert-butyloxycarbonylamino-α-hydroxybenzenepropanoic acid 4,9-bis(acetyloxy)-2-benzoyloxy-1,2,3,4,5,6,7,8,10,13,14-undecahydro-1-hydroxy-7,14,14,17-tetramethyl-8-methylhydrazinomethyl-1,10-methano-20H-cyclonona[2,3]benz[1,2-b]oxet-12-yl ester, β-terttert-butyloxycarbonylamino-α-hydroxybenzenepropanoic acid 4,9-bis(acetyloxy)-2-benzoyloxy-8-cyano-1,2,3,4,5,6,7,8,10,13,14-undecahydro-1-hydroxy-7,14,14,17-tetramethyl-1,10-methano-20H-cyclonona[2,3]benz[1,2-b]oxet-12-yl ester, β-tert-butyloxycarbonylamino-α-hydroxybenzenepropanoic acid 4,9-bis(acetyloxy)-2-benzoyloxy-8-(1,3-dioxolane-2-yl)-1,2,3,4,5,6,7,8,10,13,14-undecahydro-1-hydroxy-7,14,14,17-tetramethyl-1,10-methano-20H-cyclonona[2,3]benz[1,2-b]oxet-12-yl ester, β-tert-butyloxycarbonylamino-α-hydroxybenzenepropanoic acid 4,9-bis(acetyloxy)-2-benzoyloxy-8-(1,3-dithiolane-2-yl)-1,2,3,4,5,6,7,8,10,13,14-undecahydro-1-hydroxy-7,14,14,17otetramethyl-1,10-methano-20H-cyclonona[2,3]benz[1,2-b]oxet-12-yl ester, β-benzoylamino-α-hydroxy-γ-(1-naphthyl)propanoic acid 4,9-bis(acetyloxy)-2-benzoyloxy-1,2,3,4,5,6,7,8,10,13,14-undecahydro-1-hydroxy-8-hydroxymethyl-7,14,14,17-tetramethyl-1,10-methano-20H-cyclonona[2,3]benz[1,2-b]oxet-12-yl ester, or β-benzoylamino-α-hydroxy-γ-(2-naphthyl)propanoic acid 4,9-bis(acetyloxy)-2-benzoyloxy-1,2,3,4,5,6,7,8,10,13,14-undecahydro-1-hydroxy-8-hydroxymethyl-7,14,14,17-tetramethyl-1,10-methano-20H-cyclonona[2,3]benz[1,2-b]oxet-12-yl ester.

12. The device of claim 1 wherein the paclitaxel derivative is β-benzoylamino-α-hydroxy-γ-(pyridyl)propanoic acid 4,9-bis(acetyloxy)-2-benzoyloxy-1,2,3,4,5,6,7,8,10,13,14-undecahydro-1-hydroxy-8-hydroxymethyl-7,14,14,17-tetramethyl-1,10-methano-20H-cyclonona[2,3]benz[1,2-b]oxet-12-yl ester, β-tert-benzoylamino-α-hydroxy-γ-(thienyl)propanoic acid 4,9-bis(acetyloxy)-2-benzoyloxy-1,2,3,4,5,6,7,8,10,13,14-undecahydro-1-hydroxy-8-hydroxymethyl-7,14,14,17-tetramethyl-1,10-methano-20H-cyclonona[2,3]benz[1,2-b]oxet-12-yl ester, β-benzoylamino-α-hydroxy-γ-(furyl)propanoic acid 4,9-bis(acetyloxy)-2-benzoyloxyo-1,2,3,4,5,6,7,8,10,13,14-undecahydro-1-hydroxy-8-hydroxymethyl-7,14,14,17-tetramethyl-1,10-methano-20H-cyclonona[2,3]benz[1,2-b]oxet-12-yl ester, β-benzoylamino-α-hydroxy-γ-(oxazolyl)propanoic acid 4,9-bis(acetyloxy)-2-benzoyloxy-1,2,3,4,5,6,7,8,10,13,14-undecahydro-1-hydroxy-8-hydroxymethyl-7,14,14,17-tetramethyl-1,10-methano-20H-cyclonona[2,3]benz[1,2-b]oxet-12-yl ester, β-benzoylamino-α-hydroxy-γ-(imidazolyl)propanoic acid 4,9-bis(acetyloxy)-2-benzoyloxy-1,2,3,4,5,6,7,8,10,13,14-undecahydro-1-hydroxy-8-hydroxymethyl-7,14,14,17-tetramethyl-1,10-methano-20H-cyclonona[2,3]benz[1,2-b]oxet-12-yl ester, β-benzoylamino-α-hydroxy-γ-(pyrazinyl)propanoic acid 4,9-bis(acetyloxy)-2-benzoyloxy-1,2,3,4,5,6,7,8,10,13,14-undecahydro-1-hydroxy-8-hydroxymethyl-7,14,14,17-tetramethyl-1,10-methano-20H-cyclonona[2,3]benz[1,2-b]oxet-12-yl ester, or β-benzoylamino-α-hydroxy-γ-(pyridazinyl)propanoic acid 4,9-bis(acetyloxy)-2-benzoyloxy-1,2,3,4,5,6,7,8,10,13,14-undecahydro-1-hydroxy-8-hydroxymethyl-7,14,14,17-tetramethyl-1,10-methano-20H-cyclonona[2,3]benz[1,2-b]oxet-12-yl ester.

13. The device of claim 1 wherein the device delivers the paclitaxel derivative locally to tissue proximate to the device.

14. The device of claim 1, further comprising a coating, wherein the coating comprises the paclitaxel derivative.

15. The device of claim 1, further comprising a coating, wherein the paclitaxel derivative is present in the coating in an amount ranging between about 0.0001% to about 1% by weight.

16. The device of claim 1, further comprising a coating, wherein the coating further comprises a polymer.

17. The device of claim 1, further comprising a polymer or a polymeric carrier.

18. The device of claim 1, further comprising a second pharmaceutically active agent.

19. The device of claim 18, wherein the second pharmaceutically active agent is an anti-inflammatory agent, an agent that inhibits infection, or an anti-thrombotic agent.

20. The device of claim 1, further comprising a visualization agent or an echogenic material.

21. The device of claim 1 wherein the device is sterile.

22. The device of claim 1 wherein the paclitaxel derivative is released into tissue in the vicinity of the device after deployment of the device.

23. The device of claim 1 wherein the paclitaxel derivative is released in effective concentrations from the device over a period ranging from about 1 month to 6 months.

24. The device of claim 1 wherein the device comprises about 0.01 μg to about 10 μg, about 10 μg to about 10 mg, about 10 mg to about 250 mg, about 250 mg to about 1000 mg, or about 1000 mg to about 2500 mg of the paclitaxel derivative.

25. The device of claim 1 wherein a surface of the device comprises less than 0.01 μg, about 0.01 μg to about 1 μg, about 1 μg to about 10 μg, about 10 μg to about 250 μg, about 250 μg to about 1000 μg, or about 1000 μg to about 2500 μg of the paclitaxel derivative per $mm^2$ of device surface to which the paclitaxel derivative is applied.

26. The device of claim 1 wherein the stent is a vascular stent, a coronary stent, a peripheral stent, a covered stent, a gastrointestinal stent, an esophageal stent, a biliary stent, a colonic stent, a tracheal or bronchial stent, a genital-urinary stent, a nasal or sinus stent, or an ENT stent.

* * * * *